(12) United States Patent
Auricchio et al.

(10) Patent No.: US 7,517,870 B2
(45) Date of Patent: Apr. 14, 2009

(54) USE OF COMPOUNDS THAT INTERFERE WITH THE HEDGEHOG SIGNALING PATHWAY FOR THE MANUFACTURE OF A MEDICAMENT FOR PREVENTING, INHIBITING, AND/OR REVERSING OCULAR DISEASES RELATED WITH OCULAR NEOVASCULARIZATION

(75) Inventors: Alberto Auricchio, Naples (IT); Markus Hildinger, Naples (IT); Enrico Maria Surace, Naples (IT)

(73) Assignee: Fondazione Telethon, Rome (IT)

( * ) Notice: Subject to any disclaimer, the term of this patent is extended or adjusted under 35 U.S.C. 154(b) by 430 days.

(21) Appl. No.: 11/002,882

(22) Filed: Dec. 3, 2004

(65) Prior Publication Data

US 2006/0276391 A1 Dec. 7, 2006

(51) Int. Cl.
*A61K 38/00* (2006.01)
*A61K 38/17* (2006.01)

(52) U.S. Cl. .......................................... 514/176; 514/2

(58) Field of Classification Search ....................... None
See application file for complete search history.

(56) References Cited

U.S. PATENT DOCUMENTS 5,760,028 A * 6/1998 Jadhav et al. .......... 514/211.03
6,514,724 B1 * 2/2003 McMahon et al. ......... 435/69.1
2004/0060568 A1 * 4/2004 Dudek et al. ................ 128/898

FOREIGN PATENT DOCUMENTS

WO WO 200230462 A2 * 4/2002

* cited by examiner

*Primary Examiner*—Brandon J Fetterolf
(74) *Attorney, Agent, or Firm*—Young & Thompson

(57) ABSTRACT

The present invention concerns the use of compounds that interfere with the hedgehog signaling pathway for the manufacture of a medicament for preventing, inhibiting, and/or reversing ocular diseases related with ocular neovascularization. Particularly, the above-mentioned diseases are (wet) age-related macular degeneration, (proliferative) diabetic retinopathy, neovascular glaucoma, retinal vein occlusion, or retinopathy of prematurity (ROP).

12 Claims, 5 Drawing Sheets

USE OF COMPOUNDS THAT INTERFERE WITH THE HEDGEHOG SIGNALING PATHWAY FOR THE MANUFACTURE OF A MEDICAMENT FOR PREVENTING, INHIBITING, AND/OR REVERSING OCULAR DISEASES RELATED WITH OCULAR NEOVASCULARIZATION

1. BACKGROUND OF THE INVENTION

In the following sections, the inventors include passages and cite publications that are available in the public domain. The author of the patent would like to acknowledge in particular "The Merck Manual of Diagnosis and Therapy", and U.S. patent applications Ser. Nos. 10/652,298, 09/977,864, 09/88,384.

It must be noted that as used herein and in the appended claims, the singular forms "a" and "the" include plural referents unless the context clearly dictates otherwise. Thus, for example, reference to "a cell" or "the cell" includes a plurality ("cells" or "the cells"), and so forth. Moreover, the word "or" can either be exclusive in nature (i.e., either A or B, but not A and B together), or inclusive in nature (A or B, including A alone, B alone, but also A and B together). One of skill in the art will realize which interpretation is the most appropriate—unless it is detailed by reference in the text as "either A or B" (exclusive "or") or "and/or" (inclusive "or").

1.1 Field of the Invention

The present invention relates to methods of preventing, inhibiting, and/or reversing ocular neovascularization in a mammalian subject comprising administering to the subject a therapeutically effective amount of a substance that interferes with the Hedgehog signaling pathway. Ocular neovascularization is a major cause of blindness in developed countries. It is causally involved in many ocular diseases including age-related macular degeneration, (proliferative) diabetic retinopathy, neovascular glaucoma, retinal vein occlusion, or retinopathy of prematurity (ROP). Current treatments are of limited efficacy and associated with significant adverse effects, reflecting the high unmet need in those disease areas.

More specifically, the invention relates to the use of a small molecule such as cyclopamine, or a protein such as a (humanized) monoclonal antibody to interfere with Hedgehog signaling. The inventors demonstrate in the present invention that interference with Hedgehog signaling by means of e.g., cyclopamine, is able to prevent, inhibit and/or reverse ocular neovascularization in a mammalian subject, which will have a therapeutic benefit on said subject.

1.2 Background of the Invention

Ocular neovascularization is involved in multiple pathologies of the eye such as (wet) age-related macular degeneration, (proliferative) diabetic retinopathy, neovascular glaucoma, retinal vein occlusion, or retinopathy of prematurity (ROP). Yet, there is still a high degree of unmet need in the prevention, treatment and/or cure of diseases caused by ocular neovascularization: Many patients affected by one of those diseases will face (legal) blindness in the end.

The present invention relates to methods for preventing, inhibiting, and/or reversing ocular neovascularization by interfering with the Hedgehog signaling pathway in general, and by inhibiting Smoothened (Smo) function in particular. The present invention also comprises administering to a mammalian subject a substance that interferes with the Hedgehog signaling pathway in general, and that inhibits Smoothened (Smo) function in particular such as (for example) cyclopamine.

The inventors are the first to show (1) the involvement of Hedgehog signaling in general, and the requirement for Smoothened activity in particular in ocular neovascularization, and (2) that interfering with Hedgehog signaling in general, and inhibition of Smoothened activation in particular can prevent, inhibit and/or reverse ocular neovascularization. In the preferred embodiment, the inventors prove that administering cyclopamine to a mammalian subject can inhibit Smoothen activation and thus prevent and/or inhibit ocular neovascularization. Generally speaking, upon administration of a Hedgehog-interference substance (such as cyclopamine), ocular neovascularization will be prevented, inhibited and/or reversed, thus preventing and/or ameliorating the pathologies associated with ocular neovascularization. Also provided are pharmaceutical kits containing the Hedgehog-signaling interfering substance in a suitable pharmaceutical suspension for administration.

The present invention offers a novel, useful and non-obvious method for treating, inhibiting and/or preventing ocular diseases that are caused (in part) by ocular neovascularizatlon by administering to a mammalian subject a substance that interferes with the Hedgehog signaling pathway. Also provided are pharmaceutical kits containing the Hedgehog pathway interfering substance in a suitable pharmaceutical suspension for administration.

1.3 Description of Prior Art

1.3.1 Hedgehog Signaling

Analysis of the *Drosophila melanogaster* Hedgehog mutant, named after its prominent phenotype—epidermal spikes in larval segments that normally are devoid of these extensions—led to the cloning of the original Hedgehog gene.

In vertebrates, the Hedgehog (Hh) protein family of secreted glycoproteins comprises at least four members: Three of these members, Sonic Hedgehog (Shh), Desert Hedgehog (Dhh), and India Hedgehog (Ihh), seem to be expressed in all vertebrates, including mammals. They are also highly conserved between species. A fourth member, tiggie-winkle Hedgehog (Thh), appears specific to fish. Exemplary Hedgehog genes and proteins are described in PCT publications WO 95/18856 and WO 96/17924.

Hedgehog (Hh) proteins act as morphogens in many tissues during embryonic development as mediators of intercellular signaling. The Hedgehog pathway is important in regulating cell patterning, differentiation, proliferation, survival and growth in the embryo and the adult ([1]; [2]; [3]). Vertebrate Hedgehog proteins are crucial to a number of epithelial-mesenchymal inductive interactions during neuronal development, limb development, lung, bone, hair follicle and gut formation ([4, 5] [6] [7] [8] [9]). More recently, their role in tumorigenesis and angiogenesis has been described in adult organisms.

Shh, the most widely expressed Hedgehog protein, apparently is also the most potent member of its family. It is broadly expressed during development, and sonic null mice are embryonic lethal ([10]; [11] [12]; [13]) Shh is primarily involved in morphogenic and neuroinductive activities such as neural tube, craniofacial, limb, and kidney development. Indian Hedgehog (Ihh) is involved in bone development during embryogenesis and in bone formation in the adult ([14]; [15]). Desert Hedgehog (Dhh) is the most restricted in terms of expression, and Dhh null mice are viable; it is expressed primarily in the testes, both in mouse embryonic development and in the adult rodent and human ([16]; [17]).

Hedgehog proteins exert their function as part of the Hedgehog signaling pathway that is tightly regulated by many inhibitors at different levels. The Hedgehog receptor, Patched (Ptc) is a 12 transmembrane protein with a sterol sensing domain. The mammalian genome contains 2 patched genes, ptc1 and ptc2. In the absence of Hedgehog, Ptc binds and inhibits the function of Smoothened (Smo), a 7 transmembrane protein that functions as a co-receptor. Once Hh binds to Ptc, Ptc does not further inhibit Smo. Smo's activation in turn leads to the activation of fused (Fu), a serine-threonine kinase, and the disassociation of a zinc finger transcription factor of the mammalian Gli family (corresponding to Ci in *Drosophila*), from the microtubule-associated Fu-Gli-Su(fu) complex [Su(fu): Suppressor of Fused]. Gli proteins are large, multifunctional transcription factors, and their activities are intrinsically regulated. The uncomplexed Gli protein is then transported into the nucleus where it activates downstream target genes of the Hedgehog pathway including genes associated with cell cycle progression, the ptc1 and gli1 gene ([18]; [19, 20]; [21]; [22]; [23]).

The various Hedgehog proteins consist of a signal peptide, a highly conserved N-terminal region, and a more divergent C-terminal domain. During their passage through the secretory pathway, Hedgehog proteins are extensively modified: They undergo an internal autoproteolytic cleavage yielding a 19 kD N-terminal peptide and a 26-28 kD C-terminal peptide; the 19 kD peptide is then further modified at its N-and C-termini by palmitoyl and cholesteryl adducts, respectively. These lipid modifications lead to a tight association of the 19 kD fragment with membranes. In addition, the diffusion of the 19 kD N-terminal peptide is further limited by binding to the Hip1, Patched1 (Ptc1) and Patched2 (Ptc2) transmembrane receptors, all of which are expressed on Hh responsive cells, and by interaction with heparin through an N-terminal basic domain. The C-terminal peptide on the contrary is freely diffusible. Yet, it is the 19 kD peptide that acts directly on distant cells in developing tissues. This remote action requires the transmembrane transporter-like protein Dispatched (Disp) for release of Hh from secreting cells and other proteins and enzymes.

Three Gli proteins have been identified in mammals (Gli1, Gli2, Gli3). Proteolysis of Gli2 and Gli3 results in the generation of strong repressors of gene transcription, whereas the Gli1 repressor seems to be weak. Shh inhibits repressor formation by Gli3, but not by Gli2, and the formation of potent activators of Gli2, and perhaps of other Gli proteins, depends on Hh signaling ([24-28]

Gli proteins can form Hedgehog signaling complexes with several other signaling components, including the kinesin-like protein Costal-2, Fu, and Su(fu) [29-33]. In these complexes Gli proteins are regulated by cytoplasmic sequestration, phosphorylation, and proteolysis. They can be found in both the nucleus and cytoplasm. In the cytoplasm, they are part of a multimolecular complex that is tethered to the cytoskeleton. In the absence of Hh, Gli proteins are cleaved by the proteasome, and C-terminally truncated forms termed "Gli repressors" translocate to the nucleus, where they act as dominant transcriptional repressors. Upon Hh-induced Smo activation, Gli repressor formation is inhibited and full-length labile activators of transcription are made instead.

1.3.2 Involvement of Hedgehog in Diseases

Prior art describes involvement of Hedgehog in several diseases. When the Hedgehog-pathway is activated or maintained inappropriately, cell proliferation can become misregulated. Some examples are cancer [34-36] [37] [38] and skin-related disorders such as psoriasis [39, 40].

Hedgehog misregulation has been associated with a whole range of cancers including BCC, medulloblastoma, rhabdomyosarcoma, cutaneous epithelial tumors, oral squamous cell carcinoma, pancreatic cancer, digestive tract tumors, glioma, pancreatic adenosarcoma, esophageal and stomach cancer, small cell lung cancer. In addition to controlling cell differentiation and tissue patterning, Hh signalling also regulates the proliferation of distinct cell types via direct activation of cell-cycle control genes such as cyclin D1 and cyclin D2 in mammalian cells [41], which could explain its involvement in a vast variety of tumors.

1.3.3 Vasculogenesis, Angiogenesis and Neovascularization

Vascular development involves vasculogenesis, where endothelial cells form a primary tubular network, as well as angiogenesis, in which vessel size and structure are modified, and branching occurs to insure that all cells receive adequate oxygen delivery. In adults, angiogenesis occurs in response to tissue hypoxia/ischemia and plays an important role in determining the progression of ischemic heart disease and cancer.

For purposes of this invention, vasculogenesis is a physiological process, and pathological (abnormal) vasculogenesis is referred to as neovascularization. Neovascularization—in a more narrow definition—is a form of pathologic, abnormal vasculogenesis that causes visual loss. Neovascularization can be caused by a multitude of molecular mechanisms, and the basic pathological mechanisms that trigger the cascade of events are many such as ischemia, inflammatory, or metabolic events. One hypothesis for the process of neovascularization suggests that increased vascular permeability leads to retinal oedema and vascular fragility resulting in haemorrhage, or fibro-vascular proliferation with tractional and rhegmatogenous retinal detachment. Furthermore, for purposes of this invention, angiogenesis can be either physiological or pathological.

The discovery of the molecular mechanisms of physiological vasculogenesis and angiogenesis vs. neovascularization and pathological angiogenesis helped to recognize two classes of diseases: One where the therapeutic angiogenesis can repair the tissue damages (arteriosclerosis, ischemia-induced pathologies such as myocardial infarction, coronary artery disease, peripheral vascular disease, limb ischemia and stroke) and the other one where inhibition of neovascularization and/or pathological angiogenesis can cure the disease or delay its progression (age-related macular degeneration, (proliferative) diabetic retinopathy, neovascular glaucoma, retinal vein occlusion, or retinopathy of prematurity (ROP), benign and malignant angiogenic tumors, progression of malignant tumors, psoriasis, rheumatoid arthritis).

Thus, the induction of angiogenesis and vascular growth is beneficial for tissue repair and would healing whereas inhibition of angiogenic growth factors can prevent angiogenesis driven pathologies.

Neovascularization in the retina is initiated by the ischemic injury, hyperglycaemia induced PKC activation, and or hypoxia. Hypoxia plays a causal role in the pathological events that lead to the formation of new blood vessels, which ultimately results in blindness. Under hypoxic stimuli HIF-1α triggers the expression of a number of proangiogenic genes, including Vascular Endothelial Growth Factor (VEGF). Glial cells in the hypoxic retina not only produce VEGF, but also IL-8 and HGF as well and pericytes start to express bFGF all responsible for the neoangiogenesis. Yet, as the inventors demonstrate, the Hedgehog-signaling pathway is also able of inducing VEGF expression. VEGF is one of the most important growth factors that have been extensively associated with neovascular diseases of the eye.

As mentioned before, angiogenesis is the process by which new capillaries are formed by sprouting from pre-existing vessels. It is a highly attractive target for therapeutic intervention since it represents a final common pathway in processes that are multifactorial in aetiology. Angiogenesis is regulated through the combined action of pro-angiogenic and anti-angiogenic factors.

Pro-angiogenic factors favor angiogenesis. They can be classified into (a) Cytokines and growth factors such as Fibroblast Growth Factor (FGF), Vascular Endothelial Growth Factor (VEGF), TGFα and TGFβ, Angiopoietins, Interleukins (IL-1, IL-6, IL-8), GM-CSF, PDGF, PDECGF, EGF, TNFα, HGF; (b) Cell surface receptors such as Flk1 (=VEGFR2; =KDR; VEGF receptor), Flt1 (=VEGFR1; VEGF receptor; [8]), Neurophilin; (c) Integrins such as $\alpha_v\beta_3$ (whose expression is induced by, e.g., TNFα, FGF-2, GM-CSF etc. ), $\alpha_v\beta_5$; (d) Proteases such as matrix metalloproteases (MMPs); (e) Small molecules (e.g., retinoic acid; Cu).

Anti-angiogenic factors inhibit angiogenesis. They can be classified into (a) Cytokines and growth factors such as Troponin, Platelet Factor 4, TGFβ1, Interferon α and Interferon β, Somatostatin; (b) Proteolytic fragments such as Angiostatin, Endostatin (collagen XVIII fragment), Thrombospondin fragment, Fibronectin fragments, Vasostatin (kallikrein fragment); (c) Tissue inhibitors of metalloproteases (TIMPs); (d) Small molecules such as some retinoids, zinc or 2-methoxyestradiol; (e) Other proteins such as laminin or CM101.

1.3.4 Hedgehog Signaling in Angiogenesis and Neovascularization

Pola et al. [42] have shown that cells in the adult vasculature both express ptc1 and can respond to exogenous Hedgehog. They also were able to prove that Hedgehog is able to induce robust neovascularization in the corneal pocket model of angiogenesis. In the same publication, the group found that the Hedgehog-signaling pathway is present in adult cardiovascular tissues and can be activated in vivo. Shh was able to induce robust angiogenesis, characterized by distinct large-diameter vessels. Shh also augmented blood-flow recovery and limb salvage following operatively induced hind-limb ischemia in aged mice. In vitro, Shh had no effect on endothelial-cell migration or proliferation; instead, it induced expression of two families of angiogenic cytokines, including all three vascular endothelial growth factor-1 isoforms and angiopoietins-1 and -2 from interstitial mesenchymal cells. In summary, the group discovered a novel role for Shh as an indirect angiogenic factor that regulates expression of multiple angiogenic cytokines—indicating a potential therapeutic use of Shh for ischemic disorders.

Whereas this group has shown a role for Shh in ischemic diseases, there has not yet been reports of the involvement of Hedgehog in general and Shh in particular in ocular neovascularization. Moreover, there have not yet been reports that interfering with Hedgehog signaling in general and Shh signaling in particular, and interference by inhibiting Smo activation in detail, will inhibit, prevent, and/or revert ocular neovascularization.

1.3.5 Eye Diseases

Ocular neovascularization is causatively involved in many eye diseases such as (proliferative) diabetic retinopathy, neovascular glaucoma, retinal vein occlusion an/or retinopathy of prematurity (ROP).

1.3.5.1 Age-related Macular Degeneration (AMD)

Age related macular degeneration (AMD) is the leading cause of legal blindness in the elderly Caucasian population, but is relatively rare in other races. The degenerative condition of the central retina (macula) only affects central vision, leaving peripheral vision intact. AMD affects approximately 30% or more of the Caucasian population age 75 and greater. The molecular mechanism underling AMD is not fully understood and is the major obstacle in the development of aetiologic and prophylactic treatments. The primary lesion appears to occur deep to the central retina with deposits known as drusen. Drusen are thought to be metabolic by-products, the increasing deposition of which may further interfere with the high metabolic activity of the macula.

There is no medical treatment for AMD and only a very small number of subjects with late stage disease are amenable to a palliative and minimally effective laser photocoagulation therapy.

There are two different forms of AMD: In atrophic macular degeneration (dry form), there is pigmentary disturbance in the macular region, but no elevated macular scar and no hemorrhage or exudation in the region of the macula; in exudative macular degeneration (wet form), which is much less common (approximately 10% of all cases of AMD), there is formation of a subretinal network of choroidal neovascularization often associated with intraretinal hemorrhage, subretinal fluid, pigment epithelial detachment, and hyperpigmentation. Eventually, this complex contracts and leaves a distinct elevated scar at the posterior pole. In that respect, "wet" AMD is more visually debilitating compared to the dry form. Both forms of age-related macular degeneration are often bilateral and are preceded by drusen in the macular region.

For the present invention, the "wet" form of AMD is of primary interest as it involves ocular neovascularization. This form of the disease occurs when a tiny frond of vessels (capillaries) breaks through a layer of the retina known as Bruch's membrane, and grows beneath the macula. This is known as a choroidal neovascular membrane (CNVM). The abnormal vessels of the CNVM may leak fluid causing a localized swelling, or worse, result in a localized bleed. This is the condition most likely to result in legal blindness. It is important to realize, however, that even "wet" AMD doesn't lead to "cane blindness", given that peripheral vision remains intact, although often legally blind (<20/200 vision). Although most patients will not lose all vision, even the reduction is a great burden on the affected individual. Current therapy involves appropriate laser photocoagulation, if fluorescein angiography demonstrates a neovascular network outside the fovea.

Yet, there still remains a high degree of unmet need in treating and preventing "wet" AMD.

1.3.5.2 (Proliferative) Diabetic Retinopathy

Diabetic retinopathy is the leading cause of acquired blindness among Americans under the age of 65. It can be particularly severe in persons with insulin-dependent diabetes mellitus (IDDM; type I diabetes mellitus); it also occurs frequently in persons with chronic non-insulin-dependent diabetes mellitus (NIDDM; type II diabetes mellitus). The degree of retinopathy is highly correlated with the duration of the diabetes.

Proliferative retinopathy is characterized by abnormal new vessel formation (neovascularization), which grows on the vitreous surface or extends into the vitreous cavity. In advanced disease, neovascular membranes can occur, resulting in a traction retinal detachment. Vitreous hemorrhages may result from neovascularization. Visual symptoms vary, depending on pathologic events. For example, a sudden severe loss of vision can occur when there is intravitreal hemorrhage. Visual prognosis with proliferative retinopathy is more guarded if associated with severe retinal ischemia, extensive neovascularization, or extensive fibrous tissue formation.

Proliferative diabetic retinopathy (PDR) carries the greatest risk of visual loss. The condition is characterized by the development of neovascularization on or adjacent to the optic nerve and vitreous or pre-retinal hemorrhage (hemorrhage in the vitreous humor or in front of the retina). PDR usually occurs in eyes with advanced background diabetic retinopathy and is thought to be secondary to ischemia (lack of oxygen or blood flow) of the retina. The neovascular vessels are abnormal and have a tendency to break and bleed into the vitreous humor of the eye. In addition to sudden vision loss, this may lead to more permanent complications, such as tractional retinal detachment and neovascular glaucoma.

Patients with PDR should receive scatter laser photocoagulation (also known as PRP, or pan-retinal photocoagulation, a laser treatment of the ischemic peripheral retina) as soon as possible following diagnosis of the condition. This treatment is also known as pan-retinal laser photocoagulation. By causing regression of the neovascular tissues, the risk of severe vision loss is substantially reduced. PRP is an in-office or out-patient procedure done with or without an anesthetic injection adjacent to the eye. The laser treatment usually takes less than 30 to 45 minutes per session. A complete laser treatment, however, may require up to 3 or 4 different sessions, with a total of one to two thousand laser applications ("spots").

In some patients with PDR, the vitreous hemorrhage prevents the ophthalmologist from performing the laser treatment. Simply put, the blood is in the way of the laser beam. If the vitreous hemorrhage fails to clear within a few weeks or months, a vitrectomy surgery may be performed to mechanically clear the hemorrhage and laser photocoagulation is then applied, either at the time of the vitrectomy or shortly thereafter. Patients who have tractional retinal detachment are usually scheduled for vitrectomy surgery promptly.

As comparison: Nonproliferative retinopathy (formerly known as background retinopathy) is characterized by increased capillary permeability, microaneurysms, hemorrhages, exudates, and edema. Visual symptoms generally do not occur in the early stages of nonproliferative retinopathy. However, significant early visual changes can occur in a small number of patients, especially in those with NIDDM.

There is no cure for diabetic retinopathy, and patients still show high unmet need: Apart from diabetes and blood pressure control, panretinal photocoagulation may diminish or eliminate proliferative retinopathy and neovascularization of the iris. Early photocoagulation decreases the risk of neovascular glaucoma development. Vitrectomy may be useful in cases of vitreous hemorrhage.

1.3.5.3 Retinopathy of Prematurity (ROP, also Retrolental Fibroplasia)

ROP is a bilateral ocular disorder of abnormal retinal vascularization in premature infants, especially those of lowest birth weight, with outcomes ranging from normal vision to blindness.

Retinopathy of prematurity (ROP) represents a proliferation of abnormal retinal blood vessels that occurs almost exclusively in prematurely delivered infants. More than 80% of infants weighing <1 kg at birth develop ROP. The risk of ROP rises with decreasing birth weights, and advancing neonatology now frequently allows infants weighing under two pounds to survive. The belief that oxygen supplementation for premature infants causes ROP is still widely held, at least amongst the general public. Historically, ROP was recognized to occur primarily in infants who required high oxygen supplementation due to their immature lungs. Once this association was made, the delivery of oxygen was curtailed in attempt to reduce ROP. This was somewhat effective in reducing the incidence of ROP, but the incidence of cerebral palsy and hyaline membrane (lung) disease increased. Other risk factors for the development of ROP include extended duration of time in oxygen, the need for respiratory stimulants such as aminophylline or theophylline, and maternal bleeding from the conditions known as abruptio placentae or placenta previa.

Neonatologists now give enough oxygen to sustain life and prevent neurological disorders, yet limit the risk of ROP. The risk of some degree of ROP in these infants is extremely high. Because the inner retinal blood vessels start growing about midpregnancy and have fully vascularized the retina by full term, their growth is incomplete in premature infants. Susceptibility to ROP varies but correlates with the proportion of retina that remains avascular at birth. ROP occurs when normal blood vessels in the retina fail to reach the retinal periphery, leaving retinal tissue ischemic (oxygen deprived). When this occurs, neovascularization may occur at the border of the ischemic (oxygen starved) and non-ischemic retina. The neovascular tissue may grow into the vitreous humor resulting in tractional membranes, and cause tractional retinal detachment if not treated. In addition, an abnormal ridge of tissue forms between the vascularized central retina and the nonvascularized peripheral retina. In severe ROP, these new vessels invade the vitreous, and sometimes the entire vasculature of the eye becomes engorged ("plus" disease). The abnormal vessel growth often subsides spontaneously but, in about 4% of survivors weighing <1 kg at birth, progresses to produce retinal detachments and vision loss within 2 to 12 mo postpartum.

Children with healed ROP have a higher incidence of myopia, strabismus, and amblyopia. A few children with moderate, healed ROP are left with cicatricial scars (e.g., dragged retina or retinal folds) but no initial retinal detachments and are at risk for retinal detachments later in life.

Prevention of premature birth is the best preventive of ROP. After a preterm birth, oxygen should be used only in amounts sufficient to avoid hypoxia. Improved ROP prevention remains a focus of intensive investigation worldwide. In severe ROP, cryotherapy or laser photocoagulation to ablate the peripheral avascular retina can halve the incidence of retinal fold or detachment. Retinal vascularization must be closely followed at 1-to 2-week intervals until the vessels have matured sufficiently without reaching the preconditions for cryotherapy or laser photocoagulation to the ischemic retina. If retinal detachments occur in infancy, scleral buckling surgery or vitrectomy with lensectomy may be considered, but these procedures are late rescue efforts with low benefit.

1.3.5.4 Neovascular Glaucoma

Neovascular glaucoma is a form of glaucoma that most commonly is associated with proliferative diabetic retinopathy (PDR) and central retinal vein occlusion (CRVO). Other causative factors include carotid occlusive disease (carotid artery plaques resulting in significant lumen narrowing or occlusion), central retinal artery occlusion (CRAO), temporal arteritis, and many other conditions that result in ischemia (reduced blood flow) of the retina or ciliary body.

The mechanism of neovascular glaucoma is the development of neovascularization in the angle of the eye causing obstruction to fluid egress via the trabecular meshwork, the primary outflow pathway of the eye. When the retina is ischemic, it is theorized that an angiogenic factor, acting as a local hormone, is released from the ischemic tissue and this results in the development of neovascularization. Neovascularization occurs primarily in the following locations: optic nerve, retina, iris, and angle of the eye.

Ablation of the ischemic tissue via pan-retinal laser photocoagulation (PRP), therefore, is believed to minimize the angiogenic factor production, and the neovascular tissue consequently regresses. Medical management, including the use of topical eye-drop medications and steroids, is usually used until the PRP takes effect (vessels regress). Laser ablation of the vessels in the angle of the eye is only occasionally effective and may be used as a temporary measure to help keep the angle open.

For those patients in whom laser photocoagulation (PRP) is not effective, glaucoma filtration surgery, implantation of a glaucoma drainage device (tube shunt), or cyclocryotherapy (freezing therapy of the ciliary body, which produces aqueous fluid) may all be effective. Laser cyclophotocoagulation, which entails use of a laser to destroy part of the ciliary body, may also be used.

The prevention of neovascular glaucoma is extraordinarily important since treatment is difficult and the prognosis is generally poor. Prophylaxis includes the use of PRP laser for patients with both proliferative diabetic retinopathy (PDR) and central retinal vein occlusion (CRVO) in which extensive ischemia (reduced blood flow) is present. Unfortunately, it is not always possible to determine which patients with these underlying conditions will develop neovascular glaucoma, even with the most meticulous care.

1.3.5.5 Retinal Vein Occlusion: Central Retinal Vein Occlusion

Central retinal vein occlusion (CRVO) presents with mild to severe, sudden, painless, visual loss. The majority of patients will either have systemic hypertension, chronic open-angle glaucoma, or significant atherosclerosis. The final insult of these disorders causing the CRVO is generally a thrombus of the central retinal vein just as it enters the eye. The ophthalmologist may find mild to severe hemorrhages and cotton-wool spots in the retina, the latter of which indicate ischemia.

The initial vision on presentation is a good predictor of the final visual outcome. That is, the worse the vision initially, the worse the final visual acuity. In fact, in half of patients, final visual acuity remains within 3 lines on the eye chart. There are two basic classes that ophthalmologists will use to classify CRVO's upon presentation. These are the ischemic (poor blood flow) and non-ischemic types. The latter of these types generally has much better vision upon presentation and fewer clinical findings on exam.

The prognosis for the non-ischemic type of CRVO is good. The ischemic type almost always has vision of 20/100 or worse on initial presentation, and has a much higher risk of developing complications. These patients must be following carefully, perhaps every few weeks, to evaluate for signs of neovascularization both in the retina and on the iris. Neovascularization of the retina or optic nerve may result in bleeding (vitreous hemorrhage) and neovascularization of the iris may result in intractable glaucoma (high pressure failing to respond to all conventional therapy). Both conditions, if they develop, are typically treated with laser to the retina (pan-retinal photocoagulation) in attempt to cause regression of the neovascularization. Eyes considered to be in the ischemic CRVO category, may also be treated with laser photocoagulation of the retina to prevent these dreaded complications.

1.3.5.6 Retinal Vein Occlusion: Branch Retinal Vein Occlusion

A branch retinal vein occlusion (BRVO) may present with decreased vision, peripheral vision loss, distortion of vision, or "blind spots." The condition is unilateral and usually develops in a patient with hypertension or diabetes mellitus. The cause of the condition is a localized thrombus development in a branch retinal vein due to arteriosclerosis (hardening of the arteries) in an adjacent branch retinal arteriole.

The ophthalmologist will see retinal hemorrhages along the involved retinal vein, the pattern of which nearly always leads to the correct diagnosis. Many ophthalmologists will obtain a fluorescein angiogram during the recovery period if neovascularization is suspected. A fluorescein angiogram is an extraordinarily safe, in-office diagnostic procedure, in which fluorescein dye is administered by IV or sometimes orally, and retinal photography is subsequently completed.

Patients are typically re-evaluated every one to two months to evaluate for chronic macular edema (swelling) and/or neovascularization. If macular edema persists beyond 3 to 6 months and visual acuity is reduced below 20/40, the patient may be treated with focal laser. For those patients who meet the guidelines for treatment, laser photocoagulation has been shown to improve vision and to increase the chances that final visual acuity will be 20/40 or better. If neovascularization develops, or if the BRVO involves a significantly large area of retina, which may predispose to the development of neovascularization, the patient may undergo pan-retinal laser photocoagulation. Many patients will have resolution of the retinal hemorrhages and macular swelling, over a several month period, with retention of good vision. For those requiring laser treatment, the ophthalmologist will use rather strict criteria to determine which patients will benefit from laser treatment.

According to the above, there is still a high degree of unmet need in the prevention, treatment and/or cure of diseases caused by ocular neovascularization. Particularly, current treatments are limited efficacy and associated with significant adverse effects.

The inventors of the present invention have now found that the Hedgehog signaling is involved in ocular neovascularization and that interfering with Hedgehog signaling upon administration of a Hedgehog-interference substance can prevent, inhibit and/or reverse ocular neovascularization.

1.3.6 Hedgehog Inhibitors

The Hedgehog (Hh) pathway can be blocked at different levels, and many Hh inhibitors are in the public domain [43-47]. They are primarily investigated as potential anti-cancer agents. The actual nature of the Hh inhibitor used does not limit the scope of the invention. This invention primarily addresses the therapeutic use of substances that interfere with Hedgehog signaling in general, and Shh signaling in particular, to prevent, inhibit and/or revert ocular neovascularization and the pathological consequences resulting from ocular neovascularization. Thus, the nature of the Hh inhibitor, and the biological target of the Hh inhibitor should not be considered as limitations of the present invention.

Inhibition of Hh signaling has been reported with antibodies, such as (for example) antibodies directed against Sonic Hedgehog (Shh). Moreover, several specific Smoothened (Smo) inhibitors have been identified such as e.g., Cyclopamine [46, 48, 49]. Some other inhibitors of Smo have been identified in two large-scale screens for small-molecule inhibitors. These inhibitors include several that potently block a constitutively activated form of Smo that is known to cause BCCs (SANT1-4, Cur61414) [47]

1.3.6.1 Cyclopamine

Cyclopamine, a natural alkaloid derivative that is isolated from a plant of the lily family Veratum californicum, represents the first member of a class of small chemical compounds that specifically inhibit the Hh pathway. In its preferred embodiment, administration of cyclopamine to a mammalian subject was used to prevent ocular neovascularization. Cyclopamine is a potent teratogen that specifically inhibits Smo activity by binding to its heptahelical bundle. Treatment of mice that carry Hh-dependent tumors with cyclopamine results in growth inhibition and regression of cancerous tissue, but does not affect the health of treated animals. Thus it seems that Hh inhibition by cyclopamine causes little, if any, toxic effects on cells that do not depend on Hh signalling. Cyclopamine, however, is difficult to synthesize in large quantities and therefore is not applicable as a therapeutic agent for diseases where a large quantity of drug is needed (e.g., cancer)—a factor that might also apply to a modified and more effective version of this compound, KAADcyclopamine. Yet, for ocular diseases, a smaller quantity of cyclopamine is sufficient to be therapeutically effective. Moreover, as many ocular diseases that involve ocular neovascularization affect primarily older humans, teratogenicity might not be a safety limitation for the majority of patients.

Apart from its use in cancer treatment, cyclopamine has also been applied successfully to the treatment of skin-related disorders such as psoriasis ([39, 40]).

Cyclopamine had been in-licensed by Curis from Johns Hopkins University School of Medicine in September 2000. In August 2004, data were published that showed the Hh signalling pathway played an essential role in endothelial tube formation during vasculogenesis [50, 51]. One month later, a study published in Cancer Research showed that cyclopamine blocks the growth of breast cancer cells via the Hh signalling pathway [52].

1.3.6.2 Hedgehog Interacting Protein 1 (Hip1)

As mentioned, in response to Hh, at least two proteins that are up-regulated: Patched1 (Ptc1), the Hh receptor, a general target in both invertebrate and vertebrate organisms, and Hip1, a Hh-binding protein that is vertebrate specific [53]. Hip1 stands for Hedgehog interacting protein 1 (Hip1). It is a negative regulator of Hh signaling. It has been shown that loss of Hip1 function results in specific defects in two Hh target issues, the lung, a target of Sonic hedgehog (Shh) signaling, and the endochondral skeleton, a target of Indian hedgehog (Ihh) signaling.

Human Hip1 (SEQ ID NO:4) is encoded in humans by the HHIP gene (GeneID: 64399; SEQ ID NO:3). HHIP comprises 13 exons and spans >91 kb encoding a protein of ~700 amino acids which shares 94% sequence identity with mouse Hip1 (SEQ ID NO:2). The sequence of the mouse cDNA for Hip1 is listed in SEQ ID NO:1. HHIP maps to chromosome 4q31.21→q31.3. It is a type I transmembrane protein [54] that binds all mammalian Hh proteins with an affinity similar to that of Ptc1, but this binding most likely regulates the availability of ligand, thereby attenuating signaling rather than activating a novel pathway. Like Ptc, expression of Hip1 is up-regulated in response to Hh signaling [54], but unlike Ptc, there is no evidence that it acts by directly regulating Smo. Therefore, Hip1 adds a second layer of control to the Hh negative feedback mechanism, a layer that is exclusive to vertebrates.

By deleting the transmembrane domain and retaining and/or inserting a secretion signal peptide, one can create a secreted version of Hip1 (sHip1) (SEQ ID NO:6), which is encoded by the correspondingly modified cDNA, sHIP1 (SEQ ID NO:5). This secreted version is still able to bind and sequester Hedgehog, thus interfering with Hedgehog signaling. A secreted version of Hip1 has been published in prior art [55] [56].

1.3.7 Gene Transfer

Gene transfer systems can be classified along different dimensions
(A) Nature or origin of the system
(B) Delivery mechanism;
(C) Site of gene transfer (e.g., ex vivo, in vitro, in vivo).

(A) Based on the nature or origin of the gene transfer system, existing delivery systems for nucleic acid compositions can be subdivided into three groups: (1) viral vectors, (2) non-viral vectors, and (3) naked nucleic acids. Regarding vector targeting (specificity) and efficiency, viral vector systems are superior to conventional non-viral vectors and naked nucleic acids. On the other hand, non-viral vectors and naked nucleic acids are safer, easier to upscale in production and allow for the delivery of modified nucleic acids compared to viral vectors.

(B) Alternatively, based on the delivery mechanism, gene transfer methods fall into the following three broad categories: (1) physical (e.g., electroporation, direct gene transfer and particle bombardment), (2) chemical (e.g. lipid-based carriers and other non-viral vectors) and (3) biological (e.g. virus or bacterium derived vectors).

(C) Gene therapy methodologies can also be described by delivery site. Fundamental ways to deliver genes include ex vivo gene transfer, in vivo gene transfer, and in vitro gene transfer. In ex vivo gene transfer, cells are taken from the subject and grown in cell culture. The nucleic acid composition is introduced in the cells, the transduced or transfected cells are (in some instances) expanded in number and then reimplanted in the subject. In in vitro gene transfer, the transformed cells are cells growing in culture, such as tissue culture cells, and not particular cells from a particular subject. These "laboratory cells" are transfected or transduced; the transfected or transduced cells are then in some instances selected and/or expanded for either implantation into a subject or for other uses. In vivo gene transfer involves introducing the nucleic acid composition into the cells of the subject when the cells are within the subject.

Several delivery mechanisms may be used to achieve gene transfer in vivo, ex vivo, and/or in vitro:

Mechanical (i.e. physical) methods of DNA delivery can be achieved by direct injection of DNA, such as microinjection of DNA into germ or somatic cells, pneumatically delivered DNA-coated particles, such as the gold particles used in a "gene gun," and inorganic chemical approaches such as calcium phosphate transfection. It has been found that physical injection of plasmid DNA into muscle cells yields a high percentage of cells that are transfected and have a sustained expression of marker genes. The plasmid DNA may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products. Particle-mediated gene transfer may also be employed for injecting DNA into cells, tissues and organs. With a particle bombardment device, or "gene gun," a motive force is generated to accelerate DNA coated high-density particles (such as gold or tungsten) to a high velocity that allows penetration of the target organs, tissues or cells. Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. The techniques of particle-mediated gene transfer and electroporation are well known to those of ordinary skill in the art.

Chemical methods of gene therapy involve carrier mediated gene transfer through the use of fusogenic lipid vesicles such as liposomes or other vesicles for membrane fusion. A carrier harboring a DNA of interest can be conveniently introduced into body fluids or the bloodstream and then site specifically directed to the target organ or tissue in the body. Liposomes, for example, can be developed which are cell specific or organ specific. The foreign DNA carried by the liposome thus will be taken up by those specific cells. Injection of immunoliposomes that are targeted to a specific receptor on certain cells can be used as a convenient method of inserting the DNA into the cells bearing the receptor. Another carrier system that has been used is the asialoglycoprotein/polylysine conjugate system for carrying DNA to hepatocytes for in vivo gene transfer. Transfected DNA may also be complexed with other kinds of carriers so that the DNA is carried to the recipient cell and then resides in the cytoplasm or in the nucleoplasm of the recipient cell. DNA can be coupled to carrier nuclear proteins in specifically engineered vesicle complexes and carried directly into the nucleus. Carrier mediated gene transfer may also involve the use of lipid-based proteins which are not liposomes. For example, lipofectins and cytofectins are lipid-based positive ions that bind to negatively charged DNA, forming a complex that can ferry the DNA across a cell membrane. Another method of carrier mediated gene transfer involves receptor-based endocytosis. In this method, a ligand (specific to a cell surface receptor) is made to form a complex with a gene of interest and then injected into the bloodstream; target cells that have the cell surface receptor will specifically bind the ligand and transport the ligand-DNA complex into the cell.

Biological gene therapy methodologies usually employ viral vectors to insert genes into cells. The transduced cells may be cells derived from the patient's normal tissue, the patient's diseased tissue, or may be non-patient cells. Viral vectors that have been used for gene therapy protocols include but are not limited to, retroviruses, lentivruses, other RNA viruses such as pollovirus or Sindbis virus, adenovirus, adeno-associated virus, herpes viruses, simian virus 40, vaccinia and other DNA viruses.

Replication-defective murine retroviral vectors are commonly utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol, and env genes flanked by 5' and 3' long terminal repeats (LTR). Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most dividing cell types, precise single copy vector integration into target cell chromosomal DNA, and ease of manipulation of the retroviral genome. For example, altered retrovirus vectors have been used in ex vivo and in vitro methods to introduce genes into peripheral and tumor-infiltrating lymphocytes, hepatocytes, epidermal cells, myocytes, or other somatic cells (which may then be introduced into the patient to provide the gene product from the inserted DNA). For descriptions of various retroviral systems, see, e.g., U.S. Pat. No. 5,219,740; [49-53]. The main disadvantage of retroviral systems is that retroviral vectors can only infect dividing cells. Lentiviral vectors overcome this limitation. Nevertheless, production of retro-and lentiviral vectors is complex, and the virions are not very stable compared to other viruses. More recently, the danger of inducing cancer through insertional mutagenesis has been raised as a major safety concern [54] [55].

A number of adenovirus based gene delivery systems have also been developed. Human adenoviruses are double stranded, linear DNA viruses with a protein capsid that enter cells by receptor-mediated endocytosis. Adenoviral vectors have a broad host range and are highly infectious, even at low virus titers. Moreover, adenoviral vectors can accommodate relatively long transgenes compared to other systems. A number of adenovirus based gene delivery systems have also been described [56-62]. The main limitation of adenoviral vectors is their high degree of immunogenicity, which limits their use in respect to applications that require long-term gene expression.

For many applications, long-term gene expression (over several years) will have to be achieved. This is also the case for the present invention. So far, primarily adeno-associated virus based vectors allow for this. Most other viral vectors are limited by expression of viral genes so that transduced cells will be eliminated by the immune system (e.g., adenoviral vectors), gene silencing (retroviral vectors or lentiviral vectors) or questionable safety profile (e.g., retroviral vectors or adenoviral vectors).

1.3.7.1 Adeno-Associated Viral Vectors

The present invention uses adeno-associated virus-based vectors [63] [64] [65] for the transfer of an RNAi expression cassette into the appropriate target cells of a mammalian subject in vivo.

Adeno associated virus (AAV) is a small nonpathogenic virus of the parvoviridae family. AAV is distinct from the other members of this family by its dependence on a helper virus for replication. The approximately 5 kb genome of AAV consists of single stranded DNA of either plus or minus polarity. The ends of the genome are short inverted terminal repeats (ITRs), which can fold into hairpin structures and serve as the origin of viral DNA replication. Physically, the parvovirus virion is non-enveloped and its icosohedral capsid is approximately 20 nm in diameter. To date, at least 8 serologically distinct AAVs have been identified and isolated from humans or primates and are referred to as AAV types 1-8. The most extensively studied of these isolates are AAV type 2 (AAV2) and AAV type 5 (AAV5).

The genome of AAV2 is 4680 nucleotides in length and contains two open reading frames (ORFs). The left ORF encodes the non-structural Rep proteins, Rep40, Rep52, Rep68 and Rep78, which are involved in regulation of replication and transcription in addition to the production of single-stranded progeny genomes. Furthermore, two of the Rep proteins have been associated with the preferential integration of AAV2 genomes into a region of the q arm of human chromosome 19. Rep68/78 have also been shown to possess NTP binding activity as well as DNA and RNA helicase activities. The Rep proteins possess a nuclear localization signal as well as several potential phosphorylation sites. Mutation of one of these kinase sites resulted in a loss of replication activity. The ends of the genome are short inverted terminal repeats, which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation. This binding serves to position Rep68/78 for cleavage at the trs, which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

The right ORF of AAV2 encodes related capsid proteins referred to as VP1, 2 and 3. These capsid proteins form the icosahedral, non-enveloped virion particle of ~20 nm diameter. VP1, 2 and 3 are found in a ratio of 1:1:10. The capsid proteins differ from each other by the use of alternative splicing and an unusual start codon. Deletion analysis has shown that removal or alteration of VP1, which is translated from an alternatively spliced message, results in a reduced yield of infectious particles. Mutations within the VP3 coding region result in the failure to produce any single-stranded progeny DNA or infectious particles.

The findings described in the context of AAV2 are generally applicable to other AAV serotypes as well.

The following features of AAV have made it an attractive vector for gene transfer. AAV vectors possess a broad host range [66], transduce both dividing and non dividing cells in vitro and in vivo and maintain high levels of expression of the transduced genes in the absence of a significant immune response to the transgene product in general. Moreover, as wild-type AAV is non-pathogenic, AAV vector particles are assumed to be non-pathogenic as well (in contrast to adenoviral vectors). Viral particles are heat stable, resistant to solvents, detergents, changes in pH and temperature. The ITRs have been shown to be the only cis elements required for replication and packaging and may contain some promoter activities. Thus, AAV vectors encode no viral genes.

2. SUMMARY OF THE INVENTION

The following paragraphs will provide a summary of the invention.

2.1 Substance or General Idea of the Claimed Invention

The present invention relates to methods for preventing, inhibiting, and/or reversing ocular neovascularization by interfering with the Hedgehog signaling pathway. Ocular neovascularization is the leading cause of blindness in developed countries. It is involved in many pathologies such as (wet) age-related macular degeneration, (proliferative) diabetic retinopathy, neovascular glaucoma, retinal vein occlusion or retinopathy of prematurity (ROP). Yet, there is still a high degree of unmet need in the prevention, treatment and/or cure of diseases caused by ocular neovascularization.

Interference with the Hedgehog signaling pathway is achieved by administering to a mammalian subject a substance that interferes with the Hedgehog signaling pathway. In one embodiment, cyclopamine interferes with the Hedgehog signaling pathway by inhibiting Smo function, thus preventing ocular neovascularization in a mammalian subject. In another embodiment, In another embodiment, a modified, secreted form of Hip1 is either injected in the eye of a mammalian subject, or is expressed by a gene transfer vector in the eye of a mammalian subject. Said modified, secreted form of Hip1 sequesters Hedgehog outside the cell, thus inhibiting binding of Hedgehog to its receptor, Ptc1, and interfering with Hedgehog signaling.

The inventors are the first to show
(1) The involvement of Hedgehog signaling in ocular neovascularization, and
(2) That interfering with Hedgehog signaling can prevent, inhibit and/or reverse ocular neovascularization. Upon administration of a Hedgehog-interference substance, ocular neovascularization will be prevented, inhibited and/or reversed, thus preventing and/or ameliorating the pathologies associated with ocular neovascularization. In one embodiment, the inventors prove interference with the Hedgehog signaling pathway by administration of cyclopamine to a mammalian subject in a model of choroidal neovascularization.

Also provided are pharmaceutical kits containing the Hedgehog-signaling interfering substance in a suitable pharmaceutical suspension for administration.

We disclose that the method of the present invention
(1) Is effective in preventing, inhibiting, and/or reversing ocular neovascularization in a mammalian subject in vivo
(2) Will lead to a therapeutic benefit for a mammalian subject suffering from a disease caused by ocular neovascularization such as (wet) age-related macular degeneration, (proliferative) diabetic retinopathy, neovascular glaucoma, retinal vein occlusion or retinopathy of prematurity (ROP).
(3) Will achieve the effects listed in (1) and (2) by interfering with the Hedgehog signaling pathway.

A significant aspect of the present invention relates to the demonstration that interfering with Hedgehog signaling in vivo in mammalian subjects by administering a substance that interferes with Hedgehog signaling is able to prevent, inhibit, and/or reverse ocular neovascularization. This had not been previously described in the art. Thus, the present invention provides, for the first time, a demonstration of the importance of interfering with the Hedgehog signaling pathway to prevent, inhibit, and/or reverse ocular neovascularization. In the preferred embodiment, the inventors prevent ocular neovascularization by administering cyclopamine to the eye of a mammalian subject in vivo. Cyclopamine is an inhibitor of Smo, and thus interferes with Hedgehog signaling, particularly Sonic Hedgehog signaling.

Also disclosed are pharmaceutical kits containing a substance that interferes with Hedgehog signaling in a suitable pharmaceutical suspension for administration. In this aspect, the invention provides a pharmaceutical kit for delivery of said substance. The kit may contain a container for administration of a predetermined dose. The kit further may contain a suspension containing the substance that interferes with Hedgehog signaling for delivery of a predetermined dose, said suspension comprising
(a) the substance that interferes with Hedgehog signaling, and
(b) a physiologically compatible carrier.

In one embodiment, the Hedgehog-signaling interfering substance will be administered to the eye by intravitreal injection. In another embodiment, the Hedgehog-signaling interfering substance will be administered to the eye by subretinal injection. In yet another embodiment, the Hedgehog-signaling interfering substance is formulated in a suspension that can be topically applied to the eye, either in the form of a crème or in the form of eye drops. Many different formulations and ways of administrations can be envisioned, and should not be considered limiting on the scope of the present invention.

Practice of the present invention will provide useful medical applications as described below under "Utility Of The Present Invention". In summary, the invention provides a method for treating a mammalian subject with a disease caused in total or in part by ocular neovascularization by administering to the mammalian subject in vivo a substance that interferes with the Hedgehog signaling pathway in general, and the Shh signaling pathway in particular. In its preferred embodiment, the mammalian subject is a human patient, and the substance that interferes with Shh signaling is cyclopamine, which inhibits Shh signaling by inhibiting Smo function.

This invention also provides a method of treating a subject having an eye disorder ameliorated by interfering with the Hedgehog signaling pathway, comprising administering to the subject a therapeutically effective amount of the instant pharmaceutical composition comprising a substance that interferes with Hedgehog signaling.

Moreover, this invention also provides a method of inhibiting in a subject the onset of an eye disorder ameliorated by interfering with the Hedgehog signaling pathway, comprising administering to the subject a prophylactically effective amount of the instant pharmaceutical composition comprising a substance that interferes with Hedgehog signaling.

The exact nature of the substance that interferes with Hedgehog signaling does not limit the scope of the invention: Said substance can be a small molecule (such as cyclopamine), an antibody (such as 5E1), a protein or protein fragment, an aptamer, a small interfering RNA, a ribozyme, an antisense nucleic acid molecule, a soluble receptor, a modified version of a Hedgehog protein, a peptoid, or any other substance that interferes with Hedgehog signaling. In case of proteins and nucleic acids: These substances might be either directly administered to the patient, or expressed within the patient by using a recombinant gene transfer vector such as an AAV vector.

Moreover, the therapeutic of the present invention can be administered to the subject by many means. The exact method chosen should not limit the scope of the present invention. For example, the therapeutic of the present invention can be injected intravitreally or subretinally into the eye, it could be applied topically (e.g., as a crème), or it can be administered in the form of eye drops. In preferred embodiments, the therapeutic of the invention is applied locally to the eye.

Similarly, the therapeutic of the present invention can be formulated in different forms and suspended in a multitude of pharmaceutically acceptable carriers. The choice of formulation and pharmaceutical carrier should not limit the scope of the present invention.

To summarize: The present invention describes for the first time that interference with Hedgehog signaling in general, and Shh signaling in particular, prevents, inhibits, and/or reverses ocular neovascularization, a process involved in many eye-related pathologies. Interference with Hedgehog signaling in general, and sonic Hedgehog signaling in particular will exert a therapeutic benefit on the individual treated with a Hedgehog-signaling interference substance. The exact nature or composition of said substance, its formulation and suspension, its way of administration should not limit the scope of this invention: As long as a substance—including a combination of substances—interferes with Hedgehog signaling in general, and Sonic Hedgehog signaling in particular, to inhibit, prevent, and/or reverse ocular neovascularization in a mammalian subject, it should be considered claimed by the present invention. Whereas the inventors describe the usefulness of the present invention for a range of eye diseases with high unmet need—such as (wet) age-related macular degeneration, (proliferative) diabetic retinopathy, neovascular glaucoma, retinal vein occlusion, or retinopathy of prematurity (ROP)—it should be understood that the artisan will be able to identify further eye diseases whose pathology involve ocular neovascularization. The exact nature of the eye disease should not be considered a limitation of the present invention: All eye pathologies that involve ocular neovascularization in their aetiology should be considered claimed in the present invention.

2.2 Advantages of the Invention over Prior Approaches

Ocular neovascularization is the leading cause of blindness in developed countries due to its involvement in multiple pathologies such as (wet) age-related macular degeneration, (proliferative) diabetic retinopathy, neovascular glaucoma, retinal vein occlusion, or retinopathy of prematurity (ROP). Yet, there is still a high degree of unmet need in the prevention, treatment and/or cure of diseases caused by ocular neovascularization.

The present invention relates to methods for preventing, inhibiting, and/or reversing ocular neovascularization by interfering with the Hedgehog signaling pathway by administering to a mammalian subject a substance that interferes with the Hedgehog signaling pathway. In the preferred embodiments, the Hedgehog-signaling interfering substance is formulated in an acceptable pharmaceutical carrier and/or suspension and provided in a pharmaceutical kit.

Thus, the present invention is of great medical use to address the high unmet need in eye disorders whose aetiology involve ocular neovascularization. By making use of the present invention, a therapeutic benefit can be achieved in a mammalian individual (including a human being) suffering from or being at risk of an eye disease that involves ocular neovascularization in its pathological process.

The present invention is also novel in the respect that the inventors are the first to show
(1) The involvement of Hedgehog signaling in general, and Shh signaling in particular, and Smo activity in detail, in ocular neovascularization, and
(2) That interfering with Hedgehog signaling in general, Shh signaling in particular, and Smo activity in detail, can prevent, inhibit and/or reverse ocular neovascularization: Upon administration of a Hedgehog-signaling-interference substance, ocular neovascularization will be prevented, inhibited and/or reversed, thus preventing and/or ameliorating the pathologies associated with ocular neovascularization. In one embodiment, cyclopamine is used as to interfere with Hedgehog signaling in general, and Shh signaling in particular. Cyclopamine interferes with Shh signaling by inhibiting Smo function, thus preventing and/or inhibiting ocular neovascularization, e.g., in an animal model of choroidal neovascularization.

It has been shown in prior art (Pola et al.) that cells in the adult vasculature both express ptc1 and can respond to exogenous Hedgehog. Pola et al. also were able to prove that Hedgehog is able to induce robust neovascularization in the corneal pocket model of angiogenesis. In the same publication, the group found that the Hedgehog-signaling pathway is present in adult cardiovascular tissues and can be activated in vivo. Shh was able to induce robust angiogenesis, characterized by distinct large-diameter vessels. Shh also augmented blood-flow recovery and limb salvage following operatively induced hind-limb ischemia in aged mice. In summary, the group discovered a novel role for Shh as an indirect angiogenic factor that regulates expression of multiple angiogenic cytokines—indicating a potential therapeutic use of Shh for ischemic disorders.

However, whereas this group has shown a role for Shh in ischemic diseases, there has not yet been reports of the involvement of Hedgehog in general and Shh in particular in ocular neovascularization. Moreover, there have not yet been reports that interfering with Hedgehog signaling in general and Shh signaling in particular, and interference by inhibiting Smo activation in detail, will inhibit, prevent, and/or revert ocular neovascularization and the pathological processes involved with it. The inventors are the first to show that particular effect, thus providing an advancement and improvement in the art over prior knowledge.

Prior art also describes a role for inhibiting Hedgehog in cancer and skin-related diseases such as Psoriasis. It has also been published that cyclopamine is able of inhibiting Smo function, and thus inhibiting Shh signaling. However, it has not yet been published that interfering with the Hedgehog signaling pathway is able to prevent, inhibit and/or revert ocular neovascularization. The inventors are the first to show that particular effect, thus providing an advancement and improvement in the art over prior knowledge.

Furthermore, the inventors are the first to show a therapeutic benefit of using a Hedgehog-signaling-interfering substance in a mammalian subject to prevent, inhibit and/or reverse ocular neovascularization in vivo in an animal model of choroidal neovascularization (CNV). Prior art has not yet described the involvement of Shh signaling in ocular neovascularization, and that cyclopamine can be used to modulate ocular neovascularization.

3. DETAILED DESCRIPTION OF THE INVENTION

The present invention relates to methods of preventing, inhibiting, and/or reversing ocular neovascularization in a mammalian subject comprising administering to the subject a therapeutically effective amount of a substance that interferes with the Hedgehog signaling pathway. Ocular neovascularization is a major cause of blindness in developed countries. It is causally involved in many ocular diseases including age-related macular degeneration, (proliferative) diabetic retinopathy, neovascular glaucoma, retinal vein occlusion or retinopathy of prematurity (ROP). Current treatments are of limited efficacy and associated with significant adverse effects, reflecting the high unmet need in those disease areas.

More specifically, the invention relates to the use of a small molecule such as cyclopamine, or a protein such as a (humanized) monoclonal antibody to interfere with Hedgehog signaling in general, and Shh signaling in particular. The inventors demonstrate in the present invention that interference with Hedgehog signaling by means of e.g., cyclopamine, is able to prevent, inhibit and/or reverse ocular neovascularization in a mammalian subject, which will have a therapeutic benefit on said subject.

Also provided are pharmaceutical kits containing the substance that interferes with Hedgehog signaling in a suitable pharmaceutical suspension for administration.

The practice of the present invention will employ, unless otherwise indicated, conventional methods of virology, chemistry, microbiology, molecular biology and recombinant DNA techniques within the skill of the art. Such techniques are explained fully in the literature; see, e.g., Sambrook, et al. Molecular Cloning: A Laboratory Manual (Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, vol. I & II (P. Tijessen, ed.); Fundamental Virology, 2nd Edition, vol. I & II (B. N. Fields and D. M. Knipe, eds.)

It is specific object of the present invention the use of compounds that interfere with the hedgehog signaling pathway for the manufacture of a medicament for preventing, inhibiting, and/or reversing ocular diseases related with the ocular neovascularization.

The compounds that interfere with the Hedgehog signaling pathway can be selected from the group comprising a small molecule, for example with a molecular weight of less than 2000 Daltons, protein, peptoid, and/or nucleic acid.

Small molecules, according to the present invention can be selected from the group consisting of steroidal alkaloids, compound A, SANT1, SANT2, SANT3, SANT4, Cur61414, Forskolin, tomatidine, AY9944, triparanol, compound B and functionally effective derivative thereof.

Steroidal alkaloids can be selected from the group consisting of cyclopamine or a functionally effective derivative thereof, KAAD-cyclopamine, jervine, aldosterone, androstane, androstene, androstenedione, androsterone, cholecalciferol, cholestane, cholic acid, corticosterone, cortisol, cortisol acetate, cortisone, cortisone acetate, deoxycorticosterone, digitoxigenin, ergocalciferol, ergosterol, estradiol-17-a, estradiol-17-β, estriol, estrane, estrone, hydrocortisone, lanosterol, lithocholic acid, mestranol, β-methasone, prednisone, pregnane, pregnenolone, progesterone, spironolactone, testosterone, triamcinolone and their derivatives.

In addition, small molecule can be represented by general formula (I) (U.S. patent application Ser. No. 20030022819)

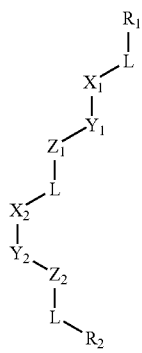

wherein, as valence and stability permit, $R_1$ and $R_2$, independently for each occurrence, represent H, lower alkyl, aryl (e.g., substituted or unsubstituted), aralkyl (e.g., substituted or unsubstituted, e.g., —($CH_2$)naryl), or heteroaryl (e.g., substituted or unsubstituted), or heteroaralkyl (e.g., substituted or unsubstituted, e.g., —($CH_2$)$_n$heteroaralkyl-); L, independently for each occurrence, is absent or represents —($CH_2$)$_n$-alkyl, -alkenyl-, -alkynyl-, —($CH_2$)$_n$alkenyl-, —($CH_2$)$_n$ alkynyl-, —($CH_2$)$_n$O($CH_2$)$_p$—, —($CH_2$)$_n$$NR_2$($CH2$)$_p$—, —($CH_2$)$_n$ S($CH_2$)$_p$—, —($CH_2$)$_n$ alkenyl ($CH_2$)$_p$—, —($CH_2$)$_n$ alkynyl($CH_2$)$_p$—, —O($CH_2$)$_n$—, —$NR_2$($CH_2$)$_n$—, or —S($CH_2$)$_n$—; $X_1$ and $X_2$ can be selected, independently, from —N($R_8$)—, —O—, —S—, —Se—, —N—N—, —ON—CH—, —($R_8$)N—N($R_8$)—, —ON($R_8$)—, a heterocycle, or a direct bond between L and $Y_1$ or $Y_2$, respectively; $Y_1$ and $Y_2$ can be selected, independently, from —C(═O)—, —C(═S)—, —S($O_2$)—, —S(O)—, —C(═NCN)—, —P(═O)($OR_2$)—, a heteroaromatic group, or a direct bond between $X_1$ and $Z_1$ or $X_2$ and $Z_2$, respectively; $Z_1$ and $Z_2$ can be selected, independently, from —N($R_8$)—, —O—, —S—, —Se—, —N—N—, —ON—CH—, —$R_8$N—$NR_8$—, —$ONR_8$—, a heterocycle, or a direct bond between $Y_1$ or $Y_2$, respectively, and L; $R_8$, independently for each occurrence, represents H, lower alkyl, —($CH_2$)naryl (e.g., substituted or unsubstituted), —($CH_2$)nheteroaryl (e.g., substituted or unsubstituted), or two $R_8$ taken together may form a 4-to 8-membered ring, e.g., with $X_1$ and $Z_1$ or $X_2$ and $Z_1$, which ring may include one or more carbonyls; p represents, independently for each occurrence, an integer from 0 to 10, preferably from 0 to 3; and n, individually for each occurence, represents an integer from 0 to 10, preferably from 0 to 5.

Small molecule can be also represented by general formula (II) (U.S. patent application Ser. No. 20030022819):

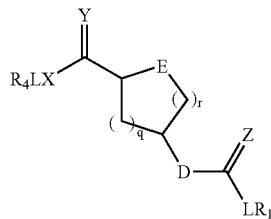

wherein, as valence and stability permit, $R_1$, $R_2$, $R_3$, and $R_4$, independently for each occurrence, represent H, lower alkyl, —($CH_2$)$_n$aryl (e.g., substituted or unsubstituted), or —($CH_2$)$_n$ heteroaryl (e.g., substituted or unsubstituted); L, independently for each occurrence, is absent or represents —($CH_2$)$_n$—, -alkenyl-, -alkynyl-, —($CH_2$)$_n$alkenyl-, —($CH_2$)$_n$ alkynyl-, —($CH_2$)$_n$O($CH_2$)$_p$—, —($CH_2$)$_n$$NR_8$ ($CH_2$)$_p$—, —($CH_2$)$_n$S($CH_2$)$_p$—, —($CH_2$)$_n$alkenyl($CH_2$)$_p$—, —($CH_2$)$_n$alkynyl($CH_2$)$_p$—, —O($CH_2$)$_n$—, —$NR_8$($CH_2$)$_n$—, or —S($CH_2$)$_n$; X and D, independently, can be selected from —N($R_8$)—, —O—, —S—, —($R_8$)N—N($R_8$)—, —ON($R_8$)—, or a direct bond; Y and Z, independently, can be selected from O or S; E represents O, S, or $NR_5$, wherein $R_5$ represents $LR_8$ or —(C—O) $LR_8$. $R_8$, independently for each occurrence, represents H, lower alkyl, —($CH_2$)$_n$aryl (e.g., substituted or unsubstituted), —($CH_2$)$_n$heteroaryl (e.g., substituted or unsubstituted), or two $R_8$ taken together may form a 4- to 8-membered ring; p represents, independently for each occurrence, an integer from 0 to 10, preferably from 0 to 3; n, individually for each occurrence, represents an integer from 0 to 10, preferably from 0 to 5; and q and r represent, independently for each occurrence, an integer from 0-2.

The nucleic acid is selected from the group consisting of (antisense) oligonucleotides, ribozymes, aptamers, and/or small interfering (ribo)nucleic acids.

Particularly, the nucleic acid can encode a polypeptide and is introduced into the eye by means of a viral vector, a non-viral vector and/or naked DNA.

The nucleic acid can be an isolated small interfering RNA comprising a sense RNA strand and an antisense RNA strand, wherein the sense and antisense RNA strands form an RNA duplex, and wherein the sense RNA strand comprises the nucleotide sequence SEQ ID NO:16 and the antisense RNA strand comprises the nucleotide sequence SEQ ID NO:15.

In addition, the nucleic acid can be an isolated small interfering RNA comprising a sense RNA strand and an antisense RNA strand, wherein the sense and antisense RNA strands form an RNA duplex, and wherein the sense RNA strand comprises the nucleotide sequence SEQ ID NO:17 and the antisense RNA strand comprises the nucleotide sequence SEQ ID NO:18.

The nucleic acid can be also an isolated small interfering RNA comprising a sense RNA strand and an antisense RNA strand, wherein the sense and antisense RNA strands form an RNA duplex, and wherein the sense RNA strand comprises the nucleotide sequence SEQ ID NO:19 and the antisense RNA strand comprises the nucleotide sequence SEQ ID NO:20.

Typically, the siRNA of the invention is administered to a mammalian subject at a concentration of about 10 to 200 mg/ml, or about 100 to 1,000 nM. Application can be performed either topically to the eye (topical instillation) in a volume from about 5 microliters to about 75 microliters, for example from about 7 microliters to about 50 microliters (in case of a mouse), or in a volume of about 50 microliters to 500 microliters, for example from about 100 microliters to about 250 microliters. Alternatively, the siRNA of the invention can be administered by intravitreal or subretinal injection in a volume of 1 microliter to about 5 microliters (in case of a mouse), or in a volume of about 300 microliters to 1,000 microliters (in case of a human). One of ordinary skill in the art will be able to determine the appropriate volume as a function of the subject to be treated and the route of administration.

Substance that interferes with the Hedgehog signaling pathway can be also a decoy protein which can be in a secreted form of the Hedgehog interacting protein 1 (Hip1) or a homologous protein.

The soluble Hip1 protein can be encoded in a transgene cassette of a gene transfer vector with the administration of said gene transfer vector to a mammalian subject resulting in the expression and secretion of soluble Hip1. Said gene transfer vector can be a recombinant adeno-associated viral vector.

The protein can be a mutant Hedgehog protein, an antibody homolog directed against patched and/or smoothened. Said antibody homolog can be a monoclonal antibody 5E1 or a monoclonal antibody that binds the same epitope as 5E1 (5E1, Developmental Studies Hybridoma Bank, Karen Jensen, Department of Biological Sciences, The University of Iowa, 007 Biology Building East, Iowa City, Iowa 52242, tel: (319)335-3826, fax: (319)335-2077.

The above-mentioned compounds can interfere with the different Hedgehog signaling, i.e. Sonic (Shh), Desert (Dhh) or Indian (Ihh) Hedgehog signaling and can interact by means of different mechanisms. Particularly, the compounds according to the present invention can interact with Hedgehog receptor, patched (Ptc), more particularly with the mammalian Hedgehog receptors Ptc1 and/or Ptc2, with the Hedgehog co-receptor smoothened (Smo), with the serine-threonine kinase fused (Fu) or with the transcription factor Gli1, Gli2 and/or Gli3.

Ocular diseases related with the ocular neovascularization that can be treated according to the present invention are represented by, for example, age-related macular degeneration, diabetic retinopathy, retinopathy of prematurity (ROP), neovascular glaucoma, retinal vein occlusion.

The medicament that can be used according to the present invention can be suitable for and/or administered by local administration, topical administration, systemic administration, intravitreal injection, subtretinal injection, intravitreal administration, intracavity injection, intra-arterial administration, intravenous administration, intramuscular administration, injection into tissue, injection into gaps in tissue or inhalation and/or nasal instillation. In addition, the compounds that interfere with the hedgehog signaling pathway can be associated with agents modulating cAMP level.

The practice of the present invention will employ, unless otherwise indicated, conventional methods of virology, chemistry, microbiology, molecular biology and recombinant DNA techniques within the skill of the art. Such techniques are explained fully in the literature; see, e.g., Sambrook, et al. Molecular Cloning: A Laboratory Manual (Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, vol. I & II (P. Tijessen, ed.); Fundamental Virology, 2nd Edition, vol. I & II (B. N. Fields and D. M. Knipe, eds.)

3.1 Definitions

In describing the present invention, the following terms will be employed, and are intended to be defined as indicated below.

For purposes of this invention, the "vascular development" comprises at least two steps: "vasculogenesis" and physiological angiogenesis. The term "vasculogenesis" refers to process, where endothelial cells form a primary tubular network, whereas "angiogenesis" refers to a process, in which vessel size and structure are modified, and branching occurs to insure that all cells are supplied with sufficient nutrients. Thus, "angiogenesis" is defined as any alteration of an existing vascular bed or the extension of existing vasculature which benefits tissue perfusion.

For purposes of this invention, pathological (abnormal) vasculogenesis is referred to as "neovascularization". Neovascularization—in a more narrow definition—is a form of pathologic, abnormal vasculogenesis in the eye ("ocular neovascularization"). It leads to visual loss through increased vascular permeability leading to retinal oedema, (b) vascular fragility resulting in haemorrhage, or fibro-vascular proliferation with tractional and rhegmatogenous retinal detachment. Choroidal neovascularization is used synonymously with ocular neovascularization. Furthermore, for purposes of this invention, angiogenesis can be either physiological or pathological. Furthermore, for purposes of this invention, "angiogenesis" can be either physiological or pathological.

For purposes of this invention, the term "Hedgehog" is used to refer generically to any member of the Hedgehog family, including sonic, indian, desert and tiggy winkle. The term may be used to indicate a protein or gene.

For purposes of this invention, the term "Hedgehog transduction pathway" are all used to refer to the chain of events normally mediated by Hedgehog, smoothened, ptc, and gli, among others, and resulting in a changes in gene expression and other phenotypic changes typical of Hedgehog activity. The Hedgehog pathway can be activated even in the absence of a Hedgehog protein by activating a downstream component. For example, overexpression of smoothened will activate the pathway in the absence of Hedgehog. gli and ptc gene expression are indicators of an active Hedgehog signaling pathway.

For purposes of this invention, the term "Hedgehog antagonist" refers to an agent that potentiates or recapitulates the bioactivity of patched, such as to repress transcription of target genes. In other words: A hedgehog antagonist is a substance that interferes with the Hedgehog signaling pathway. The term "Hedgehog antagonist" as used herein refers not only to any agent that may act by directly inhibiting the normal function of the Hedgehog protein, but also to any agent that inhibits the Hedgehog signalling pathway, and thus recapitulates the function of ptc. A Hedgehog antagonist may be a small molecule, an antibody (including but not restricted to: a diabody, single chain antibody, monoclonal antibody, IgG, IgM, IgA, IgD, IgE, or an antibody fragment comprising at least one pair of variable regions), an antisense nucleic acid, PNA or ribozyme, RNAi construct, aptamer, peptoid, or a mutant Hedgehog protein that can disrupt or inhibit Hedgehog signaling. An antibody may be directed to a protein encoded by any of the genes in the Hedgehog pathway, including sonic, indian or desert Hedgehog, smoothened, ptc-1, ptc-2, gli-1, gli-2, gli-3, etc. In most cases, the antibody would inhibit the activity of the target protein, but in the case of patched, such an antibody would be an activator of patched. An antisense nucleic acid would likewise decrease production of a protein encoded by any of the genes in the Hedgehog pathway, with the exception of patched or other genes encoding negative regulators of the Hedgehog signaling pathway.

A preferred antagonist has at least the following properties: (i) the isolated protein binds the receptor patched-1 with an affinity that may be less than, but is preferably at least the same as, the binding of mature Hedgehog protein to patched-1; and (ii) the isolated protein blocks alkaline phosphatase (AP) induction by mature Hedgehog protein when tested in an in vitro CH310T ½ cell-based AP induction assay. Antagonists of the invention may also have the additional properties of being (iii) unable to induce ptc-1 and gli-1expression. Persons having ordinary skill in the art can easily test any putative Hedgehog antagonist for these properties. In particular, the mouse embryonic fibroblast line C3H10T I/2 is a mesenchymal stem cell line that is Hedgehog responsive. Hedgehog treatment of the cells causes an upregulation of gli-1 and patched-1 (known indicators of Hedgehog dependent signaling) and also causes induction of alkaline phosphatase activity, an indicator that the cells have differentiated down the chondrocyte/bone osteoblast lineage.

For purposes of this invention, the term "protein" means a polypeptide (native (i.e., naturally-occurring) or mutant), oligopeptide, peptide, or other amino acid sequence. As used herein, "protein" is not limited to native or full-length proteins, but is meant to encompass protein fragments having a desired activity or other desirable biological characteristics, as well as mutants or derivatives of such proteins or protein fragments that retain a desired activity or other biological characteristic—including peptoids with a nitrogen based backbone. Mutant proteins encompass proteins having an amino acid sequence that is altered relative to the native protein from which it is derived, where the alterations can include amino acid substitutions (conservative or non-conservative), deletions, or additions (e.g., as in a fusion protein). "Protein" and "polypeptide" are used interchangeably herein without intending to limit the scope of either term.

For purposes of this invention, "amino acid" refers to a monomeric unit of a peptide, polypeptide, or protein. There are twenty amino acids found in naturally occurring peptides, polypeptides and proteins, all of which are L-isomers. The term also includes analogs of the amino acids and D-isomers of the protein amino acids and their analogs.

For purposes of the present invention, "soluble" is intended to mean a chimeric and/or modified receptor protein that is not fixed to the surface of cells via a transmembrane domain. As such, soluble forms of the chimeric binding proteins of the present invention, while capable of binding to and inactivating its ligand, do not comprise a transmembrane domain and thus generally do not become associated with the cell membrane of cells in which the molecule is expressed. A soluble form of the receptor exerts an inhibitory effect on the biological activity of the ligand protein by binding to its ligand, thereby preventing it from binding to its natural receptors present on the surface of target cells.

For purposes of this invention, by "DNA" is meant a polymeric form of desoxyribonucleotides (adenine, guanine, thymine, or cytosine) in double-stranded or single-stranded form, either relaxed and supercoiled, either linear circular. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the non-transcribed strand of DNA (i.e., the strand having the sequence homologous to the mRNA). The term captures molecules that include the four bases adenine, guanine, thymine, or cytosine, as well as molecules that include base analogues which are known in the art.

For purposes of this invention, "polynucleotide" as used herein means a polymeric form of nucleotides of any length, either ribonucleotides or desoxyribonucleotides. This term refers only to the primary structure of the molecule. Thus, the term includes double- and single-stranded DNA, as well as, double- and single-stranded RNA. It also includes modifications, such as methylation or capping, and unmodified forms of the polynucleotide.

For the purpose of describing the relative position of nucleotide sequences in a particular nucleic acid molecule throughout the instant application, such as when a particular nucleotide sequence is described as being situated "upstream," "downstream," "5'," or "3'" relative to another sequence, it is to be understood that it is the position of the sequences in the non-transcribed strand of a DNA molecule that is being referred to as is conventional in the art.

For purposes of this invention, a "gene sequence" or "coding sequence" or "protein coding sequence" or "open reading frame" or a sequence which "encodes" a particular protein, is a nucleic acid composition which is transcribed into RNA (in the case of DNA) and potentially translated (in the case of mRNA) into a polypeptide in vitro or in vivo when placed under the control of appropriate regulatory sequences. The boundaries of the gene are determined by a start codon at the 5' (amino) terminus and potentially a translation stop codon at the 3' (carboxy) terminus. A gene sequence can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the protein coding sequence.

For purposes of this invention, by the term "transgene" is meant a nucleic acid composition made out of DNA, which encodes a peptide, oligopeptide or protein. The transgene may be operatively linked to regulatory components in a manner which permits transgene transcription, translation and/or ultimately directs expression of a product encoded by the nucleic acid composition in the host cell, e.g., the transgene is placed into operative association with a promoter and enhancer elements, as well as other regulatory sequences, such as introns or polyA sequences, useful for its regulation. The composite association of the transgene with its regulatory sequences is referred to herein as a "minicassette" or "minigene". Minicasssettes or minigenes in their entirety are also nucleic acid compositions. The exact nucleic acid composition will depend upon the use to which the resulting nucleic acid transfer vector will be put and is known to the artisan (Sambrook 1989, Lodish et al. 2000). When taken up by a target cell, the nucleic acid composition may remain present in the cell as a functioning extrachromosomal molecule, or it may integrate into the cell's chromosomal DNA, depending on the kind of transfer vector used.

For purposes of this invention, "heterologous" as it relates to nucleic acid compositions denotes sequences that are not normally joined together. Thus, a "heterologous" region of a nucleic acid composition is a segment of nucleic acid within or attached to another nucleic acid composition that is not found in association with the other molecule in nature. For example, a heterologous region of a nucleic acid composition could include a coding sequence flanked by sequences not found in association with the coding sequence in nature. Another example of a heterologous coding sequence is a construct where the coding sequence itself is not found in nature (e.g., synthetic sequences having codons different from the native gene). Allelic variation or naturally occurring mutational events do not give rise to heterologous DNA, as used herein.

For purposes of this invention, "homology" or "homologous" refers to the percent homology between two polynucleotide or two polypeptide moiety. The correspondence between the sequence from one moiety to another can be determined by techniques known in the art. Two DNA or two polypeptide sequences are "substantially homologous" to each other when at least about 80%, preferably at least about 90%, and most preferably at least about 95% of the nucleotides or amino acids match over a defined length of the molecules, as determined using methods in the art.

The techniques for determining amino acid sequence homology are well-known in the art. In general, "homology" means the exact amino acid to amino acid comparison of two or more polypeptides at the appropriate place, where amino acids are identical or possess similar chemical and/or physical properties such as charge or hydrophobicity. A so-termed "percent homology" then can be determined between the compared polypeptide sequences. The programs available in the Wisconsin Sequence Analysis Package (available from Genetics Computer Group, Madison, Wis.), for example, the GAP program, are capable of calculating homologies between two polypeptide sequences. Other programs for determining homology between polypeptide sequences are known in the art.

Homology for polynucleotides is determined essentially as follows: Two polynucleotides are considered to be "substantially homologous" to each other when at least about 80%, preferably at least about 90%, and most preferably at least about 95% of the nucleotides match over a defined length of the molecules, when aligned using the default parameters of the search algorithm BLAST 2.0. The BLAST 2.0 program is publicly available.

Alternatively, homology for polynucleotides can be determined by hybridization experiments. As used herein, a nucleic acid sequence or fragment (such as for example, primers or probes), is considered to selectively hybridize to a sequence 1, thus indicating "substantial homology", if such a sequence is capable of specifically hybridizing to the sequence 1 or a variant thereof or specifically priming a polymerase chain reaction: (i) under typical hybridization and wash conditions, such as those described, for example, in Maniatis, (Molecular Cloning: A Laboratory Manual, 2nd Edition, 1989) where preferred hybridization conditions are those of lesser stringency and more preferred, higher stringency; or (ii) using reduced stringency wash conditions that allow at most about 25-30% basepair mismatches, for example, 2.times.SSC, 0.1% SDS, at room temperature twice, for 30 minutes each; then 2.times.SSC, 0.1% SDS, 37 C, once for 30 minutes; the 2.times.SSC at room temperature twice, 10 minutes each or (iii) under standard PCR conditions or under "touch-down" PCR conditions such as described by [98]).

For purposes of this invention, the term "cell" means any prokaryotic or eukaryotic cell, either ex vivo, in vitro or in vivo, either separate (in suspension) or as part of a higher structure such as—but not limited to—organs or tissues.

For purposes of this invention, the term "host cell" means a cell that can be transduced and/or transfected by an appropriate gene transfer vector. The nature of the host cell may vary from gene transfer vector to gene transfer vector.

For purposes of this invention, by the term "a Therapeutic of this invention" is meant a substance that interferes with Hedgehog signaling in general, and Shh signaling in particular, resulting in prevention, inhibition, and/or reversion of ocular neovascularization.

For purposes of this invention, "treatment" refers to prophylaxis and/or therapy.

"Pharmaceutically effective" levels are levels sufficient to achieve a physiologic effect in a human or veterinary subject, which effect may be therapeutic or prophylactic.

For purposes of this invention, by "mammalian subject" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

For purposes of this invention, the terms "individual" or "subject" or "patient" as used herein refer to vertebrates, particularly members of the mammalian species and include but are not limited to domestic animals, sports animals, primates and humans; more particularly the term refer to humans.

For purposes of this invention, "mesenchymal cells" are defined as cells of mesenchymal origin including fibroblasts, stromal cells, smooth muscle cells, skeletal muscle cells, cells of osteogenic origin such as chondrocytes, cells of hemaeopoietic origin such as monocytes, macrophages, lymphocytes, granulocytes and cells of adipose origin such as adipocytes.

For purpose of this invention, a "Hedgehog therapeutic", whether it is a Hedgehog agonist or Hedgehog antagonist is said to have "therapeutic efficacy" in modulating neovascularization, and an amount of the therapeutic is said to be a "angiogenic modulatory amount", if administration of that amount of the therapeutic is sufficient to cause a significant modulation (i.e., increase or decrease) in angiogenic activity when administered to a subject (e.g., an animal model or human patient) needing modulation of angiogenesis.

For purposes of this invention, a "substance that interferes with the Hedgehog signaling pathway" or a "Hedgehog signaling interfering substance" is a Hedgehog therapeutic with Hedgehog-antagonistic function. Interference can be accomplished in different ways, whereas one substance can exert one or more interfering mechanisms: The substance can interfere with the Hedgehog signaling pathway in general, and the Shh pathway in particular by (1) De-activating the Hedgehog receptor or inhibiting its activity;

(2) Inhibiting activity of the Hedgehog protein;

(3) Coating, or binding to, a Hedgehog protein on the surface of a Hedgehog bearing or secreting cell with sufficient specificity to de-activate or inhibit a Hedgehog-ligand/Hedgehog interaction, e.g., the Hedgehog/patched interaction;

(4) Coating, or binding to, a Hedgehog protein on the surface of a Hedgehog-bearing or secreting cell with sufficient specificity to modify, and preferably to de-activate or inhibit, transduction of a Hedgehog-mediated signal e.g., Hedgehog/patched, smoothened, fused, or gli-mediated signaling;

(5) Coating, or binding to, a Hedgehog receptor or coreceptor (e.g., patched or smoothened) in or on cells with sufficient specificity to de-activate or inhibit the Hedgehog/patched interaction;
(6) Coating, or binding to, a Hedgehog receptor or co-receptor (e.g., patched or smoothened) in or on cells with sufficient specificity to modify, and preferably to de-activate or inhibit transduction of Hedgehog receptor mediated Hedgehog signaling, e.g., patched-mediated Hedgehog signaling;
(7) Exerting RNA interference with an RNA that encodes a component of the Hedgehog signaling pathway Moreover, more than one a substance that interferes with the Hedgehog signaling pathway can be administered to a patient, e.g., an agent that binds to Hedgehog can be combined with an agent that binds to Patched. Moreover, a Hedgehog therapeutic is an "antagonist" if it modulates ocular neovascularization in such a way as to inhibit, decelerate, reverse or otherwise slow ocular neovascularization, regardless of the mode of action of such therapeutic. For example, antagonist molecules may be antibody homologs, certain fragments of Hedgehog, small interfering RNAs, peptoids, aptamers, or small organic molecules that may be administered and modulate Hedgehog binding sites on cells.

For purposes of this invention, the term "antibody homolog" includes intact antibodies consisting of immunoglobulin light and heavy chains linked via disulfide bonds. The term "antibody homolog" is also intended to encompass a Hedgehog therapeutic comprising one or more polypeptides selected from immunoglobulin light chains, immunoglobulin heavy chains and antigen-binding fragments thereof which are capable of binding to one or more antigens (i.e., Hedgehog, Patched, and/or Smo). The component polypeptides of an antibody homolog composed of more than one polypeptide may optionally be disulfide-bound or otherwise covalently crosslinked. Accordingly, therefore, "antibody homologs" include intact immunoglobulins of types IgA, IgG, IgE, IgD, IgM (as well as subtypes thereof), wherein the light chains of the immunoglobulin may be of types kappa or lambda or portions of intact antibodies that retain antigen-binding specificity, for example, Fab fragments, Fab' fragments, F(ab')2 fragments, F(v) fragments, heavy chain monomers or dimers, light chain monomers or dimers, dimers consisting of one heavy and one light chain, and the like. An "antibody homolog" also refers to monoclonal antibodies, chimeric antibodies, single-chain antibodies, intrabodies, humanized monoclonal antibodies and antibodies linked to other molecules.

For purposes of this invention, a "humanized antibody homolog" is an antibody homolog, produced by recombinant DNA technology, in which some or all of the amino acids of a human immunoglobulin light or heavy chain that are not required for antigen binding have been substituted for the corresponding amino acids from a non-human mammalian immunoglobulin light or heavy chain.

For purposes of this invention, a "human antibody homolog" is an antibody homolog in which all the amino acids of an immunoglobulin light or heavy chain (regardless of whether or not they are required for antigen binding) are derived from a human source.

By "not substantially cross react" is meant that the antibody has a binding affinity for a non-homologous protein which is at least one order of magnitude, more preferably at least 2 orders of magnitude, and even more preferably at least 3 orders of magnitude less than the binding affinity of the antibody for the protein or proteins for which the antibody is immunospecific.

For purposes of this invention, the term "gene therapy" means the transfer of nucleic acid compositions into cells of a multicellular eukaryotic organism, be it in vivo, ex vivo or in vitro (see also [57] [58]). The term "gene therapy" should not be limited to the purpose of correcting metabolic disorders, but be interpreted more as a technical term for the transfer of nucleic acid compositions for therapeutic purposes in general, independent of a specific therapeutic purpose. Therefore, the term "gene therapy" would include—without limitation—correction of metabolic disorders, cancer therapy, vaccination, monitoring of cell populations, cell expansion, stem cell manipulation etc. by means of transfer of nucleic acid compositions.

For purposes of this invention, "transfection" is used to refer to the uptake of nucleic acid compositions by a cell. A cell has been "transfected" when an exogenous nucleic acid composition has crossed the cell membrane. A number of transfection techniques are generally known in the art. See, e.g., [59, 60], Sambrook et al. (1989) Molecular Cloning, a laboratory manual, Cold Spring Harbor Laboratories, New York, Davis et al. (1986) Basic Methods in Molecular Biology, Elsevier, and [61]. Such techniques can be used to introduce one or more nucleic acid compositions, such as a plasmid vector and other nucleic acid molecules, into suitable host cells. The term refers to both stable and transient uptake of the genetic material. For purposes of this invention, "transduction" is a special form of "transfection" via a viral vector.

For purposes of this invention, "transduction" denotes the delivery of a nucleic acid composition to, into or within a recipient cell either in vivo, in vitro or ex vivo, via a virus or viral vector, such as via a recombinant AAV virion. Transduction is a special form of transfection, i.e., the term transfection includes the term transduction.

For purposes of this invention, by "vector", "transfer vector", "gene transfer vector" or "nucleic acid composition transfer vector" is meant any element, such as a plasmid, phage, transposon, cosmid, chromosome, virus, virion, etc., which is capable of transferring and/or transporting a nucleic acid composition to a host cell, into a host cell and/or to a specific location and/or compartment within a host cell. Thus, the term includes cloning and expression vehicles, as well as viral and non-viral vectors and potentially naked or complexed DNA. However, the term does not include cells that produce gene transfer vectors such as retroviral packaging cell lines.

For purposes of this invention, by "recombinant virus", "recombinant virion", "recombinant vector" or "recombinant viral vector" is meant a virus that has been genetically altered, e.g., by the addition or insertion of a heterologous nucleic acid composition into the particle.

For purposes of this invention, the term "RNA interference" or "RNAi" is broadly defined and includes all posttranscriptional and transcriptional mechanisms of RNA mediated inhibition of gene expression, such as those described in P. D. Zamore Science 296, 1265 (2002). RNA interference is mediated by double-stranded RNA (dsRNA), which can induce many different epigenetic gene-silencing processes in eukaryotes, including the degradation of homologous mRNAs—a process called RNA interference (RNAi) in animals and post-transcriptional gene silencing (PTGS) in plants. RNA interference (RNAi) has first been discovered in 1998 by Andrew Fire and Craig Mello in C. elegans, confirming former studies of PGTS in plants [62]. It now seems to be a ubiquitous mechanism—also applicable to humans [63-73]. Double stranded RNA has been shown to inhibit gene expression of genes having a complementary sequence through a process termed RNA interference (see, for example, Hammond et al. Nat. Rev. Genet. 2:110-119 (2001)).

For purposes of this invention, the term "small interfering RNA" or "siRNA" as used herein means short interfering RNA which is a double-stranded RNA complex that is less than 30 base pairs (i.e., 60 nucleotides or bases) and preferably 21-25 base pairs (i.e., 42-50 bases or nucleotides) in length. More generally, double-stranded RNA that is responsible for inducing RNAi is termed interfering RNA. Thus, a "small interfering RNA" or "siRNA" is a double-stranded RNA complex that is capable of decreasing the expression of a gene with which it shares homology. The region of the gene or other nucleotide sequence over which there is homology is known as the "RNAi target region", "target region", "RNAi target sequence" or "target sequence".

In one embodiment the siRNA may be a "hairpin" or stem-loop RNA molecule, comprising a sense region, a loop region and an antisense region complementary to the sense region and thus capable of forming an RNAi inducing dsRNA complex. In other embodiments the siRNA comprises two distinct RNA molecules that are non-covalently associated to form a dsRNA complex.

For purposes of this invention, the term "RNAi expression cassette" as used herein means a nucleic acid composition which encodes one or more RNA molecules which are capable of forming a double-stranded RNA complex and thus are capable of inducing RNA interference.

The design of the RNAi expression cassette does not limit the scope of the invention. Different strategies to design an RNAi expression cassette can be applied, and RNAi expression cassettes based on different designs will be able to induce RNA interference in vivo. (Although the design of the RNAi expression cassette does not limit the scope of the invention, some RNAi expression cassette designs are included in the detailed description of this invention and below.) One of skill in the art will be able to choose among different designs without undue effort.

Features common to all RNAi expression cassettes are that they comprise an RNA coding region which encodes one or more RNA molecules. After or during RNA expression from the RNAi expression cassette, a double-stranded RNA complex may be formed by either a single, self-complementary RNA molecule (intramolecular formation) or two complementary RNA molecules (intermolecular formation). Formation of the dsRNA complex may be initiated either inside or outside the nucleus. The dsRNA complex will be capable of inducing RNA interference either directly or indirectly.

In some embodiments, the RNAi inducing double-stranded RNA complex (encoded by the RNAi expression cassette(s)) comprises a first RNA portion capable of hybridizing under physiological conditions to at least a portion of an mRNA molecule (the RNAi target sequence of the RNAi target mRNA of the RNAi target gene), and a second RNA portion wherein at least a part of the second RNA portion is capable of hybridizing under physiological conditions to the first portion. Preferably the first and second portions are part of the same RNA molecule and are capable of hybridization at physiological conditions, such as those existing within a cell and upon hybridization the first and second portions form a double-stranded RNA complex. For example, the RNAi inducing double-stranded RNA complex (encoded by the RNAi expression cassette(s)) is formed by a linear RNA molecule, which RNA comprises a first portion capable of hybridizing to at least a portion of an mRNA molecule and a second portion wherein at least part of the second portion is capable of hybridizing to the first portion to form a hairpin dsRNA complex. Thus, in some embodiments, when introduced into a cell via rAAV gene transfer, expression of the RNAi expression cassette gives rise to a single RNA molecule capable of forming intramolecularly an RNAi inducing dsRNA complex. However, it will be understood from the following description that more than one rAAV genome or rAAV vector or RNAi expression cassette or RNA coding region may be introduced into a cell, either simultaneously or sequentially via rAAV mediated gene transfer, to give rise to two or more RNA molecules capable of forming intermolecularly an RNAi-inducing dsRNA complex. Typically, the two RNA sequences capable of forming a dsRNA complex, whether intra- or intermolecularly, are at least in part sense and at least in part antisense sequences of a gene or nucleic acid sequence whose expression is to be down-regulated or decreased.

In the preferred embodiment the RNAi expression cassette comprises at least one RNA coding region. In other embodiments, the RNAi expression cassette comprises two or more RNA coding regions. The RNAi expression cassette also preferably comprises at least one RNA Polymerase III promoter. The RNA Polymerase III promoter is operably linked to the RNA coding region, and the RNA coding region can also be linked to a termination sequence (terminator). In addition, more than one RNA Polymerase III promoters may be incorporated.

In certain embodiments the invention employs ribozyme-containing RNA molecules—encoded by the RNAi expression cassette—to generate dsRNA complexes, thereby overcoming certain known difficulties associated with generating dsRNA such as the removal of polyadenylation signals. In other embodiments the invention is based on the ability of a portion of the RNA molecule to encode an RNA or protein that enhances specific activity of dsRNA. One example of this specific activity enhancing portion of the RNA molecule is a portion of the molecule encoding the HIV Tat protein to inhibit the cellular breakdown of dsRNA complexes. Such a portion is additionally useful in treating disorders such as HIV infection.

For purposes of this invention, the term "RNA expression product" or "RNA product" refers to the RNA molecule or RNA transcript transcribed (synthesized) from an RNAi expression cassette.

The term "target mRNA" or "RNAi target mRNA" refers to any mRNA whose expression in the host is to be reduced. The RNAi target mRNA is the RNA transcript of the (RNAi) target gene.

The terms "double-stranded RNA complex" or "dsRNA complex" as used herein are equivalent, and each shall mean a complex formed either (a) by two linear molecules of RNA, wherein at least a portion of the sequence of one molecule is complementary to, and is capable of or has hybridized to, at least a portion of the sequence of the other RNA molecule, or (b) by two portions of a linear RNA molecule which are complementary to, and are capable of or have therefore hybridized to, each other. The dsRNA complex is generated by the RNA expression product(s) of the RNAi expression cassette(s) and is able to mediate either directly or indirectly RNA interference, thus mediating down-regulation of the expression of the RNAi target gene.

In certain embodiments, said double-stranded RNA complex for down-regulating expression of a mammalian gene comprises (i) a first nucleotide sequence that hybridizes under stringent conditions to a nucleotide sequence of at least one mammalian gene and (ii) a second nucleotide sequence which is complementary to said first nucleotide sequence. In a subgroup of those embodiments, an RNA loop connects the first with the second nucleotide sequence.

A dsRNA complex comprising a nucleotide sequence identical to a portion of the RNAi target gene is preferred for inhibition. RNA sequences with insertions, deletions, and single point mutations relative to the RNAi target sequence have also been found to be effective for inhibition. Thus, sequence identity may be optimized by alignment algorithms known in the art and calculating the percent difference between the nucleotide sequences. Alternatively, the RNA duplex region of the dsRNA complex may be defined functionally as a nucleotide sequence that is capable of hybridizing with a portion of the target gene transcript.

An example for a dsRNA complex are siRNAs. RNAi-inducing dsRNA complexes based on siRNAs are described [74] [75] [76]. The dsRNA complex is generally at least about 15 base pairs in length and is preferably about 15 to about 30 base pairs in length. However, a significantly longer dsRNA complex can be used effectively in some organisms. In a more preferred embodiment, the dsRNA complex is between about 19 and 22 base pairs in length. The dsRNA complex is preferably identical to the target nucleotide sequence over this region. When the gene to be down-regulated is in a family of highly conserved genes, the sequence of the duplex region can be chosen with the aid of sequence comparison to target only the desired gene. On the other hand, if there is sufficient identity among a family of homologous genes within an organism, a duplex region can be designed that would down regulate a plurality of genes simultaneously. The RNA duplexes may be flanked by single stranded regions on one or both sides of the duplex. For example, in the case of the hairpin, the single stranded loop region would connect the duplex region at one end.

For purposes of this invention, the term "RNA duplex" or "RNA duplex region" means the part of the dsRNA complex that is homologous and/or complementary to the RNAi target region. In certain embodiments, the RNA duplex might comprise the whole dsRNA complex. The RNA duplex is substantially homologous and/or complementary (typically at least about 80% identical, more preferably at least about 90% identical) in sequence to the RNAi target sequence of the gene targeted for down regulation via RNA interference.

For purposes of this invention, the term "Nucleic Acid Ligand" as used herein is a non-naturally occurring nucleic acid having a desirable action on a target. A nucleic acid ligand is also referred to as an "aptamer" herein. A desirable action includes, but is not limited to, binding of the target, catalytically changing the target, reacting with the target in a way which modifies/alters the target or the functional activity of the target, covalently attaching to the target as in a suicide inhibitor, and facilitating the reaction between the target and another molecule. In the preferred embodiment, the desirable action is specific binding to a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

For purposes of this invention, the term "SELEX" refers to a methodology involving the combination of selection of nucleic acid ligands which interact with a target in a desirable manner, for example binding to a protein, with amplification of those selected nucleic acids [77-79]. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to obtain nucleic acid ligands to components of the Hedgehog signaling pathway.

For purposes of this invention, the term "aliphatic group" refers to a straight-chain, branched-chain, or cyclic aliphatichydrocarbon group and includes saturated and unsaturated aliphatic groups, such as an alkyl group, analkenyl group, and an alkynyl group.

For purposes of this invention, the terms "alkenyl" and "alkynyl" refer to unsaturated aliphatic groups analogous in length and possible substitution to the alkyls described above, but that contain at least one double or triple bond, respectively.

For purposes of this invention, the terms "alkoxyl" or "alkoxy" as used herein refers to an alkyl group, as defined above, having anoxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—R8, where m and R8 are described above.

For purposes of this invention, the term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone.

Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate),an alkoxyl, a phosphoryl, a phosphate, a phosphonate, a phosphinate, an amino, an amido, an amidine, animine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well asethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

Unless the number of carbons is otherwise specified, "lower alkyl" as used herein means an alkylgroup, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

For purposes of this invention, the term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R8, wherein m and R8 are defined above. Representative alkylthio groups include methylthio, ethylthio, and the like.

For purposes of this invention, the term "aralkyl", as used herein, refers to an alkyl group substituted with an aryl group (e.g., anaromatic or heteroaromatic group).

For purposes of this invention, the term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

For purposes of this invention, the term "heteroatom" as used herein means an atom of any element other than carbon or hydrogen. Preferred heteroatoms are boron, nitrogen, oxygen, phosphorus, sulfur and selenium.

For purposes of this invention, the terms "heterocyclyl" or "heterocyclic group" refer to 3-to 10-membered ring structures, more preferably 3- to 7-membered rings, whose ring structures include one to four heteroatoms. Heterocycles can also be polycyclic. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine,phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

For purposes of this invention, the term, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

For purposes of this invention, the terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R8, m and R8 being defined above.

For purposes of this invention, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

For purposes of this invention, the definition of each expression, e.g., alkyl, m, n, etc. when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, ptoluenesulfonateester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

For purposes of this invention, the chemical of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds that can be substituted or unsubstituted.

3.2 General Methods

The present invention relates to methods of preventing, inhibiting, and/or reversing ocular neovascularization in a mammalian subject comprising administering to the subject a therapeutically effective amount of a substance that interferes with the Hedgehog signaling pathway. Ocular neovascularization is a major cause of blindness in developed countries. It is causally involved in many ocular diseases including age-related macular degeneration, (proliferative) diabetic retinopathy, neovascular glaucoma, retinal vein occlusion or retinopathy of prematurity (ROP). Current treatments are of limited efficacy and associated with significant adverse effects, reflecting the high unmet need in those disease areas.

The practice of the present invention will employ, unless otherwise indicated, conventional methods of virology, chemistry, microbiology, molecular biology and recombinant DNA techniques within the skill of the art. Such techniques are explained fully in the literature; see, e.g., Sambrook, et al. Molecular Cloning: A Laboratory Manual (Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, vol. I & II (P. Tijessen, ed.); Fundamental Virology, 2nd Edition, vol. I & II (B. N. Fields and D. M. Knipe, eds.)

Numerous experimental methods are relevant to this invention or experiments leading thereto, which are within routine skill in the art. These include: methods for isolating nucleic acid molecules, including, for example, phenol chloroform extraction, quick lysis and capture on columns ([80]; U.S. Pat. No. 5,582,988); methods of detecting and quantitating nucleic acid molecules; methods of detecting and quantitating catalytic nucleic acid activity; methods of amplifying a nucleic acid sequence including, for example, PCR, SDA and TMA (also known as (SSR) [U.S. Pat. Nos. 4,683,202; 4,683,195; 4,000,159; 4,965,188; 5,176,995]; and methods of determining whether a catalytic nucleic acid molecule cleaves an amplified nucleic acid segment including, by way of example, polyacrylamide gel electrophoresis and fluorescence resonance energy transfer (FRET) [[81]; PCT International Publication No. WO 94/29481].

Certain compounds of the present invention may exist in particular geometric or stereoisomeric forms. The present invention contemplates all such compounds, including cis- and trans-isomers, R— and S enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to inhibit Hedgehog signaling), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

3.2.1 Small Molecule Inhibitors

Small molecule antagonists of Hedgehog signaling have been described extensively in prior art. Formulas and methods of making the compositions are described in detail in the following U.S. patents and U.S. patent applications the specifications of which are expressly incorporated by reference herein: U.S. patent applications Ser. Nos. 20040110663 Dudek et al.: Hedgehog antagonists, methods and uses related thereto U.S. patent application Ser. No. 20040060568 Dudek et al.: Hedgehog antagonists, methods and uses related thereto U.S. patent application Ser. No. 20030022819 Ling et al.: Angiogenesis-modulating compositions and uses.

To summarize: In some embodiments of the present invention, a Hedgehog antagonist may be a small organic molecule. Such a small organic molecule may antagonize Hedgehog signal transduction via an interaction with but not limited to Hedgehog, patched (ptc), gli, and/or smoothened. It is, therefore, specifically contemplated that these small molecules which interfere with aspects of Hedgehog, ptc, or smoothened signal transduction activity will likewise be capable of inhibiting ocular neovascularization.

Thus, it is contemplated that in certain embodiments, these compounds may be useful for inhibiting Hedgehog activity. In preferred embodiments, the subject inhibitors are organic molecules having a molecular weight less than 2500 kD, more preferably less than 1500 kD, and even more preferably less than 750 kD, and are capable of antagonizing Hedgehog signaling, preferably specifically in target cells.

In certain preferred embodiments, the subject inhibitors inhibit Hedgehog-mediated signal transduction with an IC50 of 1 mM or less, more preferably of 1 µM or less, and even more preferably of 1 nM or less. Moreover, the subject methods can be performed on cells that are provided in culture (in vitro), or on cells in a whole animal (in vivo).

Hedgehog antagonists include AY9944, triparanol, jervine, cyclopamine and tomatidine, compound A and compound B (U.S. patent application Ser. No. 09/977,864).

In some embodiments, steroidal alkaloids are used to interfere with Hedgehog signaling. Steroidal alkaloids have a fairly complex nitrogen-containing nucleus. Two exemplary classes of steroidal alkaloids for use in the subject methods are the Solanum type and the Veratrum type. The above notwithstanding, in a preferred embodiment, the methods and compositions of the present invention make use of compounds having a steroidal alkaloid ring system of cyclopamine.

There are more than 50 naturally occurring veratrum alkaloids including veratramine, cyclopamine, cycloposine, jervine, and muldamine occurring in plants of the Veratrum spp. The Zigadenus spp., deathcamas, also produces several veratrum-type of steroidal alkaloids including zygacine. In general, many of the veratrum alkaloids (e.g., jervine, cyclopamine and cycloposine) consist of a modified steroid skeleton attached spiro to a furanopiperidine. Some veratrum-type alkaloids are depicted in FIG. 1.

An example of the Solanum type is solanidine. This steroidal alkaloid is the nucleus (i.e., aglycone) for two important glycoalkaloids, solanine and chaconine, found in potatoes. Other plants in the Solanum family including various nightshades, Jerusalem cherries, and tomatoes also contain solanum-type glycoalkaloids. Glycoalkaloids are glycosides of alkaloids. A typical solanum-type alkaloid is depicted in FIG. 2 (Solanidine).

Another class of smoothened antagonists can be based on the veratrum-type steroidal alkaloids resembling verticine and zygacine, or unsaturated forms thereof and/or seco-, noror homo-derivatives thereof.

Based on these structures, and the possibility that certain unwanted side effects can be reduced by some manipulation of the structure, a wide range of steroidal alkaloids is contemplated as potential smoothened antagonists for use in the subject method.

In certain embodiments, the subject antagonists can be chosen on the basis of their selectively for the smoothened pathway. This selectivity can be for the smoothened pathway versus other steroid-mediated pathways (such as testosterone or estrogen mediated activities), as well as selectivity for particular Hedgehog/ptc/smoothened pathways, e.g., which isotype specific for ptc (e.g., ptc-1, ptc-2) or Hedgehog (e.g., Shh, Ihh, Dhh, etc.). For instance, the subject method may employ steroidal alkaloids which do not substantially interfere with the biological activity of such steroids as aldosterone, androstane, androstene, androstenedione, androsterone, cholecalciferol, cholestane, cholic acid, corticosterone, cortisol, cortisol acetate, cortisone, cortisone acetate, deoxycorticosterone, digitoxigenin, ergocalciferol, ergosterol, estradiol-17-a, estradiol-17-β, estriol, estrane, estrone, hydrocortisone, lanosterol, lithocholic acid, mestranol, β-methasone, prednisone, pregnane, pregnenolone, progesterone, spironolactone, testosterone, triamcinolone and their derivatives, at least so far as those activities are unrelated to ptc related signaling.

In one embodiment, the subject steroidal alkaloid for use in the present method has a kd for members of the nuclear hormone receptor superfamily of greater than 1 µM, and more preferably greater than 1 mM, e.g., it does not bind estrogen, testosterone receptors or the like. Preferably, the subject smoothened antagonist has no estrogenic activity at physiological concentrations (e.g., in the range of 1 ng-1 mg/kg).

In this manner, untoward side effects which may be associated certain members of the steroidal alkaloid class can be reduced. For example, using drug screening assays, the application of combinatorial and medicinal chemistry techniques to the steroidal alkaloids provides a means for reducing such unwanted negative side effects including personality changes, shortened life spans, cardiovascular diseases and vascular occlusion, organ toxicity, hyperglycemia and diabetes, Cushnoid features, "wasting" syndrome, steroidal glaucoma, hypertension, peptic ulcers, and increased susceptibility to infections. For certain embodiments, it will be beneficial to reduce the teratogenic activity relative to jervine, as for example, in the use of the subject method to selectively inhibit spermatogenesis.

In a preferred embodiment, the subject antagonists are steroidal alkaloids other than spirosolane, tomatidine, jervine, etc. In particular embodiments, the steroidal alkaloid is chosen for use because it is more selective for one patched isoform over the next, e.g., 10-fold, and more preferably at least 100- or even 1000-fold more selective for one patched pathway (ptc-1, ptc-2) over another. Likewise, the steroidal alkaloid may be chosen for use because it is more selective for one smoothened isoform over the next, e.g., 10-fold, and more preferably at least 100- or even 1000-fold more selective for one wild-type smoothened protein (should various isoforms exist) or for activated smoothened mutants relative to wild-type smoothened.

In certain embodiments, the subject method can be carried out conjointly with the administration of growth and/or trophic factors, or compositions that also act on other parts of the Hedgehog/smoothened pathway. For instance, it is contemplated that the subject methods can include treatment with an agent that modulates cAMP levels, e.g., increasing or decreasing intracellular levels of cAMP.

In one embodiment, the subject method utilizes a smoothened antagonist, and the conjoint agent elevates cAMP levels in order to enhance the efficacy of the smoothened antagonist. For example, compounds that may activate adenylate cyclase include forskolin (FK), cholera toxin (CT), pertussis toxin (PT), prostaglandins (e.g., PGE-1 and PGE-2), colforsin and β-adrenergic receptor agonists. β-Adrenergic receptor agonists (sometimes referred to herein as "β-adrenergic agonists") include albuterol, bambuterol, bitolterol, carbuterol, clenbuterol, clorprenaline, denopamine, dioxethedrine, dopexamine, ephedrine, epinephrine, etafedrine, ethylnorepinephrine, fenoterol, formoterol, hexoprenaline, ibopamine, isoetharine, isoproterenol, mabuterol, metaproterenol, methoxyphenamine, norepinephrine, oxyfedrine, pirbuterol, prenalterol, procaterol, propranolol, protokylol, quinterenol, reproterol, rimiterol, ritodrine, salmefamol, soterenol, salmeterol, terbutaline, tretoquinol, tulobuterol, and xamoterol.

Compounds which may inhibit a cAMP phosphodiesterase include anrinone, milrinone, xanthine, methylxanthine, anagrelide, cilostamide, medorinone, indolidan, rolipram, 3-isobutyl-1-methylxanthine(IBMX), chelerythrine, cilostazol, glucocorticoids, griseolic acid, etazolate, caffeine, indomethacin, papverine, MDL 12330A, SQ 22536, GDPssS, clonidine, type III and type IV phosphodiesterase inhibitors, methylxanthines such as pentoxifylline, theophylline, theobromine, pyrrolidinones and phenyl cycloalkane and cycloalkene derivatives (described in PCT publications Nos. WO 92/19594 and WO 92/10190),lisophylline, and fenoxamine.

Analogs of cAMP which may be useful in the present method include dibutyryl-cAMP (db-cAMP),(8-(4)-chlorophenylthio)-cAMP (cpt-cAMP), 8-[(4-bromo-2,3-dioxobutyl)thio]-cAMP, 2-[(4-bromo-2,3-dioxobutyl)thio]- cAMP, 8-bromo-cAMP, dioctanoyl-cAMP, Spadenosine 3':5'-cyclic phosphorothioate, 8-piperidino-cAMP, N6-phenyl-cAMP, 8-methylamino-cAMP, 8-(6-aminohexyl)amino-cAMP, 2'-deoxycAMP, N6,2'-O-dibutryl-cAMP, N6,2'-O-disuccinyl-cAMP, N6-monobutyryl-cAMP, 2'-O-monobutyrylcAMP,2'-O-monobutryl-8-bromo-cAMP, N6-monobutryl-2'-deoxy-cAMP, and 2'-O-monosuccinyl-cAMP.

Compounds which may reduce the levels or activity of cAMP include prostaglandylinositol cyclicphosphate (cyclic PIP), endothelins (ET)-1 and -3, norepinepurine, K252a, dideoxyadenosine, dynorphins, melatonin, pertussis toxin, staurosporine, Gi agonists, MDL 12330A, SQ 22536, GDPssS and clonidine, β-blockers, and ligands of G-protein coupled receptors. Additional compounds are disclosed in U.S. Pat. Nos. 5,891,875, 5,260,210, and 5,795,756.

In certain embodiments, a compound which is an antagonist of the Hedgehog pathway is chosen to selectively antagonize Hedgehog activity over protein kinases other than PKA, such as PKC, e.g., the compound modulates the activity of the Hedgehog pathway at least an order of magnitude more strongly than it modulates the activity of another protein kinase, preferably at least two orders of magnitude more strongly, even more preferably at least three orders of magnitude more strongly. Thus, for example, a preferred inhibitor of the Hedgehog pathway may inhibit Hedgehog activity with a $K_i$ at least an order of magnitude lower than its $K_i$ for inhibition of PKC, preferably at least two orders of magnitude lower.

3.2.2 Protein Therapeutics

In some embodiments of the present invention, polypeptides (including proteins) and/or modified polypeptides/proteins are used as therapeutics.

There are several variants that are able to function as antagonists. At least five different techniques can be envisioned: Antibody antagonists, Dominant-negative versions of Hedgehog, soluble receptors ("interceptors"), randomly selected peptide antagonists, or randomly selected peptoid antagonists.

3.2.2.1 General Methods

There are two general ways of administering a polypeptide to a subject: Either one administers the isolated polypeptide, or one administers a gene transfer vector that encodes the desired polypeptide. In the first case, the isolated polypeptide is synthesized outside the mammalian subject to be treated, in the second case, the polypeptide is synthesized within the mammalian subject, using the cellular machinery of the transduced cell(s) within the mammalian subject.

Isolated polypeptides can be produced by any suitable method known in the art. Such methods range from direct protein synthetic methods to constructing a DNA sequence encoding isolated polypeptide sequences and expressing those sequences in a suitable transformed host.

Standard methods may be applied to synthesize an isolated polypeptide sequence of interest using standard methods of in vitro protein synthesis.

In one embodiment of a recombinant method, a DNA sequence is constructed by isolating or synthesizing a DNA sequence encoding a wild type protein of interest. Optionally, the sequence may be mutagenized by site-specific mutagenesis to provide functional analogs thereof, or modified by any other means, e.g., by fusing to another gene sequence, thus generating fusion proteins, or by deleting specific parts of the gene sequence, resulting in the expression of a protein that lacks specific parts compared to the wild-type form. For example, a transmembrane domain can be deleted, thus creating a secreted version of a protein that—in its original state—is membrane anchored.

Another method of constructing a DNA sequence encoding a polypeptide of interest would be by chemical synthesis using an oligonucleotide synthesizer. Such oligonucleotides may be preferably designed based on the amino acid sequence of the desired polypeptide, and preferably selecting those codons that are favored in the host cell in which the recombinant polypeptide of interest will be produced. For example, a DNA oligomer containing a nucleotide sequence coding for the particular isolated polypeptide may be synthesized. In one embodiment, several small oligonucleotides coding for portions of the desired polypeptide may be synthesized and then ligated. The individual oligonucleotides typically contain 5' or 3' overhangs for complementary assembly. A complete amino acid sequence may be used to construct a back-translated gene.

Once assembled (by synthesis, polymerase chain reaction, site-directed mutagenesis, or by any other method), the mutant DNA sequences encoding a particular isolated polypeptide of interest will be inserted into an expression vector and operatively linked to an expression control sequence appropriate for expression of the protein in a desired host. Proper assembly may be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The choice of expression control sequence and expression vector will depend upon the choice of the corresponding host. A wide variety of expression host/vector combinations may be employed. Useful expression vectors for eukaryotic hosts, include, for example, vectors comprising expression control sequences from SV40, bovine papilloma virus, retrovirus, adenovirus and cytomegalovirus. Useful expression vectors for bacterial hosts include known bacterial plasmids, such as plasmids from *Escherichia coli*, including pCRI, pBR322, pMB9 and their derivatives, wider host range plasmids, such as M13 and filamentous single-stranded DNA phages. Preferred *E. coli* vectors include pL vectors containing the lambda phage pL promoter (U.S. Pat. No. 4,874,702), pET vectors containing the T7 polymerase promoter [82] and the pSP72 vector. Useful expression vectors for yeast cells, for example, include the 2 g and centromere plasmids.

Further, within each specific expression vector, various sites may be selected for insertion of these DNA sequences. These sites are usually designated by the restriction endonuclease which cuts them. They are well-recognized by those of skill in the art. It will be appreciated that a given expression vector useful in this invention need not have a restriction endonuclease site for insertion of the chosen DNA fragment. Instead, the vector may be joined by the fragment by alternate means.

The expression vector, and the site chosen for insertion of a selected DNA fragment and operative linking to an expression control sequence, is determined by a variety of factors such as: the number of sites susceptible to a particular restriction enzyme, the size of the polypeptide, how easily the polypeptide is proteolytically degraded, and the like. The choice of a vector and insertion site for a given DNA is determined by a balance of these factors.

To provide for adequate transcription of the recombinant constructs of the invention, a suitable promoter/enhancer sequence may preferably be incorporated into the recombinant vector, provided that the promoter/expression control sequence is capable of driving transcription of a nucleotide sequence encoding the polypeptide of interest. Any of a wide variety of expression control sequences may be used in these vectors. Such useful expression control sequences include the expression control sequences associated with structural genes of the foregoing expression vectors. Examples of useful expression control sequences include, for example, the-early and late promoters of SV40 or adenovirus, the lac system, the trp system, the TAC or TRC system, the major operator and promoter regions of phage lambda, for example pL, the control regions of fd coat protein, the promoter for 3-phosphoglycerate kinase or other glycolytic enzymes, the promoters of acid phosphatase, e.g., Pho5, the promoters of the yeast α-mating system and other sequences known to control the expression of genes of prokaryotic or eukaryotic cells and their viruses, and various combinations thereof. Many of the vectors mentioned are commercially available. One supplier is Invitrogen, Carlsbad, USA. The company also offers detailed information on the sequence of the vectors it sells.

Any suitable host may be used to produce in quantity the isolated polypeptides of the invention, including bacteria, fungi (including yeasts), plants, insects, mammals, or other appropriate animal cells or cell lines, as well as transgenic animals or plants. More particularly, these hosts may include well known eukaryotic and prokaryotic hosts, such as strains of *E. coli, Pseudomonas, Bacillus, Streptomyces*, fungi, yeast (e.g., Hansenula), insect cells such as *Spodoptera firugiperda* (SF9), and High Five ™, animal cells such as Chinese hamster ovary (CHO), mouse cells such as NS/O cells, African green monkey cells, COS 1, COS 7, BSC 1, BSC 40, and BMT 10, and human cells, as well as plant cells.

Promoters which may be used to control the expression of polypeptides in eukaryotic cells include, but are not limited to, the SV40 early promoter region [83], the promoter contained in the 3' long terminal repeat of Rous sarcoma virus [84], the herpes thymidine kinase promoter [85], the regulatory sequences of the metallothionine gene [86].

In case the polypeptide is expressed in plants, plant expression vectors should be used comprising the nopaline synthetase promoter region [87] or the cauliflower mosaic virus 35S RNA promoter [88], and the promoter for the photosynthetic enzyme ribulose biphosphatecarboxylase [87].

In case the polypeptide is expressed in yeast or other fungi, promoter elements should be chosen such as the Gal 4 promoter, the ADC (alcohol dehydrogenase) promoter, PGK (phosphoglycerolkinase) promoter, alkaline phosphatase promoter.

In case the polypeptide is expressed in transgenic animals, the following animal transcriptional control regions can be used, which exhibit tissue specificity and have been utilized in transgenic animals: elastase I gene control region which is active in pancreatic cells ([89]; [90]); insulin gene enhancers for promoters which are active in pancreatic cells ([91]); immunoglobulin gene enhancers or promoters which are active in lymphoid cells ([92]; [93]; [94]); the cytomegalovirus early promoter and enhancer regions ([95]); mouse mammary tumor virus control region which is active in testicular, breast, lymphoid and mast cells ([96]); albumin gene control region which is active in liver [97]; α-fetoprotein gene control region which is active in liver ([98]; [99]); α-antitrypsin gene control region which is active in the liver ([100]); β-globin gene control region which is active in myeloid cells ([101]), myelin basic protein gene control region which is active in oligodendrocyte cells in the brain [102]; myosin light chain-2 gene control region which is active in skeletal muscle [103]; and gonadotropic releasing hormone gene control region which is active in the hypothalamus ([104]).

Operative linking of a DNA sequence to an expression control sequence includes the provision of a translation start signal in the correct reading frame upstream of the DNA sequence. If the particular DNA sequence being expressed does not begin with a methionine, the start signal will result in an additional amino acid (methionine) being located at the N-terminus of the product. If a hydrophobic moiety is to be linked to the N-terminal methionyl-containing protein, the protein may be employed directly in the compositions of the invention. Yet, methods are available in the art to remove N-terminal methionines from polypeptides expressed with them. For example, certain hosts and fermentation conditions permit removal of substantially all of the N-terminal methionine in vivo.

It should be understood that not all vectors and expression control sequences will function equally well to express a given isolated polypeptide. Neither will all hosts function equally well with the same expression system. However, one of skill in the art may make a selection among these vectors, expression control systems and hosts without undue experimentation.

Successful incorporation of these polynucleotide constructs into a given expression vector may be identified by three general approaches: (a) DNA-DNA hybridization, (b) presence or absence of "marker" gene functions, and (c) expression of inserted sequences. In the first approach, the presence of the gene inserted in an expression vector can be detected by DNA-DNA hybridization using probes comprising sequences that are homologous to the inserted gene. In the second approach, the recombinant vector/host system can be identified and selected based upon the presence or absence of certain "marker" gene functions (e.g., thymidine kinase activity, resistance to antibiotics such as G418, transformation phenotype, occlusion body formation in baculovirus, etc.) caused by the insertion of foreign genes in the vector. For example, if the polynucleotide is inserted so as to interrupt a marker gene sequence of the vector, recombinants containing the insert can be identified by the absence of the marker gene function. In the third approach, recombinant expression vectors can be identified by assaying the foreign gene product expressed by the recombinant vector. Such assays can be based, for example, on the physical or functional properties of the gene product in bioassay systems.

Recombinant nucleic acid molecules which encode modified protein therapeutics may be obtained by any method known in the art (Maniatis et al., 1982, Molecular Cloning; A Laboratory Manual, Cold Spring Harbor Laboratory, Cold Spring Harbor, N.Y.) or obtained from publicly available clones. Modifications comprise—but are not limited to—deletions, insertions, point mutations, fusions to other polypeptides. In some embodiments of the invention, a recombinant vector system may be created to accommodate sequences encoding the therapeutic of interest in the correct reading frame with a synthetic hinge region. Additionally, it may be desirable to include, as part of the recombinant vector system, nucleic acids corresponding to the 3' flanking region of an immunoglobulin gene including RNA cleavage/polyadenylation sites and downstream sequences. Furthermore, it may be desirable to engineer a signal sequence upstream of the modified protein therapeutic to facilitate the secretion of the protein therapeutic from a cell transformed with the recombinant vector. This is particularly of interest in embodiments, where a normally membrane-bound protein is modified in a way so that it will be secreted instead.

There are also commercial services available that will synthesize any desired gene or genetic sequence based upon an electronically submitted gene sequence (e.g., Medigenomix, Munich, Germany; Geneart, Regensburg, Germany). They will also provide the insertion of the gene sequence into a gene expression vector of choice. These commercial services not only enable the artisan, but everyone to gain access to any genetic vector they desire. This actually should be considered the optimal method for obtaining a gene transfer vector.

The proteins produced by a transformed host can be purified according to any suitable method. Such standard methods include chromatography (e.g., ion exchange, affinity, and sizing column chromatography), centrifugation, differential solubility, or by any other standard technique for protein purification. For immunoaffinity chromatography, the protein of interest may be isolated by binding it to an affinity column comprising antibodies that were raised against said protein or a cross-reactive protein and were affixed to a stationary support. to give a substantially pure protein. By the term "substantially pure" is intended that the protein is free of the impurities that are naturally associated therewith. Substantial purity may be evidenced by a single band by electrophoresis. Isolated proteins can also be characterized physically using such techniques as proteolysis, nuclear magnetic resonance, and X-ray crystallography.

In one embodiment, a modified, secreted version of Hip1 is purified by passing a supernatant containing said secreted version of Hip1 through an affinity column that has Shh bound to it. The bound target protein may then be eluted by treatment with a chaotropic salt or by elution with aqueous acetic acid. In one embodiment, specific immunoglobulin fusion proteins may be purified by passing a solution containing the fusion protein through a column which contains immobilized protein A or protein G which selectively binds the Fc portion of the fusion protein (PCT Application, Publication No. WO87/00329).

Alternatively, affinity tags such as hexa-histidine, maltose binding domain, influenza coat sequence, and glutathione-S-transferase can be attached to the protein to allow easy purification by passage over an appropriate affinity column.

3.2.2.2 Soluble Receptors (Interceptors)

In certain embodiments, soluble receptors are used to interfere with Hedgehog signaling. Many receptors are normally membrane-bound proteins and can be "solubilized" by removing their transmembrane domain. In instances where removing the transmembrane domain leaves the remaining domains functional, particularly the domain that interacts with the ligand, a soluble receptor can be used as an antagonist: Said soluble receptor ("interceptor") is able to bind and thus sequester its ligand so that the ligand cannot bind any more to the functional, membrane-bound receptor. In other words, the soluble receptor competes with the membrane-bound receptor for ligand binding. By providing the soluble receptor in excess, one can prevent binding of the ligand (e.g., Hedgehog) to its receptor, thus preventing activation of the corresponding signaling pathway.

In one embodiment, Hip1 is modified in a way so that it lacks its transmembrane domain. The transmembrane domain is removed from the genetic sequence of the HHIP gene by standard recombination technologies, preferentially by PCR mutagenesis. The modified HHIP gene can then be expressed in appropriate host cells. The synthesized, modified Hip1 is then secreted from its host cells, but is still able to bind and thus sequester Hedgehog.

3.2.2.3 Dominant-Negative Hedgehog Variants

Several Hedgehog variants are unable to elicit a Hedgehog-dependent response on C3HlOT1/2 cells, but they competed with mature Hedgehog for function and therefore serve as functional antagonists. The synthesis and use of such Hedgehog antagonist moieties are described in prior art.

To summarize: Certain Hedgehog variants that contain N-terminal modifications can block Hedgehog function because they lack the ability to elicit a Hedgehog-dependent response but retain the ability to bind to the Hedgehog receptor, patched-1. The critical primary amino acid sequence that defines whether a Hedgehog polypeptide (i.e., a Sonic, Indian or Desert Hedgehog) is a functional Hedgehog antagonist is the N-terminal cysteine residue that corresponds to Cys-1 of the mature Hedgehog. So long as the Hedgehog polypeptide either lacks this N-terminal cysteine completely or contains this N-terminal cysteine in a modified form (e.g. chemically modified or included as part of an N-terminal extension moiety), the resulting polypeptide can act as a functional Hedgehog antagonist.

Provided that, for example, a Sonic Hedgehog has an N-terminal cysteine corresponding to Cys-1 that is altered or otherwise modified, it can antagonize the action of any other member of the Hedgehog family. One skilled in the art can alter the structure of the antagonist, e.g., by producing fragments or analogs, and test the newly produced structures for antagonist activity. These, or analogous methods, can be used to make and screen fragments and analogs of a antagonist polypeptides.

Antagonist forms of Hedgehog may be identified by using a Hedgehog sensitive screening system. For example, a cell line transfected with a gli-1-lacz reporter gene construct could be monitored for $\beta$-galactosidase activity. Gli-1 is a reporter for activation of the Hedgehog signaling pathway and Hedgehog mutants that inhibit gli-1-driven reporter gene expression would be Hedgehog antagonists. Any number of reporter genes may be used, including luciferase, green fluorescent protein (and variants including yellow, red, blue and cyan), GUS, and other fluorescent or chromogenic proteins.

3.2.2.4 Antibody Antagonists

It is anticipated that antibodies can act as hedgehog antagonists. Antibodies can have extraordinary affinity and specificity for particular epitopes. Antibodies that bind to any protein in the hedgehog signaling pathway may have the capacity to act as antagonists. Antibodies that bind to hedgehog or smoothened may act by simply sterically hindering the proper protein-protein interactions or occupying active sites. Antibodies that bind to patched proteins may act as antagonists if they cause hyperactivation of the patched protein, for example stimulating patched association with smoothened. Proteins with extracellular domains are readily bound by exogenously supplied antibodies.

Several anti-hedgehog or patched monoclonal antibodies have been previously described. These anti-hedgehog or patched monoclonal antibodies and others will be useful in the methods of treatment according to the present invention.

In one embodiment of the present invention, hedgehog antibodies are used to interfere with hedgehog signaling: By binding to secreted Hedgehog in general, and Shh in particular, preferentially the N-terminal fragment, antibodies can prevent Shh to interact with its receptor Patch proteins. Preferred antibodies are specifically immunoreactive with a vertebrate hedgehog protein. For example, by using immunogens derived from hedgehog protein, monoclonal or polyclonal antibodies can be made using standard protocols (See, for example, Antibodies: A laboratory manual ed. by Harlow and Lane (Cold Spring Harbor Press: 1988)). A mammal, such as a mouse, a hamster or rabbit can be immunized with an immunogenic form of the peptide (e.g., a vertebrate hedgehog polypeptide or an antigenic fragment which is capable of eliciting an antibody response). Techniques for conferring immunogenicity on a protein or peptide include conjugation to carriers or other techniques well known in the art. An immunogenic portion of a hedgehog protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a hedgehog protein of a vertebrate organism. In yet a further preferred embodiment the present invention provides, for example, antibodies which are immunospecific for discrete hedgehog family member, e.g. Shh versus Dhh versus Ihh. Antibodies which are immunospecific for hedgehog, or for a specific hedgehog family member do not substantially cross-react with non-homologous proteins. In one embodiment, the antibody does not substantially cross-react with an invertebrate hedgehog protein.

The term antibody as used herein is intended to include fragments thereof that are also specifically reactive with one or more of the vertebrate hedgehog polypeptides. Antibodies can be fragmented using conventional techniques, and the fragments are screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific and chimeric molecules having affinity for a hedgehog protein conferred by at least one CDR region of the antibody.

Both monoclonal and polyclonal antibodies immunoreactive with hedgehog polypeptides can be used as hedgehog antagonists. Although not all hedgehog antibodies function as hedgehog antagonists, antibodies with hedgehog antagonist activity can be identified in much the same way as other hedgehog antagonists. For example, candidate antibodies can be administered to cells expressing a reporter protein under the control of a Hedgehog-controlled promoter, and antibodies that cause decreased reporter gene expression are antagonists.

In one variation, antibodies of the invention can be single chain antibodies (scFv), comprising variable antigen binding domains linked by a polypeptide linker. Single chain antibodies are expressed as a single polypeptide chain and can be expressed in bacteria and as part of a phage display library. In this way, phages that express the appropriate scFv will have hedgehog antagonist activity. The nucleic acid encoding the single chain antibody can then be recovered from the phage and used to produce large quantities of the scFv. Construction and screening of scFv libraries is extensively described in various publications (U.S. Pat. Nos. 5,258,498; 5,482,858; 5,091,513; 4,946,778; 5,969,108; 5,871,907; 5,223,409; 5,225,539).

An illustrative example of a hedgehog antibody which functions as a hedgehog antagonist is 5E1. As noted in the Examples provided herein, 5E1 functions in vitro and in vivo as a hedgehog antagonist. The invention specifically contemplates the use of 5E1, or an antibody which recognizes the same epitope as 5E1 in the subject methods.

The technology for producing monoclonal antibodies is well known. See, for example, WO93/09229, or U.S. Pat. No. 5,411,941, Fully human monoclonal antibody homologs against hedgehog or patched are another preferred binding agent that may block or coat hedgehog ligands in the method of the invention. In their intact form these may be prepared using in vitro-primed human splenocytes, as described in [105]. Alternatively, they may be prepared by repertoire cloning as described in [106] or in [107] or in U.S. Pat. No. 5,798,230 that describes preparation of human monoclonal antibodies from human B cells. According to this process, human antibody-producing B cells are immortalized by infection with an Epstein-Barr virus, or a derivative thereof, that expresses Epstein-Barr virus nuclear antigen 2 (EBNA2). EBNA2 function, which is required for immortalization, is subsequently shut off, which results in an increase in antibody production.

In yet another method for producing fully human antibodies, U.S. Pat. No. 5,789,650 describes transgenic non-human animals capable of producing heterologous antibodies and transgenic non-human animals having inactivated endogenous immunoglobulin genes.

Large nonimmunized human phage display libraries may also be used to isolate high affinity antibodies that can be developed as human therapeutics using standard phage technology [108-110].

Yet another preferred binding agent that may block or coat hedgehog ligands in the method of the invention is a humanized recombinant antibody homolog having anti-hedgehog, anti-Smo or patched specificity. Following the early methods for the preparation of true "chimeric antibodies" (where the entire constant and entire variable regions are derived from different sources), a new approach was described in EP 0239400 (Winter et al.) whereby antibodies are altered by substitution (within a given variable region) of their complementarity determining regions (CDRs) for one species with those from another. The process for humanizing monoclonal antibodies via CDR "grafting" has been termed "reshaping" [111-113]. See also U.S. Pat. Nos. 5,693,762; 5,693,761; 5,585,089; and 5,530,101 (Protein Design Labs).

3.2.2.5 Peptoids

Peptoids can be developed for any given protein, particularly for secreted proteins such as proteins of the Hedgehog family. How to generate and isolate peptoids has been described in prior art. U.S. Patent application 20040161798 is included hereby by reference. One of ordinary skill in the art will be able to generate and isolate peptoids that interfere with Hedgehog signaling function. Peptoids against Hedgehog proteins, Gli-1, or Fu are of particular interest. One strength of peptoids is that they can also pass through plasma membranes and thus, they can be targeted against intracellular proteins such as, e.g., Gli-1.

3.2.3 Antisense, Ribozyme, Triple Helix RNA Interference and Aptamer Techniques

Another aspect of the invention relates to the use of nucleic acids and/or modified nucleic acids as therapeutics. In some embodiments, these nucleic acids are produced inside cells via means of gene transfer vectors. In other embodiments, these nucleic acids are directly administered to the mammalian subject in vivo. At least four different techniques have been described in prior are: Antisense, ribozyme, RNA interference and aptamers.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

3.2.3.1 Antisense

As used herein, "antisense" therapy refers to administration or in situ generation of oligonucleotide molecules or their derivatives which specifically hybridize (e.g., bind) under cellular conditions, with the cellular mRNA and/or genomic DNA encoding one or more of the subject hedgehog pathway proteins so as to inhibit expression of that protein, e.g., by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy that relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a hedgehog signaling protein. Alternatively, the antisense construct is an oligonucleotide probe that is generated ex vivo and which, when introduced into the cell causes inhibition of expression by hybridizing with the mRNA and/or genomic sequences of a hedgehog signaling gene. Such oligonucleotide probes are preferably modified oligonucleotides that are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, in [114]; or [115]. With respect to antisense DNA, oligodeoxyribonucleotides derived from the translation initiation site, e.g., between the −10 and +10 regions of the hedgehog signaling gene nucleotide sequence of interest, are preferred.

Antisense approaches involve the design of oligonucleotides (either DNA or RNA) that are complementary to mRNA encoding a hedgehog signaling protein. The antisense oligonucleotides will bind to the mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well [116]. Therefore, oligonucleotides complementary to either the 5' or 3' untranslated, non-coding regions of a gene could be used in an antisense approach to inhibit translation of that mRNA. Oligonucleotides complementary to the 5' untranslated region of the mRNA should include the complement of the AUG start codon. Antisense oligonucleotides complementary to mRNA coding regions are less efficient inhibitors of translation but could also be used in accordance with the invention. Whether designed to hybridize to the 5', 3' or coding region of mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., [117]; [118]; PCT Publication No. WO88/09810) or the blood-brain barrier (see, e.g., PCT Publication No. WO89/10134), hybridization-triggered cleavage agents [114] or intercalating agents [119]. To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl) uracil, 5-carboxymethylaminomethyl-2-thiouridine, 5-carboxymethylaminomethyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil; β-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in [120] and [121]. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an—anomeric oligonucleotide. An—anomeric oligonucleotide forms specific double-stranded hybrids with complementary RNA in which, contrary to the usual units, the strands run parallel to each other [122]. The oligonucleotide is a 2'-O-methylribonucleotide [123], or a chimeric RNA-DNA analogue.

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. [124-127], methylphosphonate oligonucleotides can be prepared by use of controlled pore glass polymer supports [128].

While antisense nucleotides complementary to the coding region of an mRNA sequence can be used, those complementary to the transcribed untranslated region and to the region comprising the initiating methionine are most preferred.

The antisense molecules can be delivered to cells that express hedgehog signaling genes in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigen expressed on the target cell surface) can be administered systematically.

However, it may be difficult to achieve intracellular concentrations of the antisense sufficient to suppress translation on endogenous mRNAs in certain instances. Therefore a preferred approach utilizes a recombinant DNA construct in which the antisense oligonucleotide is placed under the control of a strong pol m or pol II promoter. The use of such a construct to transfect target cells in the patient will result in the transcription of sufficient amounts of single stranded RNAs that will form complementary base pairs with the endogenous hedgehog signaling transcripts and thereby prevent translation. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region [83], the promoter contained in the 3' long terminal repeat of Rous sarcoma virus [84], the herpes thymidine kinase promoter [85], the regulatory sequences of the metallothionein gene (Brinster et al, 1982, Nature 296:3942), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

3.2.3.2 Ribozymes

Ribozyme molecules designed to catalytically cleave hedgehog signaling mRNA transcripts can also be used to prevent translation of mRNA (See, e.g., PCT International Publication WO90/11364, published Oct. 4, 1990; [129], U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in [130].

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators [131-135], published International patent application No. WO88/04300; [136]. The Cech-type ribozymes have an eight base pair active site that hybridizes to a target RNA sequence whereafter cleavage of the target RNA takes place. The invention encompasses those Cech-type ribozymes that target eight base-pair active site sequences.

As in the antisense approach, the ribozymes can be composed of modified oligonucleotides (e.g., for improved stability, targeting, etc.) and should be delivered to cells that express hedgehog signaling genes in vivo. A preferred method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes unlike antisense molecules, are catalytic, a lower intracellular concentration is required for efficiency.

3.2.3.3 Triple Helix Formation

Alternatively, endogenous hedgehog signaling gene expression can be reduced by targeting deoxyribonucleotide sequences complementary to the regulatory region of the gene (i.e., the promoter and/or enhancers) to form triple helical structures that prevent transcription of the gene in target cells in the body. (See generally, [137]; [138]).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

3.2.3.4 RNA Interference

The discovery that RNA interference (RNAi) seems to be a ubiquitous mechanism to silence genes suggests an alternative, novel approach to decrease gene expression, which is able to overcome the limitations of the other approaches outlined above. Short interfering RNAs (siRNAs) are at the heart of RNAi. The antisense strand of the siRNA is used by an RNAi silencing complex to guide cleavage of complementary mRNA molecules, thus silencing expression of the corresponding gene [6-10].

The present invention—leveraging RNAi—thus differs from other nucleic acid based strategies (antisense and ribozyme methods) in both approach and effectiveness:

(a) Compared to antisense strategies, RNAi leverages a catalytic process, i.e., a small amount of siRNA is capable of decreasing the concentration of the target gene mRNA within the target cell. As antisense is based on a stochiometric process, a much larger concentration of effector molecules is required within the target cell, i.e., a concentration is required that is equal to or greater than the concentration of endogenous mRNA. Thus, as RNAi is a catalytic process, a lower amount of effector molecules (i.e., siRNAs) is sufficient to mediate a therapeutic effect.

(b) Compared to ribozymes (which have a catalytic function as well), RNAi seems to be a more flexible strategy, which allows targeting a higher variety of target sequences and thus offers more flexibility in construct design. Moreover, design of RNAi constructs is fast and convenient as the artisan can design those constructs based on the sequence information of the RNAi target gene. With ribozymes, more trial-and-error experiments and more sophisticated design algorithms are required as ribozymes are more complex in nature. Last, RNAi is more efficacious in vivo compared to ribozymes as RNAi leverages ubiquitous, endogenous cell machinery.

The present invention also differs from protein-based strategies, as RNAi does not require the expression of non-endogenous proteins (such as artificial transcription factors), thus lowering the risk of an unintended immune response.

In summary, RNAi-mediated down-regulation of gene expression is a novel mechanism with clear advantages over existing gene expression down-regulation approaches.

RNAi constructs comprise double stranded RNA that can specifically block expression of a target gene. Accordingly, RNAi constructs can act as antagonists by specifically blocking expression of a particular gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. Despite some mystery regarding the mechanism of action, RNAi provides a useful method of inhibiting gene expression in vitro or in vivo.

As used herein, the term "dsRNA" refers to siRNA molecules, or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs.

Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of an nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, [139]; [140]; [141]). Merely to illustrate, the backbone of an RNAi construct can be modified with phosphorothioates, phosphoramidate, phosphodithioates, chimeric methylphosphonatephosphodiesters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer doublestranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end ([75], [142]). These double-stranded siRNA structures can then be directly introduced to cells, either by passive uptake or a delivery system of choice, such as described below.

In certain embodiments, the siRNA constructs can be generated by processing of longer doublestranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects that may be caused by the sequence-independent dsRNA response. In such embodiments, the use of local delivery systems and/or agents which reduce the effects of interferon or PKR are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, [76]; [143]; [144]; [145]). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

Exemplary RNAi constructs that specifically recognize a particular gene, or a particular family of genes can be selected using methodology outlined in detail above with respect to the selection of antisense oligonucleotide. Similarly, methods of delivery RNAi constructs include the methods for delivery antisense oligonucleotides outlined in detail above.

In general, it is anticipated that any of the foregoing methods that decrease the presence or translation of hedgehog, smoothened or gli-1 mRNA will act as hedgehog antagonists, while methods that decrease the production of patched will have an agonist effect.

In certain embodiments, the subject antagonists can be chosen on the basis of their selectively for the hedgehog pathway. This selectivity can be for the hedgehog pathway versus other pathways, or for selectivity between particular hedgehog pathways, e.g., e.g., ptc-1, ptc-2, etc. In certain preferred embodiments, the subject inhibitors inhibit hedgehog-mediated signal transduction with an ED 50 of 1 mM or less, more preferably of 1 µM or less, and even more preferably of 1 nM or less.

In particular embodiments, the small molecule is chosen for use because it is more selective for one patched isoform over the next, e.g., 10 fold, and more preferably at least 100 or even 1000 fold more selective for one patched pathway (ptc-1, ptc-2) over another.

In certain embodiments, a compound which is an antagonist of the hedgehog pathway is chosen to selectively antagonize hedgehog activity over protein kinases other than PKA, such as PKC, e.g., the compound modulates the activity of the hedgehog pathway at least an order of magnitude more strongly than it modulates the activity of another protein kinase, preferably at least two orders of magnitude more strongly, even more preferably at least three orders of magnitude more strongly. Thus, for example, a preferred inhibitor of the hedgehog pathway may inhibit hedgehog activity with a Ki at least an order of magnitude lower than its Ki for inhibition of PKC, preferably at least two orders of magnitude lower, even more preferably at least three orders of magnitude lower. In certain embodiments, the Ki for PKA inhibition is less than 10 nM, preferably less than 1 nM, even more preferably less than 0.1 nM.

The design of the RNAi expression cassette does not limit the scope of the invention. Different strategies to design an RNAi expression cassette can be applied, and RNAi expression cassettes based on different designs will be able to induce RNA interference in vivo. (Although the design of the RNAi expression cassette does not limit the scope of the invention, some RNAi expression cassette designs are included in the detailed description of this invention and below.)

Features common to all RNAi expression cassettes are that they comprise an RNA coding region which encodes an RNA molecule which is capable of inducing RNA interference either alone or in combination with another RNA molecule by forming a double-stranded RNA complex either intramolecularly or intermolecularly.

Different design principles can be used to achieve that same goal and are known to those of skill in the art. For example, the RNAi expression cassette may encode one or more RNA molecules. After or during RNA expression from the RNAi expression cassette, a double-stranded RNA complex may be formed by either a single, self-complementary RNA molecule or two complementary RNA molecules. Formation of the dsRNA complex may be initiated either inside or outside the nucleus.

The RNAi target gene does not limit the scope of this invention and may be any gene that participates in the hedgehog signaling pathway. Thus, the choice of the RNAi target gene is not limiting for the present invention: The artisan will know how to design an RNAi expression cassette to down-regulate the gene expression of any RNAi target gene of interest. Depending on the particular RNAi target gene and method of delivery, the procedure may provide partial or complete loss of function for theRNAi target gene.

3.2.3.5 Aptamers

Aptamers are a non-naturally occurring nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. The target in case of the, present invention is a component of the Hedgehog signaling pathway.

Aptamers are identified based on the SELEX process [146-148]. In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5-50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer weakly binding sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained from a number of target species, including both protein targets where the protein is and is not a nucleic acid binding protein. The SELEX method further encompasses combining selected nucleic acid ligands with lipophilic or non-immunogenic, high molecular weight compounds in a diagnostic or therapeutic complex as described in U.S. patent application Ser. No. 08/434,465, filed May 4, 1995, entitled "Nucleic Acid Ligand Complexes".

In certain embodiments of the present invention it is desirable to provide a complex comprising one or more nucleic acid ligands to components of the Hedgehog signaling pathway covalently linked with a non-immunogenic, high molecular weight compound or lipophilic compound. A non-immunogenic, high molecular weight compound is a compound between approximately 100 Da to 1,000,000 Da, more preferably approximately 1000 Da to 500,000 Da, and most preferably approximately 1000 Da to 200,000 Da, that typically does not generate an immunogenic response. For the purposes of this invention, an immunogenic response is one that causes the organism to make antibody proteins. In one preferred embodiment of the invention, the non-immunogenic, high molecular weight compound is a polyalkylene glycol. In the most preferred embodiment, the polyalkylene glycol is polyethylene glycol (PEG). More preferably, the PEG has a molecular weight of about 10-80K. Most preferably, the PEG has a molecular weight of about 20-45K. In certain embodiments of the invention, the non-immunogenic, high molecular weight compound can also be a nucleic acid ligand.

3.2.4 Gene Transfer

In some embodiments, gene transfer to the eye is used instead of administering an exogenously synthesized protein. Upon transduction of corresponding host cells within the eye, said cells will start producing the protein encoded by the gene transfer vector. One vector system of particular importance for ocular gene transfer is a system based on recombinant AAV virions.

3.2.4.1 Recombinant AAV Virions

The recombinant AAV virions of the preferred embodiment, comprising an RNAi expression cassette, can be produced using standard methodology, known to the artisan. The Methods generally involve the steps of (1) introducing an AAV vector construct into a host cell (e.g., 293 cells);

(2) introducing an AAV packaging construct into the host cell, where the packaging construct includes AAV coding regions (e.g., rep and cap sequences) capable of being expressed in the host cell to complement AAV packaging functions missing from the AAV vector construct;

(3) introducing one or more helper viruses and/or accessory function vector constructs into the host cell, wherein the helper virus and/or accessory function vector constructs provide accessory functions capable of supporting efficient recombinant AAV ("rAAV") virion production in the host cell; and (4) culturing the host cell to produce rAAV virions.

The AAV vector construct, AAV packaging construct and the helper virus or accessory function vector constructs can be introduced into the host cell either simultaneously or serially, using standard transfection techniques.

In one embodiment, pseudotyped rAAV virions are produced, in which a non-AAV5 serotype ITR based RNAi expression cassette is packaged in an AAV5 capsid. The inventors have previously found that this pseudotyping can be achieved by utilizing a Rep protein (or a functional portion thereof) of the same serotype or a cross-reactive serotype as that of the ITRs found in the minigene in the presence of sufficient packaging and accessory functions to permit packaging [83]. Thus, an AAV2 minigene (harboring an RNAi expression cassette) can be pseudotyped in an AAV5 capsid by use of a rep protein from AAV2 or a cross-reactive serotype, e.g., AAV1, AAV3, AAV4 or AAV6. Similarly, an AAV minigene containing AAV1 5' ITRs and AAV2 3' ITRs may be pseudotyped in an AAV5 capsid by use of a Rep protein from AAV 1, AAV2, or another cross-reactive serotype. However, because AAV5 is not cross-reactive with the other AAV serotypes, an AAV5 minigene can be pseudotyped in a heterologous AAV capsid only by use of an AAV5 Rep protein.

In certain embodiments, the invention provides an rAAV virion, in which both the AAV ITRs and capsid protein are independently selected from among AAV serotypes, including, without limitation, AAV1, AAV2, AAV3, AAV4, AAV5, AAV6, AAV7, AAV8. For example, the invention may utilize a rAAV1 vector, a rAAV2 vector, a rAAV2/1 vector, and rAAV1/2 vector and/or a rAAV2/5 vector, as desired—following the nomenclature rAAVx/y with x: serotype source of ITRs, y: serotype source of capsid; rAAVz with z as serotype source of ITRs and capsid.

In another embodiment of this method, the delivery of vector with an AAV capsid protein may precede or follow delivery of a heterologous molecule (e.g., gene) via a vector with a different serotype AAV capsid protein. Thus, delivery via multiple rAAV vectors may be used for repeat delivery of a desired molecule to a selected host cell. Desirably, subsequently administered rAAV carry the same minigene as the first rAAV vector, but the subsequently administered vectors contain capsid proteins of serotypes which differ from the first vector. For example, if a first rAAV has an AAV5 capsid protein, subsequently administered rAAV may have capsid proteins selected from among the other serotypes, including AAV2, AAV1, AAV3A, AAV3B, AAV4 and AAV6. Alternatively, if a first rAAV has an AAV2 capsid protein, subsequently administered rAAV may have an AAV5 cansid. Still other suitable combinations will be readily apparent to one of skill in the art.

The host cell for rAAV virion production itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirements for the cell used is that it not carry any adenovirus gene other than E1, E2a and/or E4 ORF6; it not contain any other virus gene which could result in homologous recombination of a contaminating virus during the production of rAAV; and it is capable of infection or transfection of DNA and expression of the transfected DNA.

One host cell useful in the present invention is a host cell stably transformed with the sequences encoding rep and cap, and which is transfected with the adenovirus E1, E2a, and E40RF6 DNA and a construct carrying the minigene as described above. Stable rep and/or cap expressing cell lines, such as B-50 (PCT/US98/19463), or those described in U.S. Pat. No. 5,658,785, may also be similarly employed. Another desirable host cell contains the minimum adenoviral DNA which is sufficient to express E4 ORF6.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Introduction of the molecules (as plasmids or viruses) into the host cell may also be accomplished using techniques known to the skilled artisan and as discussed throughout the specification. In the preferred embodiment, standard transfection techniques are used, e.g., CaPO.sub.4 transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins). Thus produced, the rAAV may be used to prepare the compositions and kits described herein, and used in the method of the invention.

3.2.4.2 AAV Vector Constructs

AAv vector constructs are constructed using known techniques to at least provide, as operatively linked components in the direction of transcription, (a) control elements including a transcriptional initiation region, (b) the DNA of interest (here: at least an RNAi expression cassette), and (c) a transcriptional termination region. The control elements are selected to be functional in the targeted cell. The resulting construct, which contains the operatively linked components, is bounded (5' and 3') with functional AAV ITR sequences. The nucleotide sequences of AAV ITR regions are known. See, e.g., [84]; Berns, K. I. "Parvoviridae and their Replication" in Fundamental Virology, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides.

Additionally, AAV ITRs may be derived from any of several AAV serotypes, including AAV-1, AAV-2, AAV-3, AAV-4, AAV-5, AAV-6, AAV-7, AAV-8, etc. The 5 and 3' ITRs which flank a selected transgene expression cassette in an AAV vector plasmid need not necessarily be identical or derived from the same AAV serotype, as long as they function as intended, i.e., to allow for excision and replication of the bounded nucleotide sequence of interest when AAV rep gene products are present in the cell. Thus, rAAV vector design and production allows for exchanging of the capsid proteins between different AAV serotypes: Homologous vectors comprising an expression cassette flanked by e.g., AAV2-ITRs and packaged in an AAV2 capsid, can be produced as well as heterologous, hybrid vectors where the transgene expression cassette is flanked by e.g., AAV2 ITRs, but the capsid originates from another AAV serotype: The following combinations are feasible: rAAV2/1-8, where the first number defines the genome and the second the capsid of the AAV of origin. In its preferred embodiment, the gene transfer vector is produced using a rAAV2/5 design.

Suitable minigenes for use in AAV vectors will generally be less than about 5 kilobases (kb) in size, which is the case for RNAi expression cassettes. Given the size of most RNAi expression cassettes, other minigenes might be included in the same AAV vector comprising another gene of interest.

The AAV sequences used in generating the minigenes, vectors, and capsids, and other constructs used in the present invention may be obtained from a variety of sources. For example, the sequences may be provided by AAV type 5, AAV type 2, AAV type 1, AAV type 3, AAV type 4, AAV type 6, or other AAV serotypes or other densoviruses. A variety of these viral serotypes and strains are available from the American Type Culture Collection, Manassas, Va., or are available from a variety of academic or commercial sources. Alternatively, it may be desirable to synthesize sequences used in preparing the vectors and viruses of the invention using known techniques, which may utilize AAV sequences which are published and/or available from a variety of databases. The source of the sequences utilized in preparation of the constructs of the invention is not a limitation of the present invention.

3.2.4.3 rAAV Virion Production

In order to produce rAAV virions, an AAV vector construct that has been constructed as described above is introduced into a suitable host cell using known techniques, such as by transfection. A number of transfection techniques are generally known in the art. See, e.g., [69, 70], Sambrook et al. (1989) Molecular Cloning, a laboratory manual, Cold Spring Harbor Laboratories, New York, Davis et al. (1986) Basic Methods in Molecular Biology, Elsevier, and [71]. Particularly suitable transfection methods include calcium phosphate co-precipitation [69], direct micro-injection into cultured cells [85], electroporation [86], liposome mediated gene transfer [87], lipid-mediated transduction [88], and nucleic acid delivery using high-velocity microprojectiles.

The AAV vector construct harboring the AAV minigene is preferably carried on a plasmid which is delivered to a host cell by transfection. The plasmids useful in this invention may be engineered such that they are suitable for replication and, optionally, integration in prokaryotic cells, mammalian cells, or both. These plasmids (or other vectors carrying the 5' AAV ITR-heterologous molecule-3' AAV ITR) may contain sequences permitting replication of the AAV minigene in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the AAV minigene is transfected into the cell, where it may exist transiently or as an episome. Alternatively, the AAV minigene (carrying the 5' AAV ITR-heterologous molecule-3' AAV ITR) may be stably integrated into a chromosome of the host cell. Suitable transfection techniques are known and may readily be utilized to deliver the AAV minigene to the host cell.

Generally, when delivering the AAV vector construct comprising the AAV minigene by transfection, the vector is delivered in an amount from about 5 µg to about 100 µg DNA, and preferably about 10 to about 50 µg DNA to about $10^4$ cells to about $10^{13}$ cells, and preferably about $10^5$ cells. However, the relative amounts of vector DNA to host cells may be adjusted, taking into consideration such factors as the selected vector, the delivery method and the host cells selected.

For the purposes of the invention, suitable host cells for producing rAAV virions include microorganisms, yeast cells, insect cells, and mammalian cells, that can be, or have been, used for transfection. The term includes the progeny of the original cell which has been transfected. Thus, a "host cell" as used herein generally refers to a cell which has been transfected with an exogenous DNA sequence. Cells from the stable human cell line, 293 (readily available through, e.g., the ATCC under Accession No. ATCC CRL1573) are preferred in the practice of the present invention. Particularly, the human cell line 293 is a human embryonic kidney cell line that has been transformed with adenovirus type-5 DNA fragments [89], and expresses the adenoviral E1a and E1b genes [90]. The 293 cell line is readily transfected, and provides a particularly convenient platform in which to produce rAAV virions.

The components required to be cultured in the host cell to package the AAV minigene in the AAV capsid may be provided to the host cell in trans. Alternatively, any one or more of the required components (e.g., minigene, rep sequences, cap sequences, and/or accessory functions) may be provided by a stable host cell which has been engineered to contain one or more of the required components using methods known to those of skill in the art.

The minigene, rep sequences, cap sequences, and accessory (helper) functions required for producing the rAAV of the invention may be delivered to the packaging-host cell in the form of any genetic element, e.g., naked DNA, a plasmid, phage, transposon, cosmid, virus, etc. which transfer the sequences carried thereon. The selected-genetic element may be delivered by any suitable method, including transfection, electroporation, liposome delivery, membrane fusion techniques, high velocity DNA-coated pellets, viral infection and protoplast fusion.

3.2.4.4 AAV Packaging Functions

Host cells containing the above described AAV vector constructs must be rendered capable of providing AAV packaging functions in order to replicate and encapsidate the nucleotide sequences flanked by the AAV ITRs to produce rAAV virions. AAV packaging functions are generally AAV-derived coding sequences which can be expressed to provide AAV gene products that, in turn, function in trans for productive AAV replication and genome encapsidation. AAV packaging functions are used herein to complement necessary AAV functions that are missing from the AAV vectors. Thus, AAV packaging functions include one, or both of the major AAV ORFs, namely the rep and cap coding regions, or functional homologues thereof.

By "AAV rep coding region" is meant the art-recognized region of the AAV genome which encodes the replication proteins Rep78, Rep68, Rep52 and Rep40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., [84, 91]. Suitable homologues of the AAV rep coding region include the human herpesvirus 6 (HHV-6) rep gene which is also known to mediate AAV-2 DNA replication [92].

By "AAV cap coding region" is meant the art-recognized region of the AAV genome which encodes the capsid proteins VP1, VP2, and VP3, or functional homologues thereof. These cap expression products supply the packaging functions which are collectively required for packaging the viral genome. For a description of the AAV cap coding region, see, e.g., [84, 91].

AAV packaging functions are introduced into the host cell by transfecting the host cell with an AAV packaging construct either prior to, or concurrently with, the transfection of the AAV vector construct. AAV packaging constructs are thus used to provide at least transient expression of AAV rep and/or cap genes to complement missing AAV functions that are necessary for productive AAV infection. AAV packaging constructs lack AAV ITRs and can neither replicate nor package themselves. These constructs can be in the form of a plasmid, phage, transposon, cosmid, virus, or virion. A number of AAV packaging constructs have been described, such as the commonly used plasmids pAAV/Ad and pIM29+45 which encode both Rep and Cap expression products. See, e.g., [93, 94]. A number of other vectors have been described which encode Rep and/or Cap expression products. See, e.g., U.S. Pat. No. 5,139,941.

Additionally, when pseudotyping an AAV vector in an AAV5 capsid, the sequences encoding each of the essential Rep proteins may be supplied by the same AAV serotype as the ITRs, or the sequences encoding the Rep proteins may be supplied by different, but cross-reactive, AAV serotypes (e.g., AAV1, AAV2, AAV3, AAV4 and AAV6). For example, the Rep78/68 sequences may be from AAV2, whereas the Rep52/40 sequences may from AAV1.

In one embodiment, the host cell stably contains the capsid ORF under the control of a suitable promoter, such as those described above. Most desirably, in this embodiment, the capsid ORF is expressed under the control of an inducible promoter. In another embodiment, the capsid ORF is supplied to the host cell in trans. When delivered to the host cell in trans, the capsid ORF may be delivered via a plasmid that contains the sequences necessary to direct expression of the selected capsid ORF in the host cell. Most desirably, when delivered to the host cell in trans, the plasmid carrying the capsid ORF also carries other sequences required for packaging the rAAV, e.g., the rep sequences.

In another embodiment, the host cell stably contains the rep sequences under the control of a suitable promoter, such as those described above. Most desirably, in this embodiment, the essential Rep proteins are expressed under the control of an inducible promoter. In another embodiment, the rep ORF is supplied to the host cell in trans. When delivered to the host cell in trans, the rep ORF may be delivered via a plasmid which contains the sequences necessary to direct expression of the selected rep ORF in the host cell. Most desirably, when delivered to the host cell in trans, the plasmid carrying the rep ORF also carries other sequences required for packaging the rAAV, e.g., the cap sequences.

Thus, in one embodiment, the rep and cap sequences may be transfected into the host cell on a single nucleic acid molecule and exist in the cell as an episome. In another embodiment, the rep and cap sequences are stably integrated into the genome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

Optionally, the rep and/or cap sequences may be supplied on a vector that contains other DNA sequences that are to be introduced into the host cells. For instance, the vector may contain the rAAV vector construct comprising the AAV minigene. The vector may comprise one or more of the genes encoding the helper functions, e.g., the adenoviral proteins E1, E2a, and E4 ORF6, and the gene for VAI RNA.

In another embodiment, the promoter for rep is an inducible promoter, as discussed above in connection with regulatory sequences and promoters. One preferred promoter for rep expression is the T7 promoter. The vector comprising the rep gene regulated by the T7 promoter and the cap gene, is transfected or transduced into a cell which either constitutively or inducibly expresses the T7 polymerase. See WO 98/10088, published Mar. 12, 1998.

Preferably, the promoter used in the AAV packaging construct may be any of the constitutive, inducible or native promoters known to one of skill in the art or as discussed above. In one embodiment, an AAV p5 promoter sequence is employed. The selection of the AAV to provide any of these sequences does not limit the invention.

The spacer is an optional element in the design of the AAV packaging construct. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes that typically incorporate start/stop and polyA sites. The spacer may be a non-coding DNA sequence from a prokaryote or eukaryote, a repetitive non-coding sequence, a coding sequence without transcriptional controls or a coding sequence with transcriptional controls. Two exemplary sources of spacer sequences are the X phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell. The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, promoters, and other elements, including at least one translational start and stop signal, and the optional addition of polyadenylation sites.

3.2.4.5 AAV Accessory Functions

The host cell (or packaging cell) must also be rendered capable of providing non-AAV derived functions, or "accessory functions", in order to produce rAAV virions. Accessory functions are non-AAV derived viral and/or cellular functions upon which AAV is dependent for its replication. Thus, accessory functions include at least those non AAV proteins and RNAs that are required in AAV replication, including those involved in activation of AAV gene transcription, stage specific AAV mRNA splicing, AAV DNA replication, synthesis of rep and cap expression products and AAV capsid assembly.

Viral-based accessory functions can be derived from any of the known helper viruses.

Particularly, accessory functions can be introduced into and then expressed in host cells using methods known to those of skill in the art. Commonly, accessory functions are provided by infection of the host cells with an unrelated helper virus. A number of suitable helper viruses are known, including adenoviruses, Herpes viruses such as Herpes Simplex Virus types 1 and 2, and vaccinia viruses. Non-viral accessory functions will also find use herein, such as those provided by cell synchronization using any of various known agents [95-97]. Alternatively and preferentially, accessory functions can be provided using an accessory function vector construct. Accessory function vector constructs include nucleotide sequences that provide one or more accessory functions. An accessory function vector is capable of being introduced into a suitable host cell in order to support efficient AAV virion production in the host cell. Accessory function vectors can be in the form of a plasmid, phage, virus, transposon or cosmid. Accessory vector constructs can also be in the form of one or more linearized DNA or RNA fragments which, when associated with the appropriate control elements and enzymes, can be transcribed or expressed in a host cell to provide accessory functions.

Nucleic acid sequences providing the accessory functions can be obtained from natural sources, such as from the genome of adenovirus (especially Adenovirus serotype 5), or constructed using recombinant or synthetic methods known in the art. In this regard, adenovirus-derived accessory functions have been widely studied, and a number of adenovirus genes involved in accessory functions have been identified and partially characterized. See, e.g., Carter, B. J. (1990) "Adeno-Associated Virus Helper Functions," in CRC Handbook of Parvoviruses, vol. I (P. Tijssen, ed.), and [91]. Specifically, early adenoviral gene regions E1a, E2a, E4, VAI RNA and, possibly, E1b are thought to participate in the accessory process [98]. Herpes Virus-derived accessory functions have been described as well [99]. Vaccinia virus-derived accessory functions have also been described [95].

Most desirably, the necessary accessory functions are provided from an adenovirus source. In one embodiment, the host cell is provided with and/or contains an E1a gene product, an E1b gene product, an E2a gene product, and/or an E4 ORF6 gene product. The host cell may contain other adenoviral genes such as VAI RNA, but these genes are not required. In a preferred embodiment, no other adenovirus genes or gene functions are present in the host cell. The DNA sequences encoding the adenovirus E4 ORF6 genes and the E1 genes and/or E2a genes useful in this invention may be selected from among any known adenovirus type, including the presently identified 46 human types [see, e.g., American Type Culture Collection]. Similarly, adenoviruses known to infect other animals may supply the gene sequences. The selection of the adenovirus type for each E1, E2a, and E4 ORF6 gene sequence does not limit this invention. The sequences for a number of adenovirus serotypes, including that of serotype Ad5, are available from Genbank. A variety of adenovirus strains are available from the American Type Culture Collection (ATCC), Manassas, Va., or are available by request from a variety of commercial and institutional sources. Any one or more of human adenoviruses Types 1 to 46 may supply any of the adenoviral sequences, including E1, E2a, and/or E4 ORF6.

The adenovirus E1a, E1b, E2a, and/or E4 ORF6 gene products, as well as any other desired accessory functions, can be provided using any means that allows their expression in a cell. Each of the sequences encoding these products may be on a separate vector, or one or more genes may be on the same vector. The vector may be any vector known in the art or disclosed above, including plasmids, cosmids and viruses. Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

As a consequence of the infection of the host cell with a helper virus, or transfection of the host cell with an accessory function vector construct, accessory functions are expressed which transactivate the AAV packaging construct to produce AAV Rep and/or Cap proteins. The Rep expression products direct excision of the recombinant DNA (including the DNA of interest) from the AAV vector construct. The Rep proteins also serve to replicate the AAV genome. The expressed Cap proteins assemble into capsids, and the recombinant AAV genome is packaged into the capsids. Thus, productive AAV replication ensues, and the DNA is packaged into rAAV virions.

Following recombinant AAV replication, rAAV virions can be purified from the host cell using a variety of conventional purification methods, such as CsCl gradients or column purification. Further, if helper virus infection is employed to express the accessory functions, residual helper virus can be inactivated, using known methods. For example, adenovirus can be inactivated by heating to temperatures of approximately 60.degree. C. for, e.g., 20 minutes or more. This treatment selectively inactivates the helper virus which is heat labile, while preserving the rAAV which is heat stable. The resulting rAAV virions are then ready for use for DNA delivery to a variety of target cells.

3.2.4.6 In Vivo Delivery of rAAV Virions and Pharmaceutical Compositions

The present invention relates to a method for the transfer of nucleic acid compositions to the cells of an individual in general and to the transfer of RNAi expression cassettes in particular. The method comprises the step of contacting cells of said individual with rAAV-based gene transfer vectors which include at least one RNAi expression cassette, thereby delivering said RNAi expression cassette to the nucleus within said cells. The rAAV vectors are administered to the cells of said individual on an in vivo basis, i.e., the contact with the cells of the individual takes place within the body of the individual in accordance with the procedures which are most typically employed.

The rAAV virion is preferably suspended in a pharmaceutically acceptable delivery vehicle (i.e., physiologically compatible carrier), for administration to a human or non-human mammalian patient. Suitable carriers may be readily selected by one of skill in the art and may depend on the nature of the nucleic acid transfer vector chosen. Pharmaceutical compositions will comprise sufficient genetic material to produce a therapeutically effective amount of dsRNA complexes. The pharmaceutical compositions will also contain a pharmaceutically acceptable excipient. Such excipients include any pharmaceutical agent that does not itself induce an immune response harmful to the individual receiving the composition, and which may be administered without undue toxicity. Pharmaceutically acceptable excipients include,.but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. Other exemplary carriers include lactose, sucrose, calcium phosphate, gelatin, dextran, agar, pectin, peanut oil, sesame oil, and water. The selection of the carrier is not a limitation of the present invention. Optionally, the compositions of the invention may contain, in addition to the rAAV virions and carrier(s), other conventional pharmaceutical ingredients, such as preservatives, or chemical stabilizers. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin and albumin. A thorough discussion of pharmaceutically acceptable excipients is available in REMINGTON'S PHARMACEUTICAL SCIENCES (Mack Pub. Co., N.J. 1991).

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

In this invention, administering the instant pharmaceutical composition can be effected or performed using any of the various methods and delivery systems known to those skilled in the art. The administering can be performed, for example, intravenously, orally, via implant, transmucosally, transdermally, intramuscularly, and subcutaneously. In addition, the instant pharmaceutical compositions ideally contain one or more routinely used pharmaceutically acceptable carriers. Such carriers are well known to those skilled in the art. The following delivery systems, which employ a number of routinely used carriers, are only representative of the many embodiments envisioned for administering the instant composition.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Determining a therapeutically or prophylactically effective amount of the instant pharmaceutical composition can be done based on animal data using routine computational methods. Appropriate doses will depend, among other factors, on the specifics of the transfer vector chosen, on the route of administration, on the mammal being treated (e.g., human or non-human primate or other mammal), age, weight, and general condition of the subject to be treated, the severity of the cancer being treated, the location of the cancer being treated and the mode of administration. Thus, the appropriate dosage may vary from patient to patient. An appropriate effective amount can be readily determined by one of skill in the art. In one specific embodiment, the nucleic acid transfer vector is an AAV2/5 hybrid vector. A therapeutically effective human dosage for in vivo delivery of said vector according to the present invention is believed to be in the range of from about 20 to about 50 ml of saline solution containing concentrations of from about $10^{10}$ to $10^{14}$ functional vector/ml solution. The dosage will be adjusted to balance the therapeutic benefit against any side effects. In yet another embodiment, pharmaceutically effective dose of the rAAV is generally in the range of concentrations of from about $1 \times 10^5$ to $1 \times 10^{50}$ genomes rAAV, about $10^8$ to $10^{20}$ genomes rAAV, about $10^{10}$ to about $10^{16}$ genomes, or about $10^{11}$ to $10^{16}$ genomes rAAV. A preferred human dosage may be about $1 \times 10^{13}$ AAV genomes rAAV. Such concentrations may be delivered in about 0.001 ml to 100 ml, 0.05 to 50 ml, or 10 to 25 ml of a carrier solution. Other effective dosages can be readily established by one of ordinary skill in the art through routine trials establishing dose response curves.

Dosage treatment may be a single dose schedule or a multiple dose schedule. Moreover, the subject may be administered as many doses as appropriate. One of skill in the art can readily determine an appropriate number of doses. However, the dosage may need to be adjusted to take into consideration an alternative route of administration, or balance the therapeutic benefit against any side effects. Such dosages may vary depending upon the therapeutic application for which the recombinant vector is employed.

The vector particles are administered in sufficient amounts to enter the desired cells and to guarantee sufficient levels of functionality of the transferred nucleic acid composition to provide a therapeutic benefit without undue adverse, or with medically acceptable, physiological effects which can be determined by those skilled in the medical arts.

In some embodiments, conventional pharmaceutically acceptable routes of administration of rAAV may be combined. These routes include, but are not limited to, direct delivery to the liver, intravenous, intramuscular, subcutaneous, intradermal, oral and other parental routes of administration.

Optionally, in specific embodiments, rAAV-mediated delivery according to the invention may be combined with delivery by other viral and non-viral vectors. Such other viral vectors including, without limitation, adenoviral vectors, retroviral vectors, lentiviral vectors. herpes simplex virus (HSV) vectors, and baculovirus vectors may be readily selected and generated according to methods known in the art. Similarly, non-viral vectors, including, without limitation, liposomes, lipid-based vectors, polyplex vectors, molecular conjugates, polyamines and polycation vectors, may be readily selected and generated according to methods known in the art. When administered by these alternative routes, the dosage is desirable in the range described above.

In one embodiment, the route of administration is inhalation with lung cells as RNAi target cells. In that instance, when prepared for use as an inhalant: the pharmaceutical compositions are prepared as fluid unit doses using the rAAV and a suitable pharmaceutical vehicle for delivery by an atomizing spray pump, or by dry powder for insufflation. For use as aerosols, the rAAV can be packaged in a pressurized aerosol container together with a gaseous or liquefied propellant, for example, dichlorodifluormethane, carbon dioxide, nitrogen, propane, and the like, with the usual components such as cosolvents and wetting agents, as may be necessary or desirable. A pharmaceutical kit of said embodiment, desirably contains a container for oral or intranasal inhalation, which delivers a metered dose in one, two, or more actuations. Suitably, the kit also contains instructions for use of the spray pump or other delivery device, instructions on dosing, and an insert regarding the active agent (i.e., the transgene and/or rAAV). A single actuation of a pump spray or inhaler generally delivers contains in the range of about $10^5$ to about $10^{15}$ genome copies (GC), about $10^8$ to about $10^{12}$, and/or about $10^{10}$ GC, in a liquid containing 10 μg to 250 μg carrier, 25 μg to 100 μg, or 40 μg to 50 μg, carrier. Suitably, a dose is delivered in one or two actuations. However, other suitable delivery methods may be readily determined. The doses may be repeated daily, weekly, or monthly, for a predetermined length of time or as prescribed.

3.2.5 Pharmaceutical Preparations

In another aspect, the present invention provides pharmaceutical preparations comprising hedgehog antagonists. The hedgehog antagonists for use in the subject method may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the hedgehog antagonist, its use in the pharmaceutical preparation of the invention is contemplated. Suitable vehicles and their formulation inclusive of other proteins are described, for example, in the book Remington's Pharmaceutical Sciences (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the hedgehog antagonists suitable for veterinary uses, e.g., for the reatment of livestock or domestic animals, e.g., dogs.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a hedgehog antagonist at a particular target site.

The preparations of the present invention may be given orally, parenterally, topically, or rectally. They are, of course, given by forms suitable for each administration route. For example, they are administered in tablets or capsule form, by injection, inhalation, eye lotion, ointment, suppository, controlled release patch, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular hedgehog antagonist employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable and/or sterile carriers and can also be administered in conjunction with other antimicrobial agents such as penicillins, cephalosporins, aminoglycosides and glycopeptides. Conjunctive therapy thus includes sequential, simultaneous and separate administration of the active compound in a way that the therapeutic effects of the first administered one is not entirely disappeared when the subsequent is administered.

3.2.6 Pharmaceutical Composition

While it is possible for a therapeutic of the present invention to be administered alone, it is preferable to administer the therapeutic as a pharmaceutical formulation (composition). The hedgehog antagonists according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect by overcoming a hedgehog gain-of-function phenotype in at least a subpopulation of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present hedgehog antagonists may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like [149].

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation; with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, [149]). Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, α-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as a-, β-and ?-cyclodextrin, dimethyl-β cyclodextrin and 2-hydroxypropyl-β-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active hedgehog antagonist.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile, unsubstituted hydrocarbons, such as butane and propane.

Transdermal patches have the added advantage of providing controlled delivery of a compound of the present invention to the body. Such dosage forms can be made by dissolving or dispersing the hedgehog antagonists in the proper medium. Absorption enhancers can also be used to increase the flux of the hedgehog antagonists across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Oreg., U.S.A., 1977).

In any of the foregoing embodiment, the invention contemplates that the pharmaceutical preparations may be non-pyrogenic.

The pharmaceutical preparations for use in the methods of the present invention may comprise combinations of two or more hedgehog antagonists. For example, two hedgehog antibodies may be combined with a pharmaceutically acceptable carrier or excipient. The two antibodies may act additively or synergistically. In another example, one or more hedgehog antibodies may be combined with one or more non-antibody hedgehog antagonists (e.g., one or more small organic molecules), and with a pharmaceutically acceptable carrier or excipients. Said combination of hedgehog antagonists may act additively or synergistically.

3.3 BRIEF DESCRIPTIONS OF THE DRAWINGS

The present invention now will be described by way of illustrating but not limiting way, according to preferred embodiments thereof, with particular reference to the figures of the enclosed drawings, wherein:

FIG. 1 shows some representative examples of the chemical/structural formulas of steroidal alkaloids of the Veratrum type.

Figure 1:
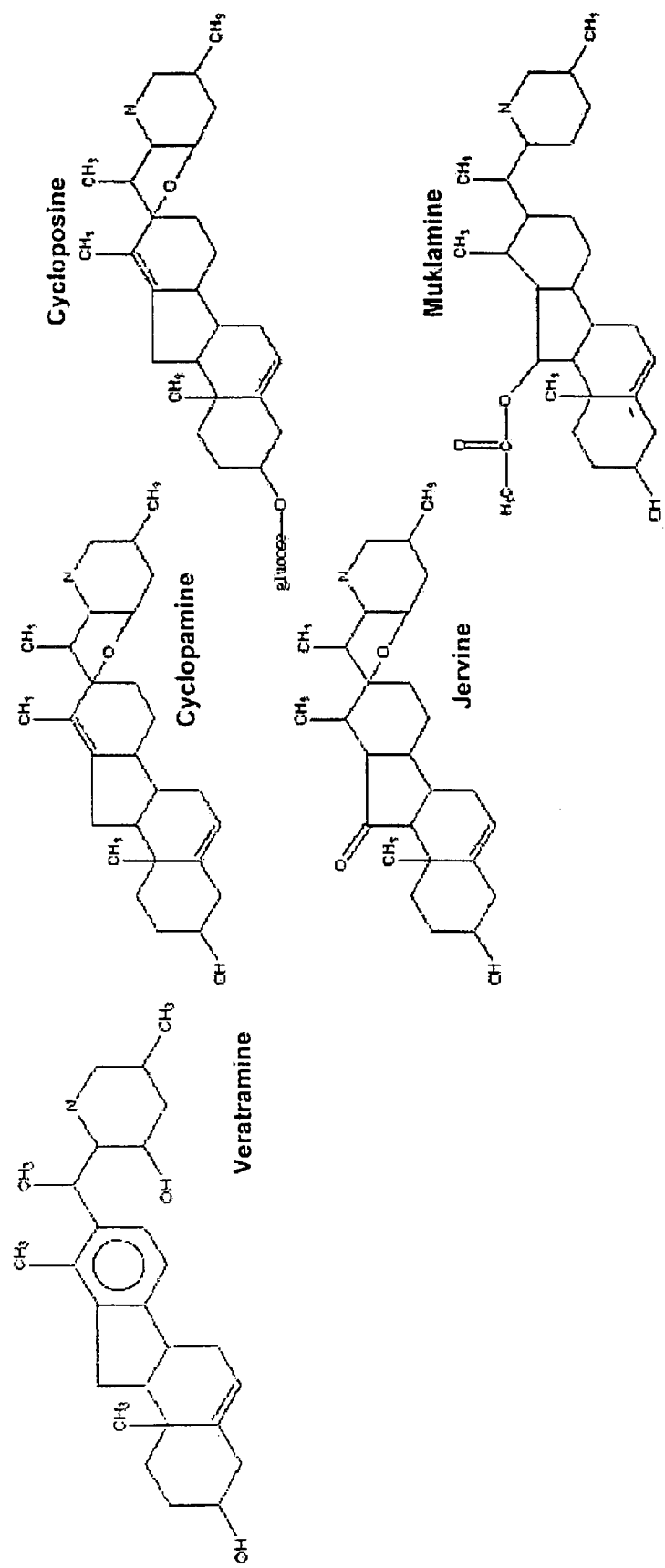
FIG. 1 shows
Figure 2:
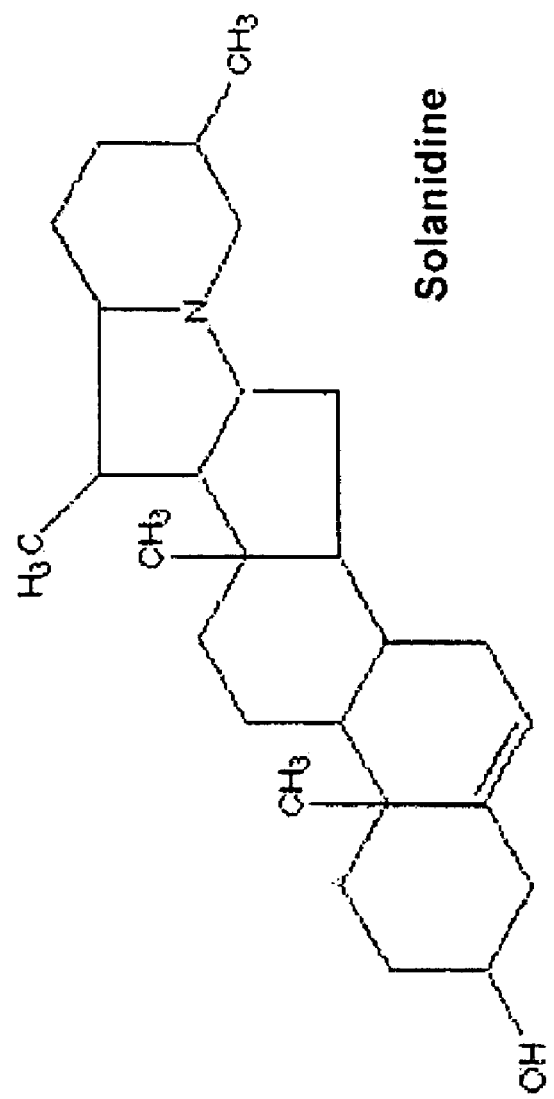
FIG. 2 shows a representative example of the chemical/structural formulas of steroidal alkaloids of the Solanum type.
Figure 3:
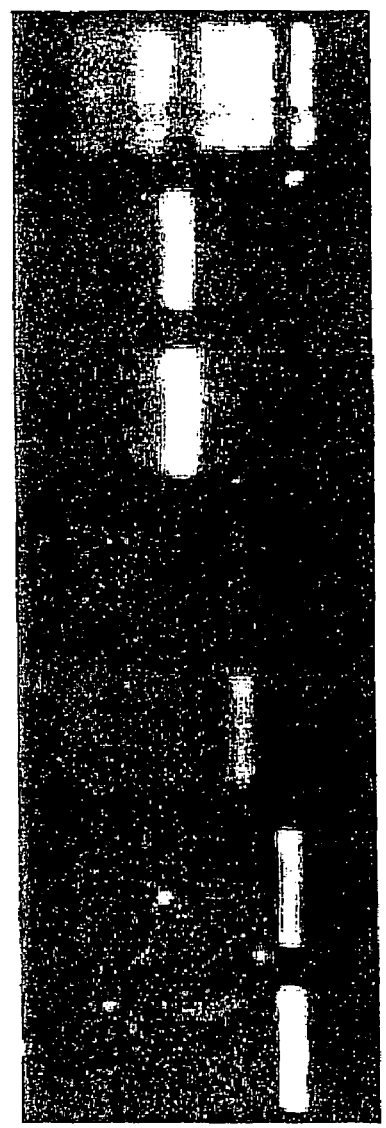
Figure 3:

FIG. 3 shows the result of an experiment where laser-induced CNV triggers the expression of Shh and Ptc. One can clearly see the upregulation of Shh (Shh CNV), Ptch (Ptch CNV), and VEGF (VEGF CNV) in laser-treated eyes (CNV) in comparison to control eyes (i.e., VEGF, Shh, Ptch). Actin functioned as an internal control.

Figure 4:
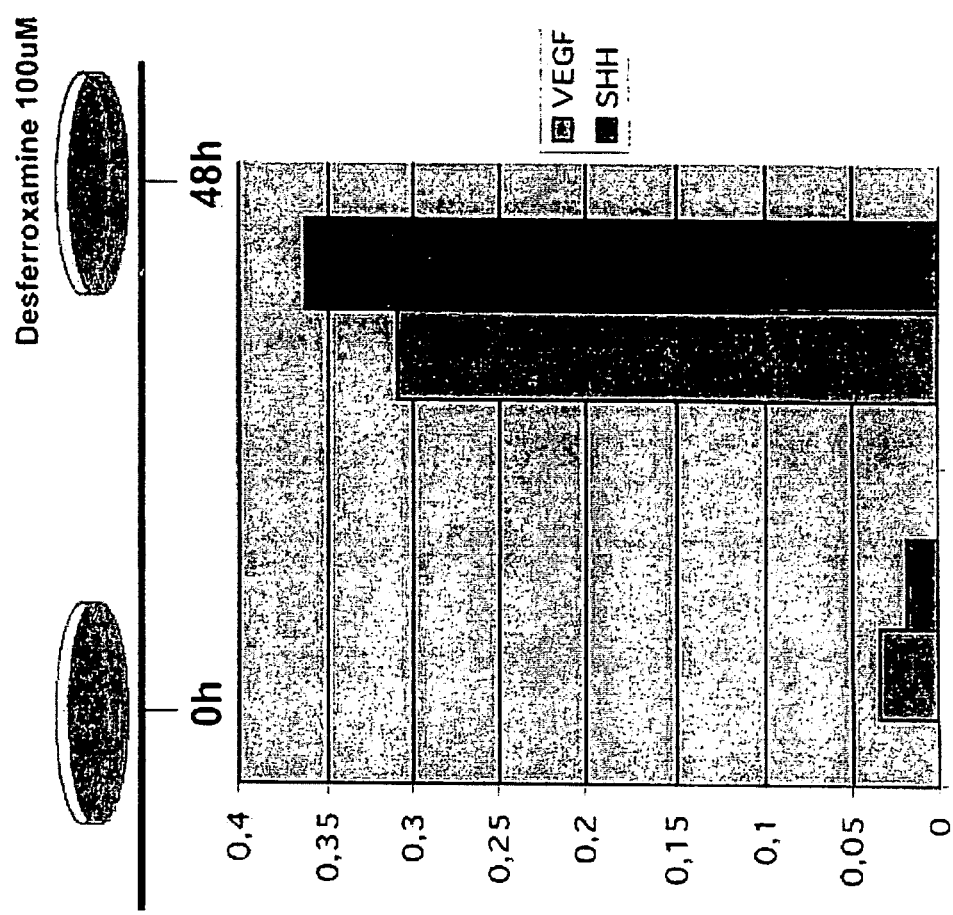

FIG. 4 shows the result of an experiment where hypoxia was induced in 293 cells (using desferroxamine), and the supernatant was tested twenty-four hours after induction for the presence of VEGF and Shh.

Figure 5:
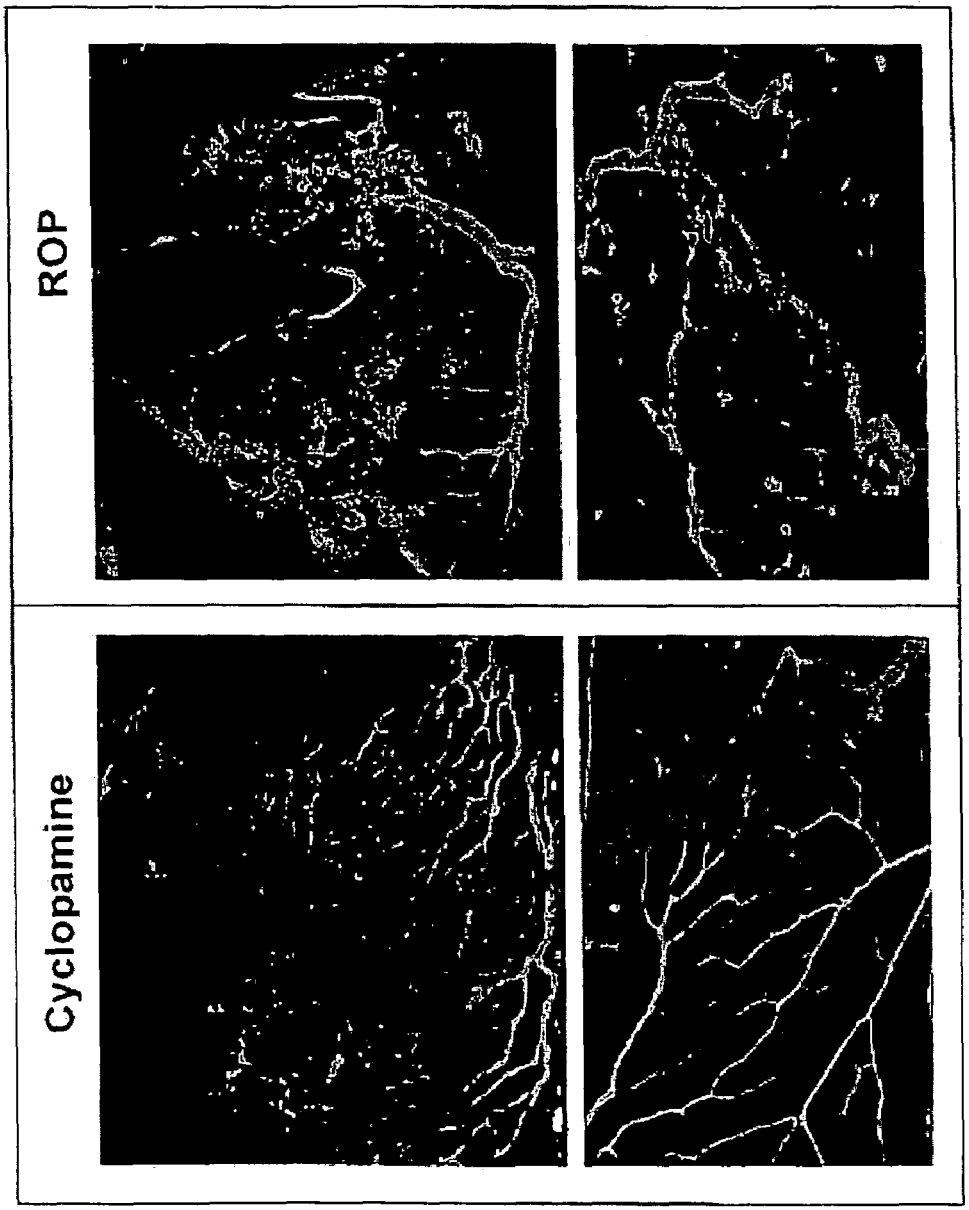

FIG. 5 shows the result of an angiography after fluorescein-dextran perfusion, where one group of "ROP" mice, a model of ocular neovascularization, was treated with cyclopamine ("Cyclopamine") and the other group ("ROP") was untreated. Robust inhibition of ocular neovascularization (decreased neovascular tufts and vessel leakage) was observed in all eyes injected with cyclopamine ("Cyclopamine"; FIG. 5 left) when compared with the control eyes ("ROP"; FIG. 5 right).

3.4 DETAILED DESCRIPTION OF THE PREFERRED EMBODIMENTS

The following paragraphs will provide a detailed description of the preferred embodiments.

3.4.1 EXAMPLE 1

Laser-Induced CNV Triggers the Expression of Shh and Ptc

To determine whether the Shh pathway is activated in experimental choroid neovascularization (CNV model), we performed RT-PCR analyses on laser treated, and control eyes.

We performed two independent experiments using two groups of animals of the same age (n=3). Choroidal neovascularization was induced in one eye by 20 burns around the entire surface of the retina using a diode laser. The contralateral eye was used as a control.

Three days after treatment retinas were harvested and pulled. Following RNA extraction, cDNA was synthesized and used as a template for semi-quantitative RT-PCR analysis. Shh was upregulated in laser-treated eyes in comparison to control eyes (FIG. 3: Laser-induced CNV triggers the expression of Shh and Ptc). Interestingly Ptc expression was also induced, implying that Ptc is a transcriptional target of Shh.

Semi-quantitative RT-PCR analysis was performed using Actin as a control. First-strand cDNA was synthesized from total RNA by reverse transcriptase (Stratagene, La Jolla, Calif., USA) using random primers. The cDNAs were amplified by PCR (94° C. for 1 minute, 58° C. for 1 minute 20 seconds, and 72° C. for 1 minute 15 seconds) using Taq DNA polymerase (Promega Corp., Madison, Wis., USA).

The reactions were carried out in the presence of the following pairs of specific primers:

```
SEQ ID NO: 9 (Shh forward primer):
5'GTG AGG CTGCGA GTG ACC G-3';

SEQ ID NO: 10 (Shh reverse primer):
5'-CCT GGT CGT CAG CCG CCA GCA CGC-3';

SEQ ID NO: 11 (Ptc forward primer):
5'-CTG CTG CTA TCC ATC AGC GT-3';

SEQ ID NO: 12 (Ptc reverse primer):
5'-AAG AAG GAT AAG AGG ACA GG-3'.
```

PCR products were electrophoresed on a 1.5% agarose gel and visualized by ethidium bromide.

As can be seen in FIG. 3, laser-induced CNV triggers the expression of Shh and Ptc. One can clearly see the upregulation of Shh (Shh CNV), Ptch (Ptch CNV), and VEGF (VEGF CNV) in laser-treated eyes (CNV) in comparison to control eyes (i.e., VEGF, Shh, Ptch). Actin functioned as an internal control.

3.4.2 EXAMPLE 2

Cyclopamine is Able to Inhibit Hypoxia-Induced VEGF Expression in HEK-293 Cells

To assess the ability of cyclopamine (purchased from Toronto Research Chemicals Inc. North York, ON, Canada) to inhibit VEGF protein expression induced in hypoxia, we added to the cell medium (10% Fetal Calf Serum FCS in DMEM) of 293 cells both desferroxamine (Sigma, St. Louis, Mo.) to a final concentration of 100 µM (to induce hypoxia) and Cyclopamine to a final concentration of 10 µM dissolved in 5 µl of 95% ethanol. Five µl of 95% ethanol was added to untreated control.

Twenty-four hours after induction of hypoxia the supernatant of the 293 cells was removed from wells and a human VEGF ELISA (R & D Systems, Minneapolis, Minn.) was performed on the cell supernatants (FIG. 4) as described in the Quantikine human VEGF ELISA protocol using a dilution of the medium of 1:10. ELISA results were read on a Bio-Rad Reader 550 ELISA plate reader (Bio-Rad Laboratories, Inc, CA).

As can be seen in FIG. 4, hypoxia induction resulted in the expression and secretion of both VEGF and Sonic Hedgehog in 293 cells.

3.4.3 EXAMPLE 3

Cyclopamine Administration to ROP Mice Results in Inhibition of Ocular Neovascularization To determine whether inhibition of the Shh signaling pathway is able to reduce retinal (ocular) neovascularization, Cyclopamine was administrated to a mouse model of Retinopathy of Prematurity (ROP).

C57/BL6 mice were used in this study. Mice from postnatal day 7 (P7) to P12 were exposed to hyperoxia (25% nitrogen, 75% oxygen). At P12 mice returned to room air until P17. The group of mice treated with cyclopamine received a daily subcutaneous injection of 50 mg/kg of the drug dissolved in 95% of ethanol and then mixed 1:4 in triolein (Sigma, St.

Louis, Mo.) in a final volume of 50 µl, from P12 to P17, controls received the vehicle alone.

On P17 angiography was performed: Mice were deeply anesthetized with Avertin and perfused with a solution containing fluorescein-dextran (50 mg/ml; 2 million molecular weight, Sigma, St. Louis, Mo.) in phosphate-buffered saline (PBS). Then, eyes were enucleated and fixed in paraformaldehyde, and the retinas were dissected, flat-mounted and viewed by fluorescence microscopy. Robust inhibition of ocular neovascularization (decreased neovascular tufts and vessel leakage) was observed in all eyes injected with cyclopamine when compared with the control eyes (FIG. 5).

3.4.4 EXAMPLE 4

AAV-Mediated Gene Transfer of Soluble Hip1 to ROP Mice Results in Inhibition of Ocular Neovascularization This example provides a rAAV virion comprising a nucleic acid composition that comprises a soluble Hip1 (sHIP1) minigene and AAV2 ITRs. Said rAAV virion is pseudotyped in a capsid of AAV serotype 2 (AAV2)—resulting in an AAV2/2 virion, referred to as AAV2/2 CMV sHIP1, encoded by AAV2 CMV sHIP1 (SEQ ID NO:7). The use of rAAV is particularly desirable, as it allows for long-term and high-level gene expression in the eye. The artisan will be able to reconstruct AAV2 CMV sHIP1 from the sequence information provided. Alternatively, the artisan can order a plasmid comprising the AAV2 CMV sHIP1 sequence from a commercial service such as—for example—Geneart Regensburg, Germany). Alternatively, the inventors will enable the practice of the invention by providing the AAV2 CMV sHIP1 plasmid or any other reagent that is not commercially available within 4 weeks upon request.

The sHIP1 sequence was cloned using PCR with mouse cDNA retina as a template. The primers were designed to amplify the sequence from the Hip1 start codon up to the deletion of the last 22 amino acids at the C-terminus. The primers include the cloning sites (NotI on the 5' site, BamHI on the 3' site); their sequence is listed in SEQ ID NO:13 (forward primer) and SEQ ID NO:14 (reverse primer).

sHip1 secretion from the transduced target cells is achieved by transducing said target cells with a gene transfer vector comprising a nucleic acid composition which comprises the sHip1 coding sequence and all the regulatory sequences necessary for its transcription and translation in said target cells with said target cells being eye cells such as—for example—retinal pigment epithelium cells. In this embodiment, expression is driven by a CMV promoter/enhancer, and a bovine growth hormone polyadenylation signal is used to terminate transcription.

Vector is administered via subretinal injection at a dose of $10^{10}$ genomic particles. Alternatively, vector can also be administered via intravitreal injection.

As a control, a rAAV virion expressing lacZ as transgene (AAV 2/2 CMV lacZ) is used as lacZ does not possess anti-angiogenic activity. The sequence and cloning of AAV2 CMV lacZ has been described in prior art [71].

Both AAV2/2 CMV sHIP1 and AAV2/2 CMV lacZ are prepared by triple transfection and purified by $CsCl_2$ gradients as described herein and in prior art [71]. Physical titers are assessed by Real Time PCR.

To determine whether inhibition of the Shh signaling pathway through expression and secretion of soluble Hip1 is able to reduce retinal (ocular) neovascularization, AAV2/2 CMV sHIP1 and AAV2/2 CMV lacZ are administrated to a mouse model of Retinopathy of Prematurity (ROP), respectively.

10 C57/BL6 mice are used in this study. Mice from postnatal day 7 (P7) to P12 are exposed to hyperoxia (25% nitrogen, 75% oxygen). At P12 mice return to room air until P17. The group of mice to be treated with AAV 2/2 CMV sHIP1 (5 mice) receives $10^{10}$ genomic particles of AAV 2/2 CMV sHIP1 in a final volume of 50 µl at day P3, the control group of mice (5 mice) receives the same amount of genomic particles of AAV 2/2 CMV lacZ in a final volume of f 50 µl at day P3. Vector is administered by subretinal injection.

On P17 angiography are performed: Mice are deeply anesthetized with Avertin and perfused with a solution containing fluorescein-dextran (50 mg/ml; 2 million molecular weight, Sigma, St. Louis, Mo.) in phosphate-buffered saline (PBS). Then, eyes are enucleated and fixed in paraformaldehyde, and the retinas are dissected, flat-mounted and viewed by fluorescence microscopy. Robust inhibition of ocular neovascularization (decreased neovascular tufts and vessel leakage) is observed in all eyes injected with AAV 2/2 CMV sHIP1 when compared with the control ("lacZ") eyes.

3.4.5 EXAMPLE 5

Administration of Soluble Hip1 to ROP Mice Results in Inhibition of Ocular Neovascularization Soluble Hip1 is produced as follows: 293 cells are transfected with AAV2 CMV sHIP1 using the $CsCl_2$ method. Three days upon transfection, supernatant is harvested and filtered through a 22-µm filter to remove cell debris. To purify soluble Hip1, the supernatant is passed through an affinity column with covalently attached polyclonal rabbit-anti-Hip1 antibodies. Hip1 is eluted with 15 ml of PBS, pH7.4, plus 0.4M NaCl. The eluate is concentrated to about 0.5 ml with a Millipore Biomax-100K NMWL filter device (UFV2BHK40) by centrifugation. To adjust the NaCl concentration to physiological levels, the filter device is refilled with PBS, pH 7.4, and the soluble Hip1 is concentrated to 0.5 ml again. After removal of the target-protein-containing solution, the membrane of the filter device is washed three times with 100 µl of PBS, pH 7.4, which is then added to the other part.

To determine whether inhibition of the Shh signaling pathway by administration of soluble Hip1 is able to reduce retinal (ocular) neovascularization, soluble Hip1 is administrated to a mouse model of Retinopathy of Prematurity (ROP).

C57/BL6 mice are used in this study. Mice from postnatal day 7 (P7) to P12 are exposed to hyperoxia (25% nitrogen, 75% oxygen). At P12 mice return to room air until P17. The group of five mice treated with soluble Hip1 received a daily subretinal injection of 50 mg/kg of soluble Hip1 dissolved in Phosphate-Buffered Saline (PBS) from P12 to P17, controls receive the vehicle alone.

On P17 angiography is performed: Mice are deeply anesthetized with Avertin and perfused with a solution containing fluorescein-dextran (50 mg/ml; 2 million molecular weight, Sigma, St. Louis, Mo.) in Phosphate-Buffered Saline (PBS). Then, eyes are enucleated and fixed in paraformaldehyde, and the retinas are dissected, flat-mounted and viewed by fluorescence microscopy. Robust inhibition of ocular neovascularization (decreased neovascular tufts and vessel leakage) is observed in all eyes injected with soluble Hip1 when compared with the control eyes.

3.4.6 EXAMPLE 6

Administration of an siRNA Targeting Sonic Hedgehog to ROP Mice Results in Inhibition of Ocular Neovascularization The siRNA targeting Sonic Hedgehog is ordered from a commercial vendor (Qiagen GmbH, Hilden, Germany) according to our specifications: The siRNA duplex is represented in SEQ ID NO:16 (sense strand) and SEQ ID NO:15 (antisense strand), wherein the sense and antisense RNA strands form an RNA duplex. The sense and antisense strand are ordered pre-annealed.

To determine whether inhibition of the Shh signaling pathway by administration of an siRNA targeting Shh is able to reduce retinal (ocular) neovascularization, siRNA targeting Shh is administrated to a mouse model of Retinopathy of Prematurity (ROP).

C57/BL6 mice are used in this study. Mice from postnatal day 7 (P7) to P12 are exposed to hyperoxia (25% nitrogen, 75% oxygen). At P12 mice return to room air until P17. The group of five mice treated with siRNA targeting Shh receive a daily subretinal injection (1 µl) of 100 mg/ml siRNA targeting Shh dissolved in Phosphate-Buffered Saline (PBS) from P12 to P17, controls receive the vehicle alone.

On P17 angiography is performed: Mice are deeply anesthetized with Avertin and perfused with a solution containing fluorescein-dextran (50 mg/ml; 2 million molecular weight, Sigma, St. Louis, Mo.) in Phosphate-Buffered Saline (PBS). Then, eyes are enucleated and fixed in paraformaldehyde, and the retinas are dissected, flat-mounted and viewed by fluorescence microscopy. Robust inhibition of ocular neovascularization (decreased neovascular tufts and vessel leakage) is observed in all eyes injected with siRNA targeting Shh when compared with the control eyes.

To summarize: A small interfering RNA targeting Sonic Hedgehog is injected into the eye of a mammalian subject. One variant of an siRNA targeting human and mouse Sonic Hedgehog is represented in SEQ ID NO:16 (sense strand) and SEQ ID NO:15 (antisense strand), wherein the sense and antisense RNA strands form an RNA duplex. The sense and antisense strand can be purchased already annealed (i.e., in duplex form) from commercial vendors such as Qiagen GmbH, Hilden, Germany. Many different siRNAs can be designed to target Sonic Hedgehog. Theoretically, each 19 to 25 nucleotide stretch within the Sonic Hedgehog gene can be used as design template for an siRNA. The exact method, design (e.g., stem-loop vs. annealed duplex) and sequence of the siRNA targeting Sonic Hedgehog should not limit the scope of the present invention. When administering the siRNA targeting Sonic Hedgehog in a sufficient amount, Shh translation and secretion will be inhibited, thus preventing the activation of the Hedgehog signaling pathway to the extent that ocular neovascularization will be prevented.

Preferably, the siRNA of the invention is chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

3.4.7 EXAMPLE 7

Administration of an siRNA Targeting Smoothened to ROP Mice Results in Inhibition of Ocular Neovascularization The siRNA targeting Smoothened is ordered from a commercial vendor (Qiagen GmbH, Hilden, Germany) according to our specifications: The siRNA duplex is represented in SEQ ID NO:17 (sense strand) and SEQ ID NO:18 (antisense strand), wherein the sense and antisense RNA strands form an RNA duplex. The sense and antisense strand are ordered pre-annealed.

To determine whether inhibition of the Shh signaling pathway by administration of an siRNA targeting Smoothened is able to reduce retinal (ocular) neovascularization, siRNA targeting Shh is administrated to a mouse model of Retinopathy of Prematurity (ROP).

C57/BL6 mice are used in this study. Mice from postnatal day 7 (P7) to P12 are exposed to hyperoxia (25% nitrogen, 75% oxygen). At P12 mice return to room air until P17. The group of five mice treated with siRNA targeting Smoothened receive a daily subretinal injection (1 µl) 100 mg/ml of siRNA targeting Smoothened dissolved in Phosphate-Buffered Saline (PBS) from P12 to P17, controls receive the vehicle alone.

On P17 angiography is performed: Mice are deeply anesthetized with Avertin and perfused with a solution containing fluorescein-dextran (50 mg/ml; 2 million molecular weight, Sigma, St. Louis, Mo.) in Phosphate-Buffered Saline (PBS). Then, eyes are enucleated and fixed in paraformaldehyde, and the retinas are dissected, flat-mounted and viewed by fluorescence microscopy. Robust inhibition of ocular neovascularization (decreased neovascular tufts and vessel leakage) is observed in all eyes injected with siRNA targeting Smoothened when compared with the control eyes.

To summarize: A small interfering RNA targeting Smoothened is injected into the eye of a mammalian subject. One variant of an siRNA targeting human and mouse Smoothened is represented in SEQ ID NO:17 (sense strand) and SEQ ID NO:18 (antisense strand), wherein the sense and antisense RNA strands form an RNA duplex. The sense and antisense strand can be purchased already annealed (i.e., in duplex form) from commercial vendors such as Qiagen GmbH, Hilden, Germany. Many different siRNAs can be designed to target Smoothened. Theoretically, each 19 to 25 nucleotide stretch within the Smoothened gene can be used as design template for an siRNA. The exact method, design (e.g., stem-loop vs. annealed duplex) and sequence of the siRNA targeting Smoothened should not limit the scope of the present invention. When administering the siRNA targeting Smoothened in a sufficient amount, Smoothened translation and expression will be inhibited, thus preventing the activation of the Hedgehog signaling pathway to the extent that ocular neovascularization will be prevented.

Preferably, the siRNA of the invention is chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

3.4.8 EXAMPLE 8

Administration of an siRNA Targeting Gli1 to ROP Mice Results in Inhibition of Ocular Neovascularization The siRNA targeting Gli1 is ordered from a commercial vendor (Qiagen GmbH, Hilden, Germany) according to our specifications: The siRNA duplex is represented in SEQ ID NO:19 (sense strand) and SEQ ID NO:20 (antisense strand), wherein the sense and antisense RNA strands form an RNA duplex. The sense and antisense strand are ordered pre-annealed.

To determine whether inhibition of the Shh signaling pathway by administration of an siRNA targeting Gli1 is able to reduce retinal (ocular) neovascularization, siRNA targeting Shh is administrated to a mouse model of Retinopathy of Prematurity (ROP).

C57/BL6 mice are used in this study. Mice from postnatal day 7 (P7) to P12 are exposed to hyperoxia (25% nitrogen, 75% oxygen). At P12 mice return to room air until P17. The group of five mice treated with siRNA targeting Gli1 receive a daily subretinal injection (1 μl) of 100 mg/ml siRNA targeting Gli1 dissolved in Phosphate-Buffered Saline (PBS) from P12 to P17, controls receive the vehicle alone.

On P17 angiography is performed: Mice are deeply anesthetized with Avertin and perfused with a solution containing fluorescein-dextran (50 mg/ml; 2 million molecular weight, Sigma, St. Louis, Mo.) in Phosphate-Buffered Saline (PBS). Then, eyes are enucleated and fixed in paraformaldehyde, and the retinas are dissected, flat-mounted and viewed by fluorescence microscopy. Robust inhibition of ocular neovascularization (decreased neovascular tufts and vessel leakage) is observed in all eyes injected with siRNA targeting Gli1 when compared with the control eyes.

To summarize: A small interfering RNA targeting Gli1 is injected into the eye of a mammalian subject. One variant of an siRNA targeting human and mouse Gli1 is represented in SEQ ID NO:19 (sense strand) and SEQ ID NO:20 (antisense strand), wherein the sense and antisense RNA strands form an RNA duplex. The sense and antisense strand can be purchased already annealed (i.e., in duplex form) from commercial vendors such as Qiagen GmbH, Hilden, Germany. Many different siRNAs can be designed to target Gli1. Theoretically, each 19 to 25 nucleotide stretch within the Gli1 gene can be used as design template for an siRNA. The exact method, design (e.g., stem-loop vs. annealed duplex) and sequence of the siRNA targeting Gli1 should not limit the scope of the present invention. When administering the siRNA targeting Gli1 in a sufficient amount, Gli1 translation and expression will be inhibited, thus preventing the activation of the Hedgehog signaling pathway to the extent that ocular neovascularization will be prevented.

Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

3.4.9 Other Embodiments

In some embodiments, a monoclonal antibody against Hedgehog is injected into the eye of a mammalian subject. In one subset of said embodiments, the 5E1 monoclonal antibody is injected in the eye of a mouse to prevent choroidal neovascularization in the CNV mouse model. Said antibody binds to Hedgehog and thus prevents binding of Hedgehog to its receptor, Ptc-1. This in turn prevents ocular neovascularization.

In yet other embodiments, a soluble form of Hip1 is injected into the eye of a mammalian subject. One variant of a soluble form of Hip1 is represented in SEQ ID NO:6. There are many different ways of creating a soluble version of Hip1. All ways have in common that the transmembrane domain of Hip1 is removed, which enables secretion of Hip1. The exact method and sequence of the soluble Hip1 variant should not limit the scope of the present invention. Moreover, any homologous protein to the soluble form of Hip1 (SEQ ID NO:6) should also fall within the scope of the present invention. The soluble Hip1 variant is still able to bind and thus sequester Hedgehog. In other words: The soluble Hip1 variant competes with the Hedgehog receptor Ptc1 for Hedgehog binding. When administering the soluble Hip1 variant in excess, the soluble Hip1 variants sequester a sufficient amount of free Hedgehog to prevent activation of the Hedgehog signaling pathway to the extent that ocular neovascularization will be prevented. In one subset of said embodiments, the soluble variant of Hip1 is pegylated.

In yet other embodiments, a soluble variant of Hip1 is expressed within the mammalian subject. This is achieved by administering to said subject a gene transfer vector encoding said soluble Hip1 variant. Thus, the soluble Hip1 variant is expressed and secreted from cells of said mammalian subject. The secreted Hip1 variants are then able to locally sequester Hedgehog, thus preventing activation of the Hedgehog signaling pathway, which—in the end—will prevent, inhibit, and/or reverse ocular neovascularization.

3.4.10 Preferred Embodiment

In its preferred embodiment, cyclopamine is administered to a mammalian subject in general, and to a human being in particular, by subcutaneous injection at a concentration of 50 mg/ kg. The drug is dissolved in 95% of ethanol and then mixed 1:4 in triolein. Alternatively, one of skill in the art will be able to formulate cyclopamine also in eye drops.

Furthermore, in its preferred embodiment, the Hedgehog-signaling interfering substance is administered to a mammalian subject affected by the wet form of AMD.

Cyclopamine binds to and thus inhibits Smo activation, thus interfering with the Hedgehog-signaling pathway. This in turn inhibits, prevents and/or reverses ocular neovascularization, which is involved in the pathology of wet AMD.

Although the present invention has been described with reference to specific embodiments and examples, numerous modifications and variations can be made and still the result will come within the scope of the invention. No limitation with respect to the specific embodiments disclosed herein is intended or should be inferred.

3. Prior Art

U.S. Patent applications

| U.S. patent application | Inventor: Title |
| --- | --- |
| 20040110663 | Dudek et al.: Hedgehog antagonists, methods and uses related thereto |
| 20040060568 | Dudek et al.: Hedgehog antagonists, methods and uses related thereto |
| 20040048282 | Smolyar: Regulation of human patched-like protein |
| 20040030099 | Smolyar: Regulation of human patched-like protein |
| 20040023949 | Baxter et al.: Mediators of hedgehog signaling pathways, compositions and uses related thereto |
| 20030022819 | Ling et al.: Angiogenesis-modulating compositions and use |
| 20040161798 | xxx |

U.S. Patents

| U.S. Patent | Inventor: Title |
| --- | --- |
| 6,713,065 | Baron et al.: Methods of using hedgehog proteins to modulate hematopoiesis and vascular growth |
| 6,552,016 | Baxter et al.: Mediators of hedgehog signaling pathways, compositions and uses related thereto |
| 6,686,388 | Dudek et al.: Regulators of the hedgehog pathway, compositions and uses related thereto |
| 6,683,108 | Baxter et al.: Agonists of hedgehog signaling pathways and uses related thereto |
| 6,639,051 | Wang et al.: Regulation of epithelial tissue by hedgehog-like polypeptides, and formulations and uses related thereto |
| 6,605,700 | Bumcrot: Human patched genes and proteins, and uses related thereto |
| 6,552,016 | Baxter et al.: Mediators of hedgehog signaling pathways, compositions and uses related thereto |
| 6,468,978 | Esswein et al.: Active hedgehog protein conjugate |
| 6,309,879 | Bumcrot: Human patched genes and proteins, and uses related thereto |
| 6,291,516 | Dudek et al.: Regulators of the hedgehog pathway, compositions and uses related thereto |
| 6,432,970 | Beachy et al.: Inhibitors of hedgehog signaling pathways, compositions and uses related thereto |

-continued

| U.S. Patent | Inventor: Title |
| --- | --- |
| 6,291,516 | Dudek et al.: Regulators of the hedgehog pathway, compositions and uses related thereto |
| 6,288,048 | Beachy et al.: Cholesterol and hedgehog signaling |
| 6,057,091 | Beachy et al.: Method of identifying compounds affecting hedgehog cholesterol transfer |
| 5,891,875 | Hipskind et al.: Morpholinyl tachykinin receptor antagonists |
| 5,260,210 | Rubin et al.: Blood-brain barrier model |
| 5,795,756 | Johnson et al.: Method and compounds for the inhibition of adenylyl cyclase |
| 4,874,702 | Fiers et al.: Vectors and methods for making such vectors and for expressive cloned genes |
| 5,258,498 | Huston et al.: Polypeptide linkers for production of biosynthetic proteins |
| 5,482,858 | Huston et al.: Polypeptide linkers for production of biosynthetic proteins |
| 5,091,513 | Huston et al.: Biosynthetic antibody binding sites |
| 4,946,778 | Ladner et al.: Single polypeptide chain binding molecules |
| 5,969,108 | McCafferty et al.: Methods for producing members of specific binding pairs |
| 5,871,907 | Winter et al.: Methods for producing members of specific binding pairs |
| 5,223,409 | Ladner et al.: Directed evolution of novel binding proteins |
| 5,225,539 | Winter: Recombinant altered antibodies and methods of making altered antibodies |
| 5,411,941 | Grinna et al.: Heterodimeric osteogenic factor |
| 5,798,230 | Bornkamm et al.: Process for the preparation of human monoclonal antibodies and their use |
| 5,789,650 | Lonberg et al.: Transgenic non-human animals for producing heterologous antibodies |
| 5,693,762 | Queen et al.: Humanized immunoglobulins |
| 5,693,761 | Queen et al.: Polynucleotides encoding improved humanized immunoglobulins |
| 5,585,089 | Queen et al.: Humanized immunoglobulins |
| 5,530,101 | Queen et al.: Humanized immunoglobulins |
| 5,176,996 | Hogan et al.: Method for making synthetic oligonucleotides which bind specifically to target sites on duplex DNA molecules, by forming a colinear triplex, the synthetic oligonucleotides and methods of use |
| 5,264,564 | Matteucci: Oligonucleotide analogs with novel linkages |
| 5,256,775 | Froehler: Exonuclease-resistant oligonucleotides |

-continued

| U.S. Patent | Inventor: Title |
|---|---|
| 5,093,246 | Cech et al.: RNA ribozyme polymerases, dephosphorylases, restriction endoribonucleases and methods |
| 5,658,785 | Johnson: Adeno-associated virus materials and methods |
| 5,139,941 | Muzyczka et al.: AAV transduction vectors |

Other patents

| Patent | Title |
|---|---|
| WO9952534A1 | Use of steroidal alkaloid derivatives as inhibitors of hedgehog signaling pathways |

Prior Art Publications
Prior Art Publications:
1. Ingham, P. W., Signalling by hedgehog family proteins in *Drosophila* and vertebrate development. Curr Opin Genet Dev, 1995. 5(4): p. 492-8.
2. Perrimon, N., Hedgehog and beyond. Cell, 1995. 80(4): p. 517-20.
3. Hammerschmidt, M., Brook, A., and McMahon, A. P., The world according to hedgehog. Trends Genet, 1997. 13(1): p. 14-21.
4. Ericson, J., Muhr, J., Jessell, T. M., and Edlund, T., Sonic hedgehog: a common signal for ventral patterning along the rostrocaudal axis of the neural tube. Int J Dev Biol, 1995. 39(5): p. 809-16.
5. Ericson, J., Muhr, J., Placzek, M., Lints, T., Jessell, T. M., and Edlund, T., Sonic hedgehog induces the differentiation of ventral forebrain neurons: a common signal for ventral patterning within the neural tube. Cell, 1995. 81(5): p. 747-56.
6. Roberts, D. J., Johnson, R. L., Burke, A. C., Nelson, C. E., Morgan, B. A., and Tabin, C., Sonic hedgehog is an endodermal signal inducing Bmp-4 and Hox genes during induction and regionalization of the chick hindgut. Development, 1995. 121(10): p. 3163-74.
7. Apelqvist, A., Ahlgren, U., and Edlund, H., Sonic hedgehog directs specialised mesoderm differentiation in the intestine and pancreas. Curr Biol, 1997. 7(10): p. 801-4.
8. Dodd, J., Jessell, T. M., and Placzek, M., The when and where of floor plate induction. Science, 1998. 282(5394): p. 1654-7.
9. Dockter, J. L., Sclerotome induction and differentiation. Curr Top Dev Biol, 2000. 48: p. 77-127.
10. Bitgood, M. J. and McMahon, A. P., Hedgehog and Bmp genes are coexpressed at many diverse sites of cell-cell interaction in the mouse embryo. Dev Biol, 1995. 172(1): p. 126-38.
11. Chiang, C., Litingtung, Y., Lee, E., Young, K. E., Corden, J. L., Westphal, H., and Beachy, P. A., Cyclopia and defective axial patterning in mice lacking Sonic hedgehog gene function. Nature, 1996. 383(6599): p. 407-13.
12. Litingtung, Y., Lei, L., Westphal, H., and Chiang, C., Sonic hedgehog is essential to foregut development. Nat Genet, 1998. 20(1): p. 58-61.
13. St-Jacques, B., Dassule, H. R., Karavanova, I., Botchkarev, V. A., Li, J., Danielian, P. S., McMahon, J. A., Lewis, P. M., Paus, R., and McMahon, A. P., Sonic hedgehog signaling is essential for hair development. Curr Biol, 1998. 8(19): p. 1058-68.
14. St-Jacques, B., Hammerschmidt, M., and McMahon, A. P., Indian hedgehog signaling regulates proliferation and differentiation of chondrocytes and is essential for bone formation. Genes Dev, 1999. 13(16): p. 2072-86.
15. Karp, S. J., Schipani, E., St-Jacques, B., Hunzelman, J., Kronenberg, H., and McMahon, A. P., Indian hedgehog coordinates endochondral bone growth and morphogenesis via parathyroid hormone related-protein-dependent and-independent pathways. Development, 2000. 127(3): p. 543-8.
16. Bitgood, M. J., Shen, L., and McMahon, A. P., Sertoli cell signaling by Desert hedgehog regulates the male germline. Curr Biol, 1996. 6(3): p. 298-304.
17. Parmantier, E., Lynn, B., Lawson, D., Turmaine, M., Namini, S. S., Chakrabarti, L., McMahon, A. P., Jessen, K. R., and Mirsky, R., Schwann cell-derived Desert hedgehog controls the development of peripheral nerve sheaths. Neuron, 1999. 23(4): p. 713-24.
18. Ding, Q., Fukami, S., Meng, X., Nishizaki, Y., Zhang, X., Sasaki, H., Dlugosz, A., Nakafuku, M., and Hui, C., Mouse suppressor of fused is a negative regulator of sonic hedgehog signaling and alters the subcellular distribution of Gli1. Curr Biol, 1999. 9(19): p. 1119-22.
19. Murone, M., Rosenthal, A., and de Sauvage, F. J., Hedgehog signal transduction: from flies to vertebrates. Exp Cell Res, 1999. 253(1): p. 25-33.
20. Murone, M., Rosenthal, A., and de Sauvage, F. J., Sonic hedgehog signaling by the patched-smoothened receptor complex. Curr Biol, 1999. 9(2): p. 76-84.
21. Pearse, R. V., 2nd, Collier, L. S., Scott, M. P., and Tabin, C. J., Vertebrate homologs of *Drosophila* suppressor of fused interact with the gli family of transcriptional regulators. Dev Biol, 1999. 212(2): p. 323-36.
22. Stone, D. M., Murone, M., Luoh, S., Ye, W., Armanini, M. P., Gurney, A., Phillips, H., Brush, J., Goddard, A., de Sauvage, F. J., and Rosenthal, A., Characterization of the human suppressor of fused, a negative regulator of the zinc-finger transcription factor Gli. J Cell Sci, 1999. 112 (Pt 23): p. 4437-48.
23. Hynes, M., Ye, W., Wang, K., Stone, D., Murone, M., Sauvage, F., and Rosenthal, A., The seven-transmembrane receptor smoothened cell-autonomously induces multiple ventral cell types. Nat Neurosci, 2000. 3(1): p. 41-6.
24. Bai, C. B., Auerbach, W., Lee, J. S., Stephen, D., and Joyner, A. L., Gli2, but not Gli1, is required for initial Shh signaling and ectopic activation of the Shh pathway. Development, 2002. 129(20): p. 4753-61.
25. Bai, C. B. and Joyner, A. L., Gli1 can rescue the in vivo function of Gli2. Development, 2001. 128(24): p. 5161-72.
26. Brewster, R., Lee, J., and Ruiz i Altaba, A., Gli/Zic factors pattern the neural plate by defining domains of cell differentiation. Nature, 1998. 393(6685): p. 579-83.
27. Brewster, R., Mullor, J. L., and Ruiz i Altaba, A., Gli2 functions in FGF signaling during antero-posterior patterning. Development, 2000. 127(20): p. 4395-405.
28. Buttitta, L., Mo, R., Hui, C. C., and Fan, C. M., Interplays of Gli2 and Gli3 and their requirement in mediating Shh-dependent sclerotome induction. Development, 2003. 130 (25): p. 6233-43.
29. Dunaeva, M., Michelson, P., Kogerman, P., and Toftgard, R., Characterization of the physical interaction of Gli proteins with SUFU proteins. J Biol Chem, 2003. 278(7): p. 5116-22.

30. Kalderon, D., Hedgehog signaling: Costal-2 bridges the transduction gap. Curr Biol, 2004. 14(2): p. R67-9.
31. Lum, L., Zhang, C., Oh, S., Mann, R. K., von Kessler, D. P., Taipale, J., Weis-Garcia, F., Gong, R., Wang, B., and Beachy, P. A., Hedgehog signal transduction via Smoothened association with a cytoplasmic complex scaffolded by the atypical kinesin, Costal-2. Mol Cell, 2003. 12(5): p. 1261-74.
32. Merchant, M., Vajdos, F. F., Ultsch, M., Maun, H. R., Wendt, U., Cannon, J., Desmarais, W., Lazarus, R. A., de Vos, A. M., and de Sauvage, F. J., Suppressor of fused regulates Gli activity through a dual binding mechanism. Mol Cell Biol, 2004. 24(19): p. 8627-41.
33. Monnier, V., Dussillol, F., Alves, G., Lamour-Isnard, C., and Plessis, A., Suppressor of fused links fused and Cubitus interruptus on the hedgehog signalling pathway. Curr Biol, 1998. 8(10): p. 583-6.
34. Bak, M., Hansen, C., Tommerup, N., and Larsen, L. A., The Hedgehog signaling pathway—implications for drug targets in cancer and neurodegenerative disorders. Pharmacogenomics, 2003. 4(4): p. 411-29.
35. Bale, A. E., Hedgehog signaling and human disease. Annu Rev Genomics Hum Genet, 2002. 3: p. 47-65.
36. Matise, M. P. and Joyner, A. L., Gli genes in development and cancer. Oncogene, 1999. 18(55): p. 7852-9.
37. Taipale, J. and Beachy, P. A., The Hedgehog and Wnt signalling pathways in cancer. Nature, 2001. 411(6835): p. 349-54.
38. Hebrok, M., Hedgehog signaling in pancreas development. Mech Dev, 2003. 120(1): p. 45-57.
39. Kuenzli, S., Sorg, O., and Saurat, J. H., Cyclopamine, hedgehog and psoriasis. Dermatology, 2004. 209(2): p. 81-3.
40. Tas, S. and Avci, O., Rapid clearance of psoriatic skin lesions induced by topical cyclopamine. A preliminary proof of concept study. Dermatology, 2004. 209(2): p. 126-31.
41. Duman-Scheel, M., Weng, L., Xin, S., and Du, W., Hedgehog regulates cell growth and proliferation by inducing Cyclin D and Cyclin E. Nature, 2002. 417(6886): p. 299-304.
42. Pola, R., Ling, L. E., Silver, M., Corbley, M. J., Kearney, M., Blake Pepinsky, R., Shapiro, R., Taylor, F. R., Baker, D. P., Asahara, T., and Isner, J. M., The morphogen Sonic hedgehog is an indirect angiogenic agent upregulating two families of angiogenic growth factors. Nat Med, 2001. 7(6): p. 706-11.
43. Chen, J. K., Taipale, J., Young, K. E., Maiti, T., and Beachy, P. A., Small molecule modulation of Smoothened activity. Proc Natl Acad Sci USA, 2002. 99(22): p. 14071-6.
44. Frank-Kamenetsky, M., Zhang, X. M., Bottega, S., Guicherit, O., Wichterle, H., Dudek, H., Bumcrot, D., Wang, F. Y., Jones, S., Shulok, J., Rubin, L. L., and Porter, J. A., Small-molecule modulators of Hedgehog signaling: identification and characterization of Smoothened agonists and antagonists. J Biol, 2002. 1(2): p. 10.
45. Bijlsma, M. F., Spek, C. A., and Peppelenbosch, M. P., Hedgehog: an unusual signal transducer. Bioessays, 2004. 26(4): p. 387-94.
46. Gaffield, W., Incardona, J. P., Kapur, R. P., and Roelink, H., A looking glass perspective: thalidomide and cyclopamine. Cell Mol Biol (Noisy-le-grand), 1999. 45(5): p. 579-88.
47. Pasca di Magliano, M. and Hebrok, M., Hedgehog signalling in cancer formation and maintenance. Nat Rev Cancer, 2003. 3(12): p. 903-11.
48. Kim, S. K. and Melton, D. A., Pancreas development is promoted by cyclopamine, a hedgehog signaling inhibitor. Proc Natl Acad Sci USA, 1998. 95(22): p. 13036-41.
49. Incardona, J. P., Gaffield, W., Kapur, R. P., and Roelink, H., The teratogenic Veratrum alkaloid cyclopamine inhibits sonic hedgehog signal transduction. Development, 1998. 125(18): p. 3553-62.
50. Vokes, S. A., Yatskievych, T. A., Heimark, R. L., McMahon, J., McMahon, A. P., Antin, P. B., and Krieg, P. A., Hedgehog signaling is essential for endothelial tube formation during vasculogenesis. Development, 2004. 131(17): p. 4371-80.
51. Olsen, C. L., Hsu, P. P., Glienke, J., Rubanyi, G. M., and Brooks, A. R., Hedgehog-interacting protein is highly expressed in endothelial cells but down-regulated during angiogenesis and in several human tumors. BMC Cancer, 2004. 4(1): p. 43.
52. Kubo, M., Nakamura, M., Tasaki, A., Yamanaka, N., Nakashima, H., Nomura, M., Kuroki, S., and Katano, M., Hedgehog signaling pathway is a new therapeutic target for patients with breast cancer. Cancer Res, 2004. 64(17): p. 6071-4.
53. Chuang, P. T., Kawcak, T., and McMahon, A. P., Feedback control of mammalian Hedgehog signaling by the Hedgehog-binding protein, Hip1, modulates Fgf signaling during branching morphogenesis of the lung. Genes Dev, 2003. 17(3): p. 342-7.
54. Chuang, P. T. and McMahon, A. P., Vertebrate Hedgehog signalling modulated by induction of a Hedgehog-binding protein. Nature, 1999. 397(6720): p. 617-21.
55. Zeng, X., Goetz, J. A., Suber, L. M., Scott, W. J., Jr., Schreiner, C. M., and Robbins, D. J., A freely diffusible form of Sonic hedgehog mediates long-range signalling. Nature, 2001. 411(6838): p. 716-20.
56. Coulombe, J., Traiffort, E., Loulier, K., Faure, H., and Ruat, M., Hedgehog interacting protein in the mature brain: membrane-associated and soluble forms. Mol Cell Neurosci, 2004. 25(2): p. 323-33.
57. Izraeli, S. and Rechavi, G., Molecular medicine—an overview. Isr Med Assoc J, 2002. 4(8): p. 638-40.
58. Mohr, L. and Geissler, M., [Gene therapy: new developments]. Schweiz Rundsch Med Prax, 2002. 91(51-52): p. 2227-35
59. Graham, F. L. and van der Eb, A. J., A new technique for the assay of infectivity of human adenovirus 5 DNA. Virology, 1973. 52(2): p. 456-67.
60. Graham, F. L. and van der Eb, A. J., Transformation of rat cells by DNA of human adenovirus 5. Virology, 1973. 54(2): p. 536-9.
61. Chu, G. and Sharp, P. A., SV40 DNA transfection of cells in suspension: analysis of efficiency of transcription and translation of T-antigen. Gene, 1981. 13(2): p. 197-202.
62. Fire, A., Xu, S., Montgomery, M. K., Kostas, S. A., Driver, S. E., and Mello, C. C., Potent and specific genetic interference by double-stranded RNA in Caenorhabditis elegans. Nature, 1998. 391(6669): p. 806-11.
63. Bosher, J. M. and Labouesse, M., RNA interference: genetic wand and genetic watchdog. Nat Cell Biol, 2000. 2(2): p. E31-6.
64. Sharp, P. A., RNA interference—2001. Genes Dev, 2001. 15(5): p. 485-90.
65. Hammond, S. M., Caudy, A. A., and Hannon, G. J., Post-transcriptional gene silencing by double-stranded RNA. Nat Rev Genet, 2001. 2(2): p. 110-9.
66. Zamore, P. D., RNA interference: listening to the sound of silence. Nat Struct Biol, 2001. 8(9): p. 746-50.

67. Moss, E. G., RNA interference: it's a small RNA world. Curr Biol, 2001. 11(19): p. R772-5.
68. Fjose, A., Ellingsen, S., Wargelius, A., and Seo, H. C., RNA interference: mechanisms and applications. Biotechnol Annu Rev, 2001. 7: p. 31-57.
69. Tuschl, T., RNA interference and small interfering RNAs. Chembiochem, 2001. 2(4): p. 239-45.
70. Cullen, B. R., RNA interference: antiviral defense and genetic tool. Nat Immunol, 2002. 3(7): p. 597-9.
71. Hannon, G. J., RNA interference. Nature, 2002. 418(6894): p. 244-51.
72. Kitabwalla, M. and Ruprecht, R. M., RNA interference—a new weapon against HIV and beyond. N Engl J Med, 2002. 347(17): p. 1364-7.
73. McManus, M. T. and Sharp, P. A., Gene silencing in mammals by small interfering RNAs. Nat Rev Genet, 2002. 3(10): p. 737-47.
74. Elbashir, S. M., Harborth, J., Lendeckel, W., Yalcin, A., Weber, K., and Tuschl, T., Duplexes of 21-nucleotide RNAs mediate RNA interference in cultured mammalian cells. Nature, 2001. 411(6836): p. 494-8.
75. Caplen, N. J., Parrish, S., Imani, F., Fire, A., and Morgan, R. A., Specific inhibition of gene expression by small double-stranded RNAs in invertebrate and vertebrate systems. Proc Natl Acad Sci USA, 2001. 98(17): p. 9742-7.
76. Paddison, P. J., Caudy, A. A., Bernstein, E., Hannon, G. J., and Conklin, D. S., Short hairpin RNAs (shRNAs) induce sequence-specific silencing in mammalian cells. Genes Dev, 2002. 16(8): p. 948-58.
77. Kusser, W., Chemically modified nucleic acid aptamers for in vitro selections: evolving evolution. J Biotechnol, 2000. 74(1): p. 27-38.
78. Sun, S., Technology evaluation: SELEX, Gilead Sciences Inc. Curr Opin Mol Ther, 2000. 2(1): p. 100-5.
79. Brody, E. N. and Gold, L., Aptamers as therapeutic and diagnostic agents. J Biotechnol, 2000. 74(1): p. 5-13.
80. Kramvis, A., Bukofzer, S., and Kew, M. C., Comparison of hepatitis B virus DNA extractions from serum by the QIAamp blood kit, GeneReleaser, and the phenol-chloroform method. J Clin Microbiol, 1996. 34(11): p. 2731-3.
81. Cuenoud, B. and Szostak, J. W., A DNA metalloenzyme with DNA ligase activity. Nature, 1995. 375(6532): p. 611-4.
82. Studier, F. W., Rosenberg, A. H., Dunn, J. J., and Dubendorff, J. W., Use of T7 RNA polymerase to direct expression of cloned genes. Methods Enzymol, 1990. 185: p. 60-89.
83. Benoist, C. and Chambon, P., In vivo sequence requirements of the SV40 early promotor region. Nature, 1981. 290(5804): p. 304-10.
84. Yamamoto, T., de Crombrugghe, B., and Pastan, I., Identification of a functional promoter in the long terminal repeat of Rous sarcoma virus. Cell, 1980. 22(3): p. 787-97.
85. Wagner, E. F., Stewart, T. A., and Mintz, B., The human beta-globin gene and a functional viral thymidine kinase gene in developing mice. Proc Natl Acad Sci USA, 1981. 78(8): p. 5016-20.
86. Brinster, R. L., Chen, H. Y., Warren, R., Sarthy, A., and Palmiter, R. D., Regulation of metallothionein—thymidine kinase fusion plasmids injected into mouse eggs. Nature, 1982. 296(5852): p. 39-42.
87. Herrera-Estrella, L., Van den Broeck, G., Maenhaut, R., Van Montagu, M., Schell, J., Timko, M., and Cashmore, A., Light-inducible and chloroplast-associated expression of a chimaeric gene introduced into Nicotiana tabacum using a Ti plasmid vector. Nature, 1984. 310(5973): p. 115-20.
88. Gardner, R. C., Howarth, A. J., Hahn, P., Brown-Luedi, M., Shepherd, R. J., and Messing, J., The complete nucleotide sequence of an infectious clone of cauliflower mosaic virus by M13mp7 shotgun sequencing. Nucleic Acids Res, 1981. 9(12): p. 2871-88.
89. Swift, G. H., Hammer, R. E., MacDonald, R. J., and Brinster, R. L., Tissue-specific expression of the rat pancreatic elastase I gene in transgenic mice. Cell, 1984. 38(3): p. 639-46.
90. MacDonald, R. J., Hammer, R. E., Swift, G. H., Ornitz, D. M., Davis, B. P., Palmiter, R. D., and Brinster, R. L., Tissue-specific expression of pancreatic genes in transgenic mice. Ann NY Acad Sci, 1986. 478: p. 131-46.
91. Hanahan, D., Heritable formation of pancreatic beta-cell tumours in transgenic mice expressing recombinant insulin/simian virus 40 oncogenes. Nature, 1985. 315(6015): p. 115-22.
92. Grosschedl, R., Weaver, D., Baltimore, D., and Costantini, F., Introduction of a mu immunoglobulin gene into the mouse germ line: specific expression in lymphoid cells and synthesis of functional antibody. Cell, 1984. 38(3): p. 647-58.
93. Adams, J. M., Harris, A. W., Pinkert, C. A., Corcoran, L. M., Alexander, W. S., Cory, S., Palmiter, R. D., and Brinster, R. L., The c-myc oncogene driven by immunoglobulin enhancers induces lymphoid malignancy in transgenic mice. Nature, 1985. 318(6046): p. 533-8.
94. Alexander, W. S., Schrader, J. W., and Adams, J. M., Expression of the c-myc oncogene under control of an immunoglobulin enhancer in E mu-myc transgenic mice. Mol Cell Biol, 1987. 7(4): p. 1436-44.
95. Boshart, M., Weber, F., Jahn, G., Dorsch-Hasler, K., Fleckenstein, B., and Schaffner, W., A very strong enhancer is located upstream of an immediate early gene of human cytomegalovirus. Cell, 1985. 41(2): p. 521-30.
96. Leder, A., Pattengale, P. K., Kuo, A., Stewart, T. A., and Leder, P., Consequences of widespread deregulation of the c-myc gene in transgenic mice: multiple neoplasms and normal development. Cell, 1986. 45(4): p. 485-95.
97. Pinkert, C. A., Ornitz, D. M., Brinster, R. L., and Palmiter, R. D., An albumin enhancer located 10 kb upstream functions along with its promoter to direct efficient, liver-specific expression in transgenic mice. Genes Dev, 1987. 1(3): p. 268-76.
98. Krumlauf, R., Hammer, R. E., Tilghman, S. M., and Brinster, R. L., Developmental regulation of α-fetoprotein genes in transgenic mice. Mol Cell Biol, 1985. 5(7): p. 1639-48.
99. Hammer, R. E., Krumlauf, R., Camper, S. A., Brinster, R. L., and Tilghman, S. M., Diversity of α-fetoprotein gene expression in mice is generated by a combination of separate enhancer elements. Science, 1987. 235(4784): p. 53-8.
100. Kelsey, G. D., Povey, S., Bygrave, A. E., and Lovell-Badge, R. H., Species- and tissue-specific expression of human α1-antitrypsin in transgenic mice. Genes Dev, 1987. 1(2): p. 161-71.
101. Kollias, G., Wrighton, N., Hurst, J., and Grosveld, F., Regulated expression of human A gamma-, beta-, and hybrid gamma beta-globin genes in transgenic mice: manipulation of the developmental expression patterns. Cell, 1986. 46(1): p. 89-94.
102. Readhead, C., Popko, B., Takahashi, N., Shine, H. D., Saavedra, R. A., Sidman, R. L., and Hood, L., Expression of a myelin basic protein gene in transgenic shiverer mice: correction of the dysmyelinating phenotype. Cell, 1987. 48(4): p. 703-12.

103. Shani, M., Tissue-specific expression of rat myosin light-chain 2 gene in transgenic mice. Nature, 1985. 314 (6008): p. 283-6.
104. Mason, A. J., Hayflick, J. S., Zoeller, R. T., Young, W. S., 3rd, Phillips, H. S., Nikolics, K., and Seeburg, P. H., A deletion truncating the gonadotropin-releasing hormone gene is responsible for hypogonadism in the hpg mouse. Science, 1986. 234(4782): p. 1366-71.
105. Boerner, P., Lafond, R., Lu, W. Z., Brams, P., and Royston, I., Production of antigen-specific human monoclonal antibodies from in vitro-primed human splenocytes. J Immunol, 1991. 147(1): p. 86-95.
106. Persson, M. A., Caothien, R. H., and Burton, D. R., Generation of diverse high-affinity human monoclonal antibodies by repertoire cloning. Proc Natl Acad Sci USA, 1991. 88(6): p. 2432-6.
107. Huang, C. and Stollar, B. D., Construction of representative immunoglobulin variable region cDNA libraries from human peripheral blood lymphocytes without in vitro stimulation. J Immunol Methods, 1991. 141(2): p. 227-36.
108. Vaughan, T. J., Osbourn, J. K., and Tempest, P. R., Human antibodies by design. Nat Biotechnol, 1998. 16(6): p. 535-9.
109. Vaughan, T. J., Williams, A. J., Pritchard, K., Osbourn, J. K., Pope, A. R., Earnshaw, J. C., McCafferty, J., Hodits, R. A., Wilton, J., and Johnson, K. S., Human antibodies with sub-nanomolar affinities isolated from a large non-immunized phage display library. Nat Biotechnol, 1996. 14(3): p. 309-14.
110. Vaughan, C. K. and Sollazzo, M., Of minibody, camel and bacteriophage. Comb Chem High Throughput Screen, 2001. 4(5): p. 417-30.
111. Riechmann, L., Foote, J., and Winter, G., Expression of an antibody Fv fragment in myeloma cells. J Mol Biol, 1988. 203(3): p. 825-8.
112. Riechmann, L., Clark, M., Waldmann, H., and Winter, G., Reshaping human antibodies for therapy. Nature, 1988. 332(6162): p. 323-7.
113. Verhoeyen, M. and Riechmann, L., Engineering of antibodies. Bioessays, 1988. 8(2): p. 74-8.
114. van der Krol, A. R., Mol, J. N., and Stuitje, A. R., Modulation of eukaryotic gene expression by complementary RNA or DNA sequences. Biotechniques, 1988. 6(10): p. 958-76.
115. Stein, C. A. and Cohen, J. S., Oligodeoxynucleotides as inhibitors of gene expression: a review. Cancer Res, 1988. 48(10): p. 2659-68.
116. Wagner, R. W., Gene inhibition using antisense oligodeoxynucleotides. Nature, 1994. 372(6504): p. 333-5. 117. Letsinger, R. L., Zhang, G. R., Sun, D. K., Ikeuchi, T., and Sarin, P. S., Cholesteryl-conjugated oligonucleotides: synthesis, properties, and activity as inhibitors of replication of human immunodeficiency virus in cell culture. Proc Natl Acad Sci USA, 1989. 86(17): p. 6553-6.
118. Lemaitre, M., Bayard, B., and Lebleu, B., Specific antiviral activity of a poly(L-lysine)-conjugated oligodeoxyribonucleotide sequence complementary to vesicular stomatitis virus N protein mRNA initiation site. Proc Natl Acad Sci USA, 1987. 84(3): p. 648-52.
119. Zon, G., Oligonucleotide analogues as potential chemotherapeutic agents. Pharm Res, 1988. 5(9): p. 539-49.
120. Perry-O'Keefe, H., Yao, X. W., Coull, J. M., Fuchs, M., and Egholm, M., Peptide nucleic acid pre-gel hybridization: an alternative to southern hybridization. Proc Natl Acad Sci USA, 1996. 93(25): p. 14670-5.
121. Egholm, M., Buchardt, O., Christensen, L., Behrens, C., Freier, S. M., Driver, D. A., Berg, R. H., Kim, S. K., Norden, B., and Nielsen, P. E., PNA hybridizes to complementary oligonucleotides obeying the Watson-Crick hydrogen-bonding rules. Nature, 1993. 365(6446): p. 566-8.
122. Gautier, C., Morvan, F., Rayner, B., Huynh-Dinh, T., Igolen, J., Imbach, J. L., Paoletti, C., and Paoletti, J., Alpha-DNA. IV: Alpha-anomeric and beta-anomeric tetrathymidylates covalently linked to intercalating oxazolopyridocarbazole. Synthesis, physicochemical properties and poly (rA) binding. Nucleic Acids Res, 1987. 15(16): p. 6625-41.
123. Inoue, H., Hayase, Y., Imura, A., Iwai, S., Miura, K., and Ohtsuka, E., Synthesis and hybridization studies on two complementary nona(2'-O-methyl)ribonucleotides. Nucleic Acids Res, 1987. 15(15): p. 6131-48.
124. Loke, S. L., Stein, C., Zhang, X., Avigan, M., Cohen, J., and Neckers, L. M., Delivery of c-myc antisense phosphorothioate oligodeoxynucleotides to hematopoietic cells in culture by liposome fusion: specific reduction in c-myc protein expression correlates with inhibition of cell growth and DNA synthesis. Curr Top Microbiol Immunol, 1988. 141: p. 282-9.
125. Stein, C. A., Mori, K., Loke, S. L., Subasinghe, C., Shinozuka, K., Cohen, J. S., and Neckers, L. M., Phosphorothioate and normal oligodeoxyribonucleotides with 5'-linked acridine: characterization and preliminary kinetics of cellular uptake. Gene, 1988. 72(1-2): p. 333-41.
126. Stein, C. A., Subasinghe, C., Shinozuka, K., and Cohen, J. S., Physicochemical properties of phosphorothioate oligodeoxynucleotides. Nucleic Acids Res, 1988. 16(8): p. 3209-21.
127. Matsukura, M., Zon, G., Shinozuka, K., Stein, C. A., Mitsuya, H., Cohen, J. S., and Broder, S., Synthesis of phosphorothioate analogues of oligodeoxyribonucleotides and their antiviral activity against human immunodeficiency virus (HIV). Gene, 1988. 72(1-2): p. 343-7.
128. Sarin, P. S., Agrawal, S., Civeira, M. P., Goodchild, J., Ikeuchi, T., and Zamecnik, P. C., Inhibition of acquired immunodeficiency syndrome virus by oligodeoxynucleoside methylphosphonates. Proc Natl Acad Sci USA, 1988. 85(20): p. 7448-51.
129. Sarver, N., Cantin, E. M., Chang, P. S., Zaia, J. A., Ladne, P. A., Stephens, D. A., and Rossi, J. J., Ribozymes as potential anti-HIV-1 therapeutic agents. Science, 1990. 247(4947): p. 1222-5.
130. Haseloff, J. and Gerlach, W. L., Simple RNA enzymes with new and highly specific endoribonuclease activities. Nature, 1988. 334(6183): p. 585-91.
131. Zaug, A. J. and Cech, T. R., The intervening sequence RNA of Tetrahymena is an enzyme. Science, 1986. 231 (4737): p. 470-5.
132. Zaug, A. J., Kent, J. R., and Cech, T. R., Reactions of the intervening sequence of the Tetrahymena ribosomal ribonucleic acid precursor: pH dependence of cyclization and site-specific hydrolysis. Biochemistry, 1985. 24(22): p. 6211-8.
133. Zaug, A. J., Grabowski, P. J., and Cech, T. R., Autocatalytic cyclization of an excised intervening sequence RNA is a cleavage-ligation reaction. Nature, 1983. 301(5901): p. 578-83.
134. Cech, T. R., Zaug, A. J., and Grabowski, P. J., In vitro splicing of the ribosomal RNA precursor of Tetrahymena: involvement of a guanosine nucleotide in the excision of the intervening sequence. Cell, 1981. 27(3 Pt 2): p. 487-96.
135. Zaug, A. J. and Cech, T. R., The intervening sequence excised from the ribosomal RNA precursor of Tetrahymena contains a 5-terminal guanosine residue not encoded by the DNA. Nucleic Acids Res, 1982. 10(9): p. 2823-38.
136. Been, M. D. and Cech, T. R., One binding site determines sequence specificity of Tetrahymena pre-rRNA self-splicing, trans-splicing, and RNA enzyme activity. Cell, 1986 47 (2): p. 207-16.
137. Helene, C., The anti-gene strategy: control of gene expression by triplex-forming-oligonucleotides. Anticancer Drug Des, 1991. 6(6): p. 569-84.
138. Maher, L. J., 3rd, DNA triple-helix formation: an approach to artificial gene repressors? Bioessays, 1992. 14(12): p. 807-15.
139. Heidenreich, O., Gryaznov, S., and Nerenberg, M., RNase H-independent antisense activity of oligonucleotide N3'→P5' phosphoramidates. Nucleic Acids Res, 1997. 25(4): p. 776-80.
140. Wilson, W. D., Mizan, S., Tanious, F. A., Yao, S., and Zon, G., The interaction of intercalators and groove-binding agents with DNA triple-helical structures: the influence of ligand structure, DNA backbone modifications and sequence. J Mol Recognit, 1994. 7(2): p. 89-98.
141. Chen, J. K., Schultz, R. G., Lloyd, D. H., and Gryaznov, S. M., Synthesis of oligodeoxyribonucleotide N3'→P5' phosphoramidates. Nucleic Acids Res, 1995. 23(14): p. 2661-8.
142. Elbashir, S. M., Martinez, J., Patkaniowska, A., Lendeckel, W., and Tuschl, T., Functional anatomy of siRNAs for mediating efficient RNAi in Drosophila melanogaster embryo lysate. Embo J, 2001. 20(23): p. 6877-88.
143. McCaffrey, A. P., Meuse, L., Pham, T. T., Conklin, D. S., Hannon, G. J., and Kay, M. A., RNA interference in adult mice. Nature, 2002. 418(6893): p. 38-9.
144. McManus, M. T., Petersen, C. P., Haines, B. B., Chen, J., and Sharp, P. A., Gene silencing using micro-RNA designed hairpins. Rna, 2002. 8(6): p. 842-50.
145. Yu, J. Y., DeRuiter, S. L., and Turner, D. L., RNA interference by expression of short-interfering RNAs and hairpin RNAs in mammalian cells. Proc Natl Acad Sci USA, 2002. 99(9): p. 6047-52.
146. Gold, L., Brown, D., He, Y., Shtatland, T., Singer, B. S., and Wu, Y., From oligonucleotide shapes to genomic SELEX: novel biological regulatory loops. Proc Natl Acad Sci USA, 1997. 94(1): p. 59-64.
147. Gold, L., The SELEX process: a surprising source of therapeutic and diagnostic compounds. Harvey Lect, 1995. 91: p. 47-57.
148. Klug, S. J. and Famulok, M., All you wanted to know about SELEX. Mol Biol Rep, 1994. 20(2): p. 97-107.
149. Berge, S. M., Bighley, L. D., and Monkhouse, D. C., Pharmaceutical salts. J Pharm Sci, 1977. 66(1): p. 1-19.

What is claimed is:

1. A method inhibiting and/or reversing a disease related with ocular neovascularization in a mammalian subject comprising administering to the subject a therapeutically effective amount of a soluble Hedgehog interacting protein 1 (Hip1) consisting of the amino acids of SEQ ID NO:6 obtained from Hip1 by deletion of the transmembrane segment located at the C-terminus, and optionally containing a signal peptide.

2. The method according to claim 1, wherein the disease is selected from the group consisting of age-related macular degeneration, diabetic retinopathy, retinopathy of prematurity (ROP), neovascular glaucoma, and retinal vein occlusion.

3. A method of inhibiting and/or reversing ocular neovascularization diseases in a mammalian subject comprising administering to the subject a therapeutically effective amount of soluble Hedgehog interacting protein 1 (Hip1) consisting of the amino acids of SEQ ID NO:6 wherein said soluble Hip1 binds to and sequesters Hedgehog protein to interfere with Hedgehog signaling.

4. The method according to claim 3, wherein the disease is selected from the group consisting of age-related macular degeneration, diabetic retinopathy, retinopathy of prematurity (ROP), neovascular glaucoma, and retinal vein occlusion.

5. The method according to claim 3, wherein the disease is selected from the group consisting of age-related macular degeneration, diabetic retinopathy, and retinal vein occlusion.

6. The method according to claim 4, wherein the disease is an age-related macular degeneration.

7. The method according to claim 3, wherein the disease is diabetic retinopathy.

8. The method according to claim 4, wherein the disease is retinopathy of prematurity (ROP).

9. The method according to claim 3, wherein the disease is neovascular glaucoma.

10. The method according to claim 3, wherein the disease is retinal vein occlusion.

11. The method according to claim 1, wherein said soluble Hip1 has a signal peptide.

12. The method according to claim 3, wherein said soluble Hip1 has a signal peptide.

\* \* \* \* \*

SEQUENCE LISTING

<160> NUMBER OF SEQ ID NOS: 20

<210> SEQ ID NO 1
<211> LENGTH: 2103
<212> TYPE: DNA
<213> ORGANISM: Mus musculus
<220> FEATURE:
<221> NAME/KEY: CDS
<222> LOCATION: (1)..(2103)
<223> OTHER INFORMATION: Hip1 cDNA (murine)

<400> SEQUENCE: 1

```
atg ctg aag atg ctc tcg ttt aag ctg cta ctg ctg gcc gtg gct ctg      48
Met Leu Lys Met Leu Ser Phe Lys Leu Leu Leu Leu Ala Val Ala Leu
1               5                   10                  15 ggc ttc ttt gaa gga gat gcg aag ttt ggg gaa agg aac gag ggg agc      96
Gly Phe Phe Glu Gly Asp Ala Lys Phe Gly Glu Arg Asn Glu Gly Ser
                20                  25                  30 gga gcg aga agg aga cgg tgc ctg aat ggg aac cca aag cgc cta         144
Gly Ala Arg Arg Arg Arg Cys Leu Asn Gly Asn Pro Lys Arg Leu
            35                  40                  45 aag aga agg gac agg cgg gtg atg tcc cag ctg gag ctc agt gga         192
Lys Arg Arg Asp Arg Arg Val Met Ser Gln Leu Glu Leu Leu Ser Gly
        50                  55                  60 gga gag atc ctg tgt ggt ggc ttc tac cca cga gta tct tgc tgc ctg     240
Gly Glu Ile Leu Cys Gly Gly Phe Tyr Pro Arg Val Ser Cys Cys Leu
65                  70                  75                  80 cag agt gac agc cct gga ttg ggg cgt ctg gag aac aag atc ttt tct     288
Gln Ser Asp Ser Pro Gly Leu Gly Arg Leu Glu Asn Lys Ile Phe Ser
                85                  90                  95 gcc acc aac aac tca gaa tgc agc agg ctg ctg gag gag atc caa tgt     336
Ala Thr Asn Asn Ser Glu Cys Ser Arg Leu Leu Glu Glu Ile Gln Cys
                100                 105                 110 gct ccc tgc tcc ccg cat tcc cag agc ctc ttc tac aca cct gaa aga     384
Ala Pro Cys Ser Pro His Ser Gln Ser Leu Phe Tyr Thr Pro Glu Arg
            115                 120                 125
```

```
gat gtc ctg gat ggg gac cta gca ctt cca ctc ctc tgc aaa gac tac       432
Asp Val Leu Asp Gly Asp Leu Ala Leu Pro Leu Leu Cys Lys Asp Tyr
    130                 135                 140 tgc aaa gaa ttc ttt tat act tgc cga ggc cat att cca ggt ctt ctt       480
Cys Lys Glu Phe Phe Tyr Thr Cys Arg Gly His Ile Pro Gly Leu Leu
145                 150                 155                 160 caa aca act gct gat gaa ttt tgc ttt tac tat gca aga aaa gat gct       528
Gln Thr Thr Ala Asp Glu Phe Cys Phe Tyr Tyr Ala Arg Lys Asp Ala
                165                 170                 175 ggg tta tgc ttt cca gac ttc ccg aga aag caa gtc aga gga cca gca       576
Gly Leu Cys Phe Pro Asp Phe Pro Arg Lys Gln Val Arg Gly Pro Ala
            180                 185                 190 tct aac tac ttg ggc cag atg gaa gac tac gag aaa gtg ggg ggg atc       624
Ser Asn Tyr Leu Gly Gln Met Glu Asp Tyr Glu Lys Val Gly Gly Ile
        195                 200                 205 agc aga aaa cac aaa cac aac tgc ctc tgt gtc cag gag gtc atg agt       672
Ser Arg Lys His Lys His Asn Cys Leu Cys Val Gln Glu Val Met Ser
    210                 215                 220 ggg ctg cgg cag cct gtg agc gct gtg cac agc ggg gat ggc tcc cat       720
Gly Leu Arg Gln Pro Val Ser Ala Val His Ser Gly Asp Gly Ser His
225                 230                 235                 240 cgg ctc ttc att cta gag aag gaa ggc tac gtg aag att cta acc cca       768
Arg Leu Phe Ile Leu Glu Lys Glu Gly Tyr Val Lys Ile Leu Thr Pro
                245                 250                 255 gaa gga gaa ctg ttc aag gag cct tac ttg gac att cac aaa ctt gtt       816
Glu Gly Glu Leu Phe Lys Glu Pro Tyr Leu Asp Ile His Lys Leu Val
            260                 265                 270 caa agt gga ata aag gga gga gac gaa agg ggc ctg cta agc ctg gca       864
Gln Ser Gly Ile Lys Gly Gly Asp Glu Arg Gly Leu Leu Ser Leu Ala
        275                 280                 285 ttc cat ccc aat tac aag aaa aat gga aag ctg tat gtg tct tat acc       912
Phe His Pro Asn Tyr Lys Lys Asn Gly Lys Leu Tyr Val Ser Tyr Thr
    290                 295                 300 acc aac cag gaa cgg tgg gct att ggg cct cac gac cac att ctt cgg       960
Thr Asn Gln Glu Arg Trp Ala Ile Gly Pro His Asp His Ile Leu Arg
305                 310                 315                 320 gtt gtg gaa tac aca gta tcc agg aaa aac ccc cat caa gtt gat gtg      1008
Val Val Glu Tyr Thr Val Ser Arg Lys Asn Pro His Gln Val Asp Val
                325                 330                 335 aga aca gcc agg gtg ttt ctg gaa gtc gca gag ctc cac cga aag cat      1056
Arg Thr Ala Arg Val Phe Leu Glu Val Ala Glu Leu His Arg Lys His
            340                 345                 350 ctt ggg gga cag ctg ctc ttt ggt cct gat ggc ttt ttg tac atc atc      1104
Leu Gly Gly Gln Leu Leu Phe Gly Pro Asp Gly Phe Leu Tyr Ile Ile
        355                 360                 365 ctt ggg gat ggt atg atc aca ttg gat gac atg gaa gag atg gat ggg      1152
Leu Gly Asp Gly Met Ile Thr Leu Asp Asp Met Glu Glu Met Asp Gly
    370                 375                 380 tta agt gac ttc aca ggc tct gtg ctg agg ctg gac gtg gac acc gac      1200
Leu Ser Asp Phe Thr Gly Ser Val Leu Arg Leu Asp Val Asp Thr Asp
385                 390                 395                 400 atg tgc aat gtg cct tat tcc ata cct cgg agt aac cct cac ttc aac      1248
Met Cys Asn Val Pro Tyr Ser Ile Pro Arg Ser Asn Pro His Phe Asn
                405                 410                 415 agc acc aac cag ccc cca gaa gta ttt gcc cac ggc ctc cat gat cca      1296
Ser Thr Asn Gln Pro Pro Glu Val Phe Ala His Gly Leu His Asp Pro
            420                 425                 430 ggc aga tgt gcc gtg gat cga cat cct act gat ata aac atc aat tta      1344
Gly Arg Cys Ala Val Asp Arg His Pro Thr Asp Ile Asn Ile Asn Leu
```

```
                435                 440                 445
aca ata ctt tgc tca gat tcc aac ggg aaa aac agg tca tca gcc aga    1392
Thr Ile Leu Cys Ser Asp Ser Asn Gly Lys Asn Arg Ser Ser Ala Arg
    450                 455                 460 atc cta cag ata ata aag gga aga ggt tat gaa agt gag cca tct ctt    1440
Ile Leu Gln Ile Ile Lys Gly Arg Gly Tyr Glu Ser Glu Pro Ser Leu
465                 470                 475                 480 ctt gaa ttc aag cca ttc agt aac ggc cct ttg gtt ggt gga ttt gtt    1488
Leu Glu Phe Lys Pro Phe Ser Asn Gly Pro Leu Val Gly Gly Phe Val
                485                 490                 495 tac aga ggc tgt cag tct gaa aga ttg tac gga agc tat gtg ttc gga    1536
Tyr Arg Gly Cys Gln Ser Glu Arg Leu Tyr Gly Ser Tyr Val Phe Gly
            500                 505                 510 gat cgc aat ggg aat ttc tta acc ctc cag caa agc cca gtg acc aag    1584
Asp Arg Asn Gly Asn Phe Leu Thr Leu Gln Gln Ser Pro Val Thr Lys
        515                 520                 525 caa tgg caa gaa aag ccg ctc tgc ctg ggt gcc agc agc tcc tgt cga    1632
Gln Trp Gln Glu Lys Pro Leu Cys Leu Gly Ala Ser Ser Ser Cys Arg
    530                 535                 540 ggc tac ttt tcg ggt cac atc ttg gga ttt gga gaa gat gaa tta gga    1680
Gly Tyr Phe Ser Gly His Ile Leu Gly Phe Gly Glu Asp Glu Leu Gly
545                 550                 555                 560 gag gtt tac att cta tca agc agt aag agt atg acc cag act cac aat    1728
Glu Val Tyr Ile Leu Ser Ser Ser Lys Ser Met Thr Gln Thr His Asn
                565                 570                 575 gga aaa ctc tac aag atc gta gac ccc aaa aga cct tta atg cct gag    1776
Gly Lys Leu Tyr Lys Ile Val Asp Pro Lys Arg Pro Leu Met Pro Glu
            580                 585                 590 gaa tgc aga gtc aca gtt caa cct gcc cag cca ctg acc tcc gat tgc    1824
Glu Cys Arg Val Thr Val Gln Pro Ala Gln Pro Leu Thr Ser Asp Cys
        595                 600                 605 tcc cgg ctc tgt cga aac ggc tac tac acc ccc act ggc aag tgc tgc    1872
Ser Arg Leu Cys Arg Asn Gly Tyr Tyr Thr Pro Thr Gly Lys Cys Cys
    610                 615                 620 tgc agt ccc ggc tgg gag gga gac ttc tgc aga att gcc aag tgt gag    1920
Cys Ser Pro Gly Trp Glu Gly Asp Phe Cys Arg Ile Ala Lys Cys Glu
625                 630                 635                 640 cca gcg tgc cgt cat gga ggt gtc tgt gtc aga ccg aac aag tgc ctc    1968
Pro Ala Cys Arg His Gly Gly Val Cys Val Arg Pro Asn Lys Cys Leu
                645                 650                 655 tgt aaa aag ggc tat ctt ggt cct caa tgt gaa caa gtg gac agg aac    2016
Cys Lys Lys Gly Tyr Leu Gly Pro Gln Cys Glu Gln Val Asp Arg Asn
            660                 665                 670 gtc cgc aga gtg acc agg gca ggt atc ctt gat cag atc att gac atg    2064
Val Arg Arg Val Thr Arg Ala Gly Ile Leu Asp Gln Ile Ile Asp Met
        675                 680                 685 acg tct tac ttg ctg gat ctc aca agt tac att gta tag                2103
Thr Ser Tyr Leu Leu Asp Leu Thr Ser Tyr Ile Val
    690                 695                 700

<210> SEQ ID NO 2
<211> LENGTH: 700
<212> TYPE: PRT
<213> ORGANISM: Mus musculus

<400> SEQUENCE: 2

Met Leu Lys Met Leu Ser Phe Lys Leu Leu Leu Ala Val Ala Leu
1               5                   10                  15

Gly Phe Phe Glu Gly Asp Ala Lys Phe Gly Glu Arg Asn Glu Gly Ser
            20                  25                  30
```

-continued

```
Gly Ala Arg Arg Arg Cys Leu Asn Gly Asn Pro Pro Lys Arg Leu
         35                  40                  45
Lys Arg Arg Asp Arg Val Met Ser Gln Leu Glu Leu Leu Ser Gly
 50                  55                  60
Gly Glu Ile Leu Cys Gly Gly Phe Tyr Pro Arg Val Ser Cys Cys Leu
 65                  70                  75                  80
Gln Ser Asp Ser Pro Gly Leu Gly Arg Leu Glu Asn Lys Ile Phe Ser
                 85                  90                  95
Ala Thr Asn Asn Ser Glu Cys Ser Arg Leu Leu Glu Glu Ile Gln Cys
            100                 105                 110
Ala Pro Cys Ser Pro His Ser Gln Ser Leu Phe Tyr Thr Pro Glu Arg
            115                 120                 125
Asp Val Leu Asp Gly Asp Leu Ala Leu Pro Leu Leu Cys Lys Asp Tyr
            130                 135                 140
Cys Lys Glu Phe Phe Tyr Thr Cys Arg Gly His Ile Pro Gly Leu Leu
145                 150                 155                 160
Gln Thr Thr Ala Asp Glu Phe Cys Phe Tyr Tyr Ala Arg Lys Asp Ala
                165                 170                 175
Gly Leu Cys Phe Pro Asp Phe Pro Arg Lys Gln Val Arg Gly Pro Ala
                180                 185                 190
Ser Asn Tyr Leu Gly Gln Met Glu Asp Tyr Glu Lys Val Gly Gly Ile
            195                 200                 205
Ser Arg Lys His Lys His Asn Cys Leu Cys Val Gln Glu Val Met Ser
210                 215                 220
Gly Leu Arg Gln Pro Val Ser Ala Val His Ser Gly Asp Gly Ser His
225                 230                 235                 240
Arg Leu Phe Ile Leu Glu Lys Glu Gly Tyr Val Lys Ile Leu Thr Pro
                245                 250                 255
Glu Gly Glu Leu Phe Lys Glu Pro Tyr Leu Asp Ile His Lys Leu Val
                260                 265                 270
Gln Ser Gly Ile Lys Gly Gly Asp Glu Arg Gly Leu Leu Ser Leu Ala
            275                 280                 285
Phe His Pro Asn Tyr Lys Lys Asn Gly Lys Leu Tyr Val Ser Tyr Thr
290                 295                 300
Thr Asn Gln Glu Arg Trp Ala Ile Gly Pro His Asp His Ile Leu Arg
305                 310                 315                 320
Val Val Glu Tyr Thr Val Ser Arg Lys Asn Pro His Gln Val Asp Val
                325                 330                 335
Arg Thr Ala Arg Val Phe Leu Glu Val Ala Glu Leu His Arg Lys His
            340                 345                 350
Leu Gly Gly Gln Leu Leu Phe Gly Pro Asp Gly Phe Leu Tyr Ile Ile
            355                 360                 365
Leu Gly Asp Gly Met Ile Thr Leu Asp Met Glu Glu Met Asp Gly
            370                 375                 380
Leu Ser Asp Phe Thr Gly Ser Val Leu Arg Leu Asp Val Asp Thr Asp
385                 390                 395                 400
Met Cys Asn Val Pro Tyr Ser Ile Pro Arg Ser Asn Pro His Phe Asn
                405                 410                 415
Ser Thr Asn Gln Pro Pro Glu Val Phe Ala His Gly Leu His Asp Pro
            420                 425                 430
Gly Arg Cys Ala Val Asp Arg His Pro Thr Asp Ile Asn Ile Asn Leu
            435                 440                 445
```

```
Thr Ile Leu Cys Ser Asp Ser Asn Gly Lys Asn Arg Ser Ala Arg
    450                 455                 460

Ile Leu Gln Ile Ile Lys Gly Arg Gly Tyr Glu Ser Glu Pro Ser Leu
465                 470                 475                 480

Leu Glu Phe Lys Pro Phe Ser Asn Gly Pro Leu Val Gly Gly Phe Val
                485                 490                 495

Tyr Arg Gly Cys Gln Ser Glu Arg Leu Tyr Gly Ser Tyr Val Phe Gly
            500                 505                 510

Asp Arg Asn Gly Asn Phe Leu Thr Leu Gln Gln Ser Pro Val Thr Lys
            515                 520                 525

Gln Trp Gln Glu Lys Pro Leu Cys Leu Gly Ala Ser Ser Ser Cys Arg
530                 535                 540

Gly Tyr Phe Ser Gly His Ile Leu Gly Phe Gly Glu Asp Glu Leu Gly
545                 550                 555                 560

Glu Val Tyr Ile Leu Ser Ser Lys Ser Met Thr Gln Thr His Asn
                565                 570                 575

Gly Lys Leu Tyr Lys Ile Val Asp Pro Lys Arg Pro Leu Met Pro Glu
                580                 585                 590

Glu Cys Arg Val Thr Val Gln Pro Ala Gln Pro Leu Thr Ser Asp Cys
            595                 600                 605

Ser Arg Leu Cys Arg Asn Gly Tyr Tyr Thr Pro Thr Gly Lys Cys Cys
            610                 615                 620

Cys Ser Pro Gly Trp Glu Gly Asp Phe Cys Arg Ile Ala Lys Cys Glu
625                 630                 635                 640

Pro Ala Cys Arg His Gly Gly Val Cys Val Arg Pro Asn Lys Cys Leu
                645                 650                 655

Cys Lys Lys Gly Tyr Leu Gly Pro Gln Cys Glu Gln Val Asp Arg Asn
                660                 665                 670

Val Arg Arg Val Thr Arg Ala Gly Ile Leu Asp Gln Ile Ile Asp Met
            675                 680                 685

Thr Ser Tyr Leu Leu Asp Leu Thr Ser Tyr Ile Val
            690                 695                 700

<210> SEQ ID NO 3
<211> LENGTH: 2103
<212> TYPE: DNA
<213> ORGANISM: Homo sapiens
<220> FEATURE:
<221> NAME/KEY: CDS
<222> LOCATION: (1)..(2103)
<223> OTHER INFORMATION: Hip1 cDNA (human)

<400> SEQUENCE: 3 atg ctg aag atg ctc tcc ttt aag ctg ctg ctg gcc gtg gct ctg        48
Met Leu Lys Met Leu Ser Phe Lys Leu Leu Leu Leu Ala Val Ala Leu
1               5                   10                  15 ggc ttc ttt gaa gga gat gct aag ttt ggg gaa aga aac gaa ggg agc   96
Gly Phe Phe Glu Gly Asp Ala Lys Phe Gly Glu Arg Asn Glu Gly Ser
                20                  25                  30 gga gca agg agg aga agg tgc ctg aat ggg aac ccc ccg aag cgc ctg   144
Gly Ala Arg Arg Arg Arg Cys Leu Asn Gly Asn Pro Pro Lys Arg Leu
            35                  40                  45 aaa agg aga gac agg agg atg atg tcc cag ctg gag ctg ctg agt ggg   192
Lys Arg Arg Asp Arg Arg Met Met Ser Gln Leu Glu Leu Leu Ser Gly
        50                  55                  60 gga gag atg ctg tgc ggt ggc ttc tac cct cgg ctg tcc tgc tgc ctg   240
Gly Glu Met Leu Cys Gly Gly Phe Tyr Pro Arg Leu Ser Cys Cys Leu
65                  70                  75                  80
```

```
cgg agt gac agc ccg ggg cta ggg cgc ctg gag aat aag ata ttt tct      288
Arg Ser Asp Ser Pro Gly Leu Gly Arg Leu Glu Asn Lys Ile Phe Ser
             85                  90                  95 gtt acc aac aac aca gaa tgt ggg aag tta ctg gag gaa atc aaa tgt      336
Val Thr Asn Asn Thr Glu Cys Gly Lys Leu Leu Glu Glu Ile Lys Cys
            100                 105                 110 gca ctt tgc tct cca cat tct caa agc ctg ttc cac tca cct gag aga      384
Ala Leu Cys Ser Pro His Ser Gln Ser Leu Phe His Ser Pro Glu Arg
            115                 120                 125 gaa gtc ttg gaa aga gac cta gta ctt cct ctg ctc tgc aaa gac tat      432
Glu Val Leu Glu Arg Asp Leu Val Leu Pro Leu Leu Cys Lys Asp Tyr
130                 135                 140 tgc aaa gaa ttc ttt tac act tgc cga ggc cat att cca ggt ttc ctt      480
Cys Lys Glu Phe Phe Tyr Thr Cys Arg Gly His Ile Pro Gly Phe Leu
145                 150                 155                 160 caa aca act gcg gat gag ttt tgc ttt tac tat gca aga aaa gat ggt      528
Gln Thr Thr Ala Asp Glu Phe Cys Phe Tyr Tyr Ala Arg Lys Asp Gly
            165                 170                 175 ggg ttg tgc ttt cca gat ttt cca aga aaa caa gtc aga gga cca gca      576
Gly Leu Cys Phe Pro Asp Phe Pro Arg Lys Gln Val Arg Gly Pro Ala
            180                 185                 190 tct aac tac ttg gac cag atg gaa gaa tat gac aaa gtg gaa gag atc      624
Ser Asn Tyr Leu Asp Gln Met Glu Glu Tyr Asp Lys Val Glu Glu Ile
            195                 200                 205 agc aga aag cac aaa cac aac tgc ttc tgt att cag gag gtt gtg agt      672
Ser Arg Lys His Lys His Asn Cys Phe Cys Ile Gln Glu Val Val Ser
210                 215                 220 ggg ctg cgg cag ccc gtt ggt gcc ctg cat agt ggg gat ggc tcg caa      720
Gly Leu Arg Gln Pro Val Gly Ala Leu His Ser Gly Asp Gly Ser Gln
225                 230                 235                 240 cgt ctc ttc att ctg gaa aaa gaa ggt tat gtg aag ata ctt acc cct      768
Arg Leu Phe Ile Leu Glu Lys Glu Gly Tyr Val Lys Ile Leu Thr Pro
            245                 250                 255 gaa gga gaa att ttc aag gag cct tat ttg gac att cac aaa ctt gtt      816
Glu Gly Glu Ile Phe Lys Glu Pro Tyr Leu Asp Ile His Lys Leu Val
            260                 265                 270 caa agt gga ata aag gga gga gat gaa aga gga ctg cta agc ctc gca      864
Gln Ser Gly Ile Lys Gly Gly Asp Glu Arg Gly Leu Leu Ser Leu Ala
            275                 280                 285 ttc cat ccc aat tac aag aaa aat gga aag ttg tat gtg tcc tat acc      912
Phe His Pro Asn Tyr Lys Lys Asn Gly Lys Leu Tyr Val Ser Tyr Thr
            290                 295                 300 acc aac caa gaa cgg tgg gct atc ggg cct cat gac cac att ctt agg      960
Thr Asn Gln Glu Arg Trp Ala Ile Gly Pro His Asp His Ile Leu Arg
305                 310                 315                 320 gtt gtg gaa tac aca gta tcc aga aaa aat cca cac caa gtt gat ttg     1008
Val Val Glu Tyr Thr Val Ser Arg Lys Asn Pro His Gln Val Asp Leu
            325                 330                 335 aga aca gcc aga gtc ttt ctt gaa gtt gca gaa ctc cac aga aag cat     1056
Arg Thr Ala Arg Val Phe Leu Glu Val Ala Glu Leu His Arg Lys His
            340                 345                 350 ctg gga gga caa ctg ctc ttt ggc cct gac ggc ttt ttg tac atc att     1104
Leu Gly Gly Gln Leu Leu Phe Gly Pro Asp Gly Phe Leu Tyr Ile Ile
            355                 360                 365 ctt ggt gat ggg atg att aca ctg gat gat atg gaa gaa atg gat ggg     1152
Leu Gly Asp Gly Met Ile Thr Leu Asp Asp Met Glu Glu Met Asp Gly
370                 375                 380 tta agt gat ttc aca ggc tca gtg cta cgg ctg gat gtg gac aca gac     1200
Leu Ser Asp Phe Thr Gly Ser Val Leu Arg Leu Asp Val Asp Thr Asp
```

```
                385                390                395                400
atg tgc aac gtg cct tat tcc ata cca agg agc aac cca cac ttc aac        1248
Met Cys Asn Val Pro Tyr Ser Ile Pro Arg Ser Asn Pro His Phe Asn
                    405                410                415 agc acc aac cag ccc ccc gaa gtg ttt gct cat ggg ctc cac gat cca        1296
Ser Thr Asn Gln Pro Pro Glu Val Phe Ala His Gly Leu His Asp Pro
            420                425                430 ggc aga tgt gct gtg gat aga cat ccc act gat ata aac atc aat tta        1344
Gly Arg Cys Ala Val Asp Arg His Pro Thr Asp Ile Asn Ile Asn Leu
        435                440                445 acg ata ctg tgt tca gac tcc aat gga aaa aac aga tca tca gcc aga        1392
Thr Ile Leu Cys Ser Asp Ser Asn Gly Lys Asn Arg Ser Ser Ala Arg
    450                455                460 att cta cag ata ata aag ggg aaa gat tat gaa agt gag cca tca ctt        1440
Ile Leu Gln Ile Ile Lys Gly Lys Asp Tyr Glu Ser Glu Pro Ser Leu
465                470                475                480 tta gaa ttc aag cca ttc agt aat ggt cct ttg gtt ggt gga ttt gta        1488
Leu Glu Phe Lys Pro Phe Ser Asn Gly Pro Leu Val Gly Gly Phe Val
                485                490                495 tac cgg ggc tgc cag tca gaa aga ttg tat gga agc tac gtg ttt gga        1536
Tyr Arg Gly Cys Gln Ser Glu Arg Leu Tyr Gly Ser Tyr Val Phe Gly
            500                505                510 gat cgt aat ggg aat ttc cta act ctc cag caa agt cct gtg aca aag        1584
Asp Arg Asn Gly Asn Phe Leu Thr Leu Gln Gln Ser Pro Val Thr Lys
        515                520                525 cag tgg caa gaa aaa cca ctc tgt ctc ggc act agt ggg tcc tgt aga        1632
Gln Trp Gln Glu Lys Pro Leu Cys Leu Gly Thr Ser Gly Ser Cys Arg
    530                535                540 ggc tac ttt tcc ggt cac atc ttg gga ttt gga gaa gat gaa cta ggt        1680
Gly Tyr Phe Ser Gly His Ile Leu Gly Phe Gly Glu Asp Glu Leu Gly
545                550                555                560 gaa gtt tac att tta tca agc agt aaa agt atg acc cag act cac aat        1728
Glu Val Tyr Ile Leu Ser Ser Ser Lys Ser Met Thr Gln Thr His Asn
                565                570                575 gga aaa ctc tac aaa att gta gat ccc aaa aga cct tta atg cct gag        1776
Gly Lys Leu Tyr Lys Ile Val Asp Pro Lys Arg Pro Leu Met Pro Glu
            580                585                590 gaa tgc aga gcc acg gta caa cct gca cag aca ctg act tca gag tgc        1824
Glu Cys Arg Ala Thr Val Gln Pro Ala Gln Thr Leu Thr Ser Glu Cys
        595                600                605 tcc agg ctc tgt cga aac ggc tac tgc acc ccc acg gga aag tgc tgc        1872
Ser Arg Leu Cys Arg Asn Gly Tyr Cys Thr Pro Thr Gly Lys Cys Cys
    610                615                620 tgc agt cca ggc tgg gag ggg gac ttc tgc aga act gca aaa tgt gag        1920
Cys Ser Pro Gly Trp Glu Gly Asp Phe Cys Arg Thr Ala Lys Cys Glu
625                630                635                640 cca gca tgt cgt cat gga ggt gtc tgt gtt aga ccg aac aag tgc ctc        1968
Pro Ala Cys Arg His Gly Gly Val Cys Val Arg Pro Asn Lys Cys Leu
                645                650                655 tgt aaa aaa gga tat ctt ggt cct caa tgt gaa caa gtg gac aga aac        2016
Cys Lys Lys Gly Tyr Leu Gly Pro Gln Cys Glu Gln Val Asp Arg Asn
            660                665                670 atc cgc aga gtg acc agg gca ggt att ctt gat cag atc att gac atg        2064
Ile Arg Arg Val Thr Arg Ala Gly Ile Leu Asp Gln Ile Ile Asp Met
        675                680                685 aca tct tac ttg ctg gat cta aca agt tac att gta tag                     2103
Thr Ser Tyr Leu Leu Asp Leu Thr Ser Tyr Ile Val
    690                695                700
```

<210> SEQ ID NO 4
<211> LENGTH: 700
<212> TYPE: PRT
<213> ORGANISM: Homo sapiens

<400> SEQUENCE: 4

Met Leu Lys Met Leu Ser Phe Lys Leu Leu Leu Ala Val Ala Leu
1               5                   10                  15

Gly Phe Phe Glu Gly Asp Ala Lys Phe Gly Glu Arg Asn Glu Gly Ser
                20                  25                  30

Gly Ala Arg Arg Arg Arg Cys Leu Asn Gly Asn Pro Pro Lys Arg Leu
            35                  40                  45

Lys Arg Arg Asp Arg Arg Met Met Ser Gln Leu Glu Leu Leu Ser Gly
50                  55                  60

Gly Glu Met Leu Cys Gly Gly Phe Tyr Pro Arg Leu Ser Cys Cys Leu
65                  70                  75                  80

Arg Ser Asp Ser Pro Gly Leu Gly Arg Leu Glu Asn Lys Ile Phe Ser
                85                  90                  95

Val Thr Asn Asn Thr Glu Cys Gly Lys Leu Leu Glu Glu Ile Lys Cys
                100                 105                 110

Ala Leu Cys Ser Pro His Ser Gln Ser Leu Phe His Ser Pro Glu Arg
            115                 120                 125

Glu Val Leu Glu Arg Asp Leu Val Leu Pro Leu Leu Cys Lys Asp Tyr
130                 135                 140

Cys Lys Glu Phe Phe Tyr Thr Cys Arg Gly His Ile Pro Gly Phe Leu
145                 150                 155                 160

Gln Thr Thr Ala Asp Glu Phe Cys Phe Tyr Tyr Ala Arg Lys Asp Gly
                165                 170                 175

Gly Leu Cys Phe Pro Asp Phe Pro Arg Lys Gln Val Arg Gly Pro Ala
            180                 185                 190

Ser Asn Tyr Leu Asp Gln Met Glu Glu Tyr Asp Lys Val Glu Glu Ile
            195                 200                 205

Ser Arg Lys His Lys His Asn Cys Phe Cys Ile Gln Glu Val Val Ser
    210                 215                 220

Gly Leu Arg Gln Pro Val Gly Ala Leu His Ser Gly Asp Gly Ser Gln
225                 230                 235                 240

Arg Leu Phe Ile Leu Glu Lys Glu Gly Tyr Val Lys Ile Leu Thr Pro
                245                 250                 255

Glu Gly Glu Ile Phe Lys Glu Pro Tyr Leu Asp Ile His Lys Leu Val
            260                 265                 270

Gln Ser Gly Ile Lys Gly Gly Asp Glu Arg Gly Leu Leu Ser Leu Ala
        275                 280                 285

Phe His Pro Asn Tyr Lys Lys Asn Gly Lys Leu Tyr Val Ser Tyr Thr
290                 295                 300

Thr Asn Gln Glu Arg Trp Ala Ile Gly Pro His Asp His Ile Leu Arg
305                 310                 315                 320

Val Val Glu Tyr Thr Val Ser Arg Lys Asn Pro His Gln Val Asp Leu
                325                 330                 335

Arg Thr Ala Arg Val Phe Leu Glu Val Ala Glu Leu His Arg Lys His
            340                 345                 350

Leu Gly Gly Gln Leu Leu Phe Gly Pro Asp Gly Phe Leu Tyr Ile Ile
        355                 360                 365

Leu Gly Asp Gly Met Ile Thr Leu Asp Asp Met Glu Glu Met Asp Gly
370                 375                 380

```
Leu Ser Asp Phe Thr Gly Ser Val Leu Arg Leu Asp Val Asp Thr Asp
385                 390                 395                 400

Met Cys Asn Val Pro Tyr Ser Ile Pro Arg Ser Asn Pro His Phe Asn
                405                 410                 415

Ser Thr Asn Gln Pro Pro Glu Val Phe Ala His Gly Leu His Asp Pro
            420                 425                 430

Gly Arg Cys Ala Val Asp Arg His Pro Thr Asp Ile Asn Ile Asn Leu
        435                 440                 445

Thr Ile Leu Cys Ser Asp Ser Asn Gly Lys Asn Arg Ser Ser Ala Arg
    450                 455                 460

Ile Leu Gln Ile Ile Lys Gly Lys Asp Tyr Glu Ser Glu Pro Ser Leu
465                 470                 475                 480

Leu Glu Phe Lys Pro Phe Ser Asn Gly Pro Leu Val Gly Gly Phe Val
                485                 490                 495

Tyr Arg Gly Cys Gln Ser Glu Arg Leu Tyr Gly Ser Tyr Val Phe Gly
            500                 505                 510

Asp Arg Asn Gly Asn Phe Leu Thr Leu Gln Gln Ser Pro Val Thr Lys
        515                 520                 525

Gln Trp Gln Glu Lys Pro Leu Cys Leu Gly Thr Ser Gly Ser Cys Arg
    530                 535                 540

Gly Tyr Phe Ser Gly His Ile Leu Gly Phe Gly Glu Asp Glu Leu Gly
545                 550                 555                 560

Glu Val Tyr Ile Leu Ser Ser Lys Ser Met Thr Gln Thr His Asn
                565                 570                 575

Gly Lys Leu Tyr Lys Ile Val Asp Pro Lys Arg Pro Leu Met Pro Glu
            580                 585                 590

Glu Cys Arg Ala Thr Val Gln Pro Ala Gln Thr Leu Thr Ser Glu Cys
        595                 600                 605

Ser Arg Leu Cys Arg Asn Gly Tyr Cys Thr Pro Thr Gly Lys Cys Cys
    610                 615                 620

Cys Ser Pro Gly Trp Glu Gly Asp Phe Cys Arg Thr Ala Lys Cys Glu
625                 630                 635                 640

Pro Ala Cys Arg His Gly Gly Val Cys Val Arg Pro Asn Lys Cys Leu
                645                 650                 655

Cys Lys Lys Gly Tyr Leu Gly Pro Gln Cys Glu Gln Val Asp Arg Asn
            660                 665                 670

Ile Arg Arg Val Thr Arg Ala Gly Ile Leu Asp Gln Ile Ile Asp Met
        675                 680                 685

Thr Ser Tyr Leu Leu Asp Leu Thr Ser Tyr Ile Val
    690                 695                 700

<210> SEQ ID NO 5
<211> LENGTH: 2037
<212> TYPE: DNA
<213> ORGANISM: Mus musculus
<220> FEATURE:
<221> NAME/KEY: CDS
<222> LOCATION: (1)..(2037)
<223> OTHER INFORMATION: soluble Hip1 cDNA (murine)

<400> SEQUENCE: 5 atg ctg aag atg ctc tcg ttt aag ctg cta ctg ctg gcc gtg gct ctg      48
Met Leu Lys Met Leu Ser Phe Lys Leu Leu Leu Leu Ala Val Ala Leu
1               5                   10                  15 ggc ttc ttt gaa gga gat gcg aag ttt ggg gaa agg aac gag ggg agc      96
Gly Phe Phe Glu Gly Asp Ala Lys Phe Gly Glu Arg Asn Glu Gly Ser
            20                  25                  30
```

```
gga gcg aga agg aga cgg tgc ctg aat ggg aac ccc cca aag cgc cta      144
Gly Ala Arg Arg Arg Arg Cys Leu Asn Gly Asn Pro Pro Lys Arg Leu
        35                  40                  45 aag aga agg gac agg cgg gtg atg tcc cag ctg gag ctg ctc agt gga      192
Lys Arg Arg Asp Arg Arg Val Met Ser Gln Leu Glu Leu Leu Ser Gly
    50                  55                  60 gga gag atc ctg tgt ggt ggc ttc tac cca cga gta tct tgc tgc ctg      240
Gly Glu Ile Leu Cys Gly Gly Phe Tyr Pro Arg Val Ser Cys Cys Leu
65                  70                  75                  80 cag agt gac agc cct gga ttg ggg cgt ctg gag aac aag atc ttt tct      288
Gln Ser Asp Ser Pro Gly Leu Gly Arg Leu Glu Asn Lys Ile Phe Ser
                85                  90                  95 gcc acc aac aac tca gaa tgc agc agg ctg ctg gag gag atc caa tgt      336
Ala Thr Asn Asn Ser Glu Cys Ser Arg Leu Leu Glu Glu Ile Gln Cys
            100                 105                 110 gct ccc tgc tcc ccg cat tcc cag agc ctc ttc tac aca cct gaa aga      384
Ala Pro Cys Ser Pro His Ser Gln Ser Leu Phe Tyr Thr Pro Glu Arg
        115                 120                 125 gat gtc ctg gat ggg gac cta gca ctt cca ctc ctc tgc aaa gac tac      432
Asp Val Leu Asp Gly Asp Leu Ala Leu Pro Leu Leu Cys Lys Asp Tyr
    130                 135                 140 tgc aaa gaa ttc ttt tat act tgc cga ggc cat att cca ggt ctt ctt      480
Cys Lys Glu Phe Phe Tyr Thr Cys Arg Gly His Ile Pro Gly Leu Leu
145                 150                 155                 160 caa aca act gct gat gaa ttt tgc ttt tac tat gca aga aaa gat gct      528
Gln Thr Thr Ala Asp Glu Phe Cys Phe Tyr Tyr Ala Arg Lys Asp Ala
                165                 170                 175 ggg tta tgc ttt cca gac ttc ccg aga aag caa gtc aga gga cca gca      576
Gly Leu Cys Phe Pro Asp Phe Pro Arg Lys Gln Val Arg Gly Pro Ala
            180                 185                 190 tct aac tac ttg ggc cag atg gaa gac tac gag aaa gtg ggg ggg atc      624
Ser Asn Tyr Leu Gly Gln Met Glu Asp Tyr Glu Lys Val Gly Gly Ile
        195                 200                 205 agc aga aaa cac aaa cac aac tgc ctc tgt gtc cag gag gtc atg agt      672
Ser Arg Lys His Lys His Asn Cys Leu Cys Val Gln Glu Val Met Ser
    210                 215                 220 ggg ctg cgg cag cct gtg agc gct gtg cac agc ggg gat ggc tcc cat      720
Gly Leu Arg Gln Pro Val Ser Ala Val His Ser Gly Asp Gly Ser His
225                 230                 235                 240 cgg ctc ttc att cta gag aag gaa ggc tac gtg aag att cta acc cca      768
Arg Leu Phe Ile Leu Glu Lys Glu Gly Tyr Val Lys Ile Leu Thr Pro
                245                 250                 255 gaa gga gaa ctg ttc aag gag cct tac ttg gac att cac aaa ctt gtt      816
Glu Gly Glu Leu Phe Lys Glu Pro Tyr Leu Asp Ile His Lys Leu Val
            260                 265                 270 caa agt gga ata aag gga gga gac gaa agg ggc ctg cta agc ctg gca      864
Gln Ser Gly Ile Lys Gly Gly Asp Glu Arg Gly Leu Leu Ser Leu Ala
        275                 280                 285 ttc cat ccc aat tac aag aaa aat gga aag ctg tat gtg tct tat acc      912
Phe His Pro Asn Tyr Lys Lys Asn Gly Lys Leu Tyr Val Ser Tyr Thr
    290                 295                 300 acc aac cag gaa cgg tgg gct att ggg cct cac gac cac att ctt cgg      960
Thr Asn Gln Glu Arg Trp Ala Ile Gly Pro His Asp His Ile Leu Arg
305                 310                 315                 320 gtt gtg gaa tac aca gta tcc agg aaa aac ccc cat caa gtt gat gtg     1008
Val Val Glu Tyr Thr Val Ser Arg Lys Asn Pro His Gln Val Asp Val
                325                 330                 335 aga aca gcc agg gtg ttt ctg gaa gtc gca gag ctc cac cga aag cat     1056
Arg Thr Ala Arg Val Phe Leu Glu Val Ala Glu Leu His Arg Lys His
```

```
                340               345               350
ctt ggg gga cag ctg ctc ttt ggt cct gat ggc ttt ttg tac atc atc    1104
Leu Gly Gly Gln Leu Leu Phe Gly Pro Asp Gly Phe Leu Tyr Ile Ile
        355               360               365 ctt ggg gat ggt atg atc aca ttg gat gac atg gaa gag atg gat ggg    1152
Leu Gly Asp Gly Met Ile Thr Leu Asp Asp Met Glu Glu Met Asp Gly
    370               375               380 tta agt gac ttc aca ggc tct gtg ctg agg ctg gac gtg gac acc gac    1200
Leu Ser Asp Phe Thr Gly Ser Val Leu Arg Leu Asp Val Asp Thr Asp
385               390               395               400 atg tgc aat gtg cct tat tcc ata cct cgg agt aac cct cac ttc aac    1248
Met Cys Asn Val Pro Tyr Ser Ile Pro Arg Ser Asn Pro His Phe Asn
                405               410               415 agc acc aac cag ccc cca gaa gta ttt gcc cac ggc ctc cat gat cca    1296
Ser Thr Asn Gln Pro Pro Glu Val Phe Ala His Gly Leu His Asp Pro
            420               425               430 ggc aga tgt gcc gtg gat cga cat cct act gat ata aac atc aat tta    1344
Gly Arg Cys Ala Val Asp Arg His Pro Thr Asp Ile Asn Ile Asn Leu
        435               440               445 aca ata ctt tgc tca gat tcc aac ggg aaa aac agg tca tca gcc aga    1392
Thr Ile Leu Cys Ser Asp Ser Asn Gly Lys Asn Arg Ser Ser Ala Arg
    450               455               460 atc cta cag ata ata aag gga aga ggt tat gaa agt gag cca tct ctt    1440
Ile Leu Gln Ile Ile Lys Gly Arg Gly Tyr Glu Ser Glu Pro Ser Leu
465               470               475               480 ctt gaa ttc aag cca ttc agt aac ggc cct ttg gtt ggt gga ttt gtt    1488
Leu Glu Phe Lys Pro Phe Ser Asn Gly Pro Leu Val Gly Gly Phe Val
                485               490               495 tac aga ggc tgt cag tct gaa aga ttg tac gga agc tat gtg ttc gga    1536
Tyr Arg Gly Cys Gln Ser Glu Arg Leu Tyr Gly Ser Tyr Val Phe Gly
            500               505               510 gat cgc aat ggg aat ttc tta acc ctc cag caa agc cca gtg acc aag    1584
Asp Arg Asn Gly Asn Phe Leu Thr Leu Gln Gln Ser Pro Val Thr Lys
        515               520               525 caa tgg caa gaa aag ccg ctc tgc ctg ggt gcc agc agc tcc tgt cga    1632
Gln Trp Gln Glu Lys Pro Leu Cys Leu Gly Ala Ser Ser Ser Cys Arg
    530               535               540 ggc tac ttt tcg ggt cac atc ttg gga ttt gga gaa gat gaa tta gga    1680
Gly Tyr Phe Ser Gly His Ile Leu Gly Phe Gly Glu Asp Glu Leu Gly
545               550               555               560 gag gtt tac att cta tca agc agt aag agt atg acc cag act cac aat    1728
Glu Val Tyr Ile Leu Ser Ser Ser Lys Ser Met Thr Gln Thr His Asn
                565               570               575 gga aaa ctc tac aag atc gta gac ccc aaa aga cct tta atg cct gag    1776
Gly Lys Leu Tyr Lys Ile Val Asp Pro Lys Arg Pro Leu Met Pro Glu
            580               585               590 gaa tgc aga gtc aca gtt caa cct gcc cag cca ctg acc tcc gat tgc    1824
Glu Cys Arg Val Thr Val Gln Pro Ala Gln Pro Leu Thr Ser Asp Cys
        595               600               605 tcc cgg ctc tgt cga aac ggc tac tac acc ccc act ggc aag tgc tgc    1872
Ser Arg Leu Cys Arg Asn Gly Tyr Tyr Thr Pro Thr Gly Lys Cys Cys
    610               615               620 tgc agt ccc ggc tgg gag gga gac ttc tgc aga att gcc aag tgt gag    1920
Cys Ser Pro Gly Trp Glu Gly Asp Phe Cys Arg Ile Ala Lys Cys Glu
625               630               635               640 cca gcg tgc cgt cat gga ggt gtc tgt gtc aga ccg aac aag tgc ctc    1968
Pro Ala Cys Arg His Gly Gly Val Cys Val Arg Pro Asn Lys Cys Leu
                645               650               655 tgt aaa aag ggc tat ctt ggt cct caa tgt gaa caa gtg gac agg aac    2016
```

```
Cys Lys Lys Gly Tyr Leu Gly Pro Gln Cys Glu Gln Val Asp Arg Asn
              660                 665                 670 gtc cgc aga gtg acc agg tga                                                    2037
Val Arg Arg Val Thr Arg
            675

<210> SEQ ID NO 6
<211> LENGTH: 678
<212> TYPE: PRT
<213> ORGANISM: Mus musculus

<400> SEQUENCE: 6

Met Leu Lys Met Leu Ser Phe Lys Leu Leu Leu Ala Val Ala Leu
1               5                   10                  15

Gly Phe Phe Glu Gly Asp Ala Lys Phe Gly Glu Arg Asn Glu Gly Ser
                20                  25                  30

Gly Ala Arg Arg Arg Cys Leu Asn Gly Asn Pro Pro Lys Arg Leu
            35                  40                  45

Lys Arg Arg Asp Arg Arg Val Met Ser Gln Leu Glu Leu Leu Ser Gly
        50                  55                  60

Gly Glu Ile Leu Cys Gly Gly Phe Tyr Pro Arg Val Ser Cys Cys Leu
65                  70                  75                  80

Gln Ser Asp Ser Pro Gly Leu Gly Arg Leu Glu Asn Lys Ile Phe Ser
                85                  90                  95

Ala Thr Asn Asn Ser Glu Cys Ser Arg Leu Leu Glu Glu Ile Gln Cys
            100                 105                 110

Ala Pro Cys Ser Pro His Ser Gln Ser Leu Phe Tyr Thr Pro Glu Arg
        115                 120                 125

Asp Val Leu Asp Gly Asp Leu Ala Leu Pro Leu Leu Cys Lys Asp Tyr
    130                 135                 140

Cys Lys Glu Phe Phe Tyr Thr Cys Arg Gly His Ile Pro Gly Leu Leu
145                 150                 155                 160

Gln Thr Thr Ala Asp Glu Phe Cys Phe Tyr Tyr Ala Arg Lys Asp Ala
                165                 170                 175

Gly Leu Cys Phe Pro Asp Phe Pro Arg Lys Gln Val Arg Gly Pro Ala
            180                 185                 190

Ser Asn Tyr Leu Gly Gln Met Glu Asp Tyr Glu Lys Val Gly Gly Ile
        195                 200                 205

Ser Arg Lys His Lys His Asn Cys Leu Cys Val Gln Glu Val Met Ser
    210                 215                 220

Gly Leu Arg Gln Pro Val Ser Ala Val His Ser Gly Asp Gly Ser His
225                 230                 235                 240

Arg Leu Phe Ile Leu Glu Lys Glu Gly Tyr Val Lys Ile Leu Thr Pro
                245                 250                 255

Glu Gly Glu Leu Phe Lys Glu Pro Tyr Leu Asp Ile His Lys Leu Val
            260                 265                 270

Gln Ser Gly Ile Lys Gly Gly Asp Glu Arg Gly Leu Leu Ser Leu Ala
        275                 280                 285

Phe His Pro Asn Tyr Lys Lys Asn Gly Lys Leu Tyr Val Ser Tyr Thr
    290                 295                 300

Thr Asn Gln Glu Arg Trp Ala Ile Gly Pro His Asp His Ile Leu Arg
305                 310                 315                 320

Val Val Glu Tyr Thr Val Ser Arg Lys Asn Pro His Gln Val Asp Val
                325                 330                 335

Arg Thr Ala Arg Val Phe Leu Glu Val Ala Glu Leu His Arg Lys His
```

-continued

```
                    340                 345                 350
Leu Gly Gly Gln Leu Leu Phe Gly Pro Asp Gly Phe Leu Tyr Ile Ile
            355                 360                 365
Leu Gly Asp Gly Met Ile Thr Leu Asp Asp Met Glu Glu Met Asp Gly
        370                 375                 380
Leu Ser Asp Phe Thr Gly Ser Val Leu Arg Leu Asp Val Asp Thr Asp
385                 390                 395                 400
Met Cys Asn Val Pro Tyr Ser Ile Pro Arg Ser Asn Pro His Phe Asn
                405                 410                 415
Ser Thr Asn Gln Pro Pro Glu Val Phe Ala His Gly Leu His Asp Pro
            420                 425                 430
Gly Arg Cys Ala Val Asp Arg His Pro Thr Asp Ile Asn Ile Asn Leu
        435                 440                 445
Thr Ile Leu Cys Ser Asp Ser Asn Gly Lys Asn Arg Ser Ser Ala Arg
450                 455                 460
Ile Leu Gln Ile Ile Lys Gly Arg Gly Tyr Glu Ser Glu Pro Ser Leu
465                 470                 475                 480
Leu Glu Phe Lys Pro Phe Ser Asn Gly Pro Leu Val Gly Gly Phe Val
                485                 490                 495
Tyr Arg Gly Cys Gln Ser Glu Arg Leu Tyr Gly Ser Tyr Val Phe Gly
            500                 505                 510
Asp Arg Asn Gly Asn Phe Leu Thr Leu Gln Gln Ser Pro Val Thr Lys
        515                 520                 525
Gln Trp Gln Glu Lys Pro Leu Cys Leu Gly Ala Ser Ser Ser Cys Arg
    530                 535                 540
Gly Tyr Phe Ser Gly His Ile Leu Gly Phe Gly Glu Asp Glu Leu Gly
545                 550                 555                 560
Glu Val Tyr Ile Leu Ser Ser Lys Ser Met Thr Gln Thr His Asn
                565                 570                 575
Gly Lys Leu Tyr Lys Ile Val Asp Pro Lys Arg Pro Leu Met Pro Glu
            580                 585                 590
Glu Cys Arg Val Thr Val Gln Pro Ala Gln Pro Leu Thr Ser Asp Cys
        595                 600                 605
Ser Arg Leu Cys Arg Asn Gly Tyr Tyr Thr Pro Thr Gly Lys Cys Cys
    610                 615                 620
Cys Ser Pro Gly Trp Glu Gly Asp Phe Cys Arg Ile Ala Lys Cys Glu
625                 630                 635                 640
Pro Ala Cys Arg His Gly Gly Val Cys Val Arg Pro Asn Lys Cys Leu
                645                 650                 655
Cys Lys Lys Gly Tyr Leu Gly Pro Gln Cys Glu Gln Val Asp Arg Asn
            660                 665                 670
Val Arg Arg Val Thr Arg
        675

<210> SEQ ID NO 7
<211> LENGTH: 6814
<212> TYPE: DNA
<213> ORGANISM: Artificial
<220> FEATURE:
<223> OTHER INFORMATION: recombinant AAV vector (plasmid)
<220> FEATURE:
<221> NAME/KEY: CDS
<222> LOCATION: (1228)..(3264)
<223> OTHER INFORMATION: soluble Hip1 CDS

<400> SEQUENCE: 7
```

-continued

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccagattta     240
attaaggctg cgcgctcgct cgctcactga ggccgcccgg gcaaagcccg ggcgtcgggc     300
gacctttggt cgcccggcct cagtgagcga gcgagcgcgc agagagggag tggccaactc     360
catcactagg ggttccttgt agttaatgat taacccgcca tgctacttat ctacgtagcc     420
atgctctagg aagatcggaa ttcgcccttaa gctagctag ttattaatag taatcaatta     480
cggggtcatt agttcatagc ccatatatgg agttccgcgt tacataactt acggtaaatg     540
gcccgcctgg ctgaccgccc aacgacccc gcccattgac gtcaataatg acgtatgttc     600
ccatagtaac gccaataggg actttccatt gacgtcaatg ggtggagtat ttacggtaaa     660
ctgcccactt ggcagtacat caagtgtatc atatgccaag tacgccccct attgacgtca     720
atgacggtaa atggcccgcc tggcattatg cccagtacat gaccttatgg gactttccta     780
cttggcagta catctacgta ttagtcatcg ctattaccat ggtgatgcgg ttttggcagt     840
acatcaatgg gcgtggatag cggtttgact cacggggatt tccaagtctc cacccattg     900
acgtcaatgg gagtttgttt tggcaccaaa atcaacggga cttteccaaaa tgtcgtaaca    960
actccgcccc attgacgcaa atgggcggta ggcgtgtacg gtgggaggtc tatataagca    1020
gagctggttt agtgaaccgt cagatcctgc agaagttggt cgtgaggcac tgggcaggta    1080
agtatcaagg ttacaagaca ggtttaagga gaccaataga aactgggctt gtcgagacag    1140
agaagactct tgcgtttctg ataggcacct attggtctta ctgacatcca ctttgccttt    1200
ctctccacag gtgtccaggc ggccgcc atg ctg aag atg ctc tcg ttt aag ctg    1254
                                Met Leu Lys Met Leu Ser Phe Lys Leu
                                 1               5 cta ctg ctg gcc gtg gct ctg ggc ttc ttt gaa gga gat gcg aag ttt      1302
Leu Leu Leu Ala Val Ala Leu Gly Phe Phe Glu Gly Asp Ala Lys Phe
 10              15                  20                  25 ggg gaa agg aac gag ggg agc gga gcg aga agg aga cgg tgc ctg aat      1350
Gly Glu Arg Asn Glu Gly Ser Gly Ala Arg Arg Arg Arg Cys Leu Asn
             30                  35                  40 ggg aac ccc cca aag cgc cta aag aga agg gac agg cgg gtg atg tcc      1398
Gly Asn Pro Pro Lys Arg Leu Lys Arg Arg Asp Arg Arg Val Met Ser
         45                  50                  55 cag ctg gag ctg ctc agt gga gga gag atc ctg tgt ggt ggc ttc tac      1446
Gln Leu Glu Leu Leu Ser Gly Gly Glu Ile Leu Cys Gly Gly Phe Tyr
     60                  65                  70 cca cga gta tct tgc tgc ctg cag agt gac agc cct gga ttg ggg cgt      1494
Pro Arg Val Ser Cys Cys Leu Gln Ser Asp Ser Pro Gly Leu Gly Arg
 75                  80                  85 ctg gag aac aag atc ttt tct gcc acc aac aac tca gaa tgc agc agg      1542
Leu Glu Asn Lys Ile Phe Ser Ala Thr Asn Asn Ser Glu Cys Ser Arg
 90                  95                 100                 105 ctg ctg gag gag atc caa tgt gct ccc tgc tcc ccg cat tcc cag agc      1590
Leu Leu Glu Glu Ile Gln Cys Ala Pro Cys Ser Pro His Ser Gln Ser
             110                 115                 120 ctc ttc tac aca cct gaa aga gat gtc ctg gat ggg gac cta gca ctt      1638
Leu Phe Tyr Thr Pro Glu Arg Asp Val Leu Asp Gly Asp Leu Ala Leu
         125                 130                 135 cca ctc ctc tgc aaa gac tac tgc aaa gaa ttc ttt tat act tgc cga      1686
Pro Leu Leu Cys Lys Asp Tyr Cys Lys Glu Phe Phe Tyr Thr Cys Arg
     140                 145                 150
```

-continued

| | | | | | | | | | | | | | | | | |
|---|---|---|---|---|---|---|---|---|---|---|---|---|---|---|---|---|
| ggc | cat | att | cca | ggt | ctt | ctt | caa | aca | act | gct | gat | gaa | ttt | tgc | ttt | 1734 |
| Gly | His | Ile | Pro | Gly | Leu | Leu | Gln | Thr | Thr | Ala | Asp | Glu | Phe | Cys | Phe | |
| | 155 | | | | 160 | | | | | 165 | | | | | | |
| tac | tat | gca | aga | aaa | gat | gct | ggg | tta | tgc | ttt | cca | gac | ttc | ccg | aga | 1782 |
| Tyr | Tyr | Ala | Arg | Lys | Asp | Ala | Gly | Leu | Cys | Phe | Pro | Asp | Phe | Pro | Arg | |
| 170 | | | | | 175 | | | | | 180 | | | | | 185 | |
| aag | caa | gtc | aga | gga | cca | gca | tct | aac | tac | ttg | ggc | cag | atg | gaa | gac | 1830 |
| Lys | Gln | Val | Arg | Gly | Pro | Ala | Ser | Asn | Tyr | Leu | Gly | Gln | Met | Glu | Asp | |
| | | | | 190 | | | | | 195 | | | | | 200 | | |
| tac | gag | aaa | gtg | ggg | ggg | atc | agc | aga | aaa | cac | aaa | cac | aac | tgc | ctc | 1878 |
| Tyr | Glu | Lys | Val | Gly | Gly | Ile | Ser | Arg | Lys | His | Lys | His | Asn | Cys | Leu | |
| | | | 205 | | | | | 210 | | | | | 215 | | | |
| tgt | gtc | cag | gag | gtc | atg | agt | ggg | ctg | cgg | cag | cct | gtg | agc | gct | gtg | 1926 |
| Cys | Val | Gln | Glu | Val | Met | Ser | Gly | Leu | Arg | Gln | Pro | Val | Ser | Ala | Val | |
| | | 220 | | | | | 225 | | | | | 230 | | | | |
| cac | agc | ggg | gat | ggc | tcc | cat | cgg | ctc | ttc | att | cta | gag | aag | gaa | ggc | 1974 |
| His | Ser | Gly | Asp | Gly | Ser | His | Arg | Leu | Phe | Ile | Leu | Glu | Lys | Glu | Gly | |
| | 235 | | | | | 240 | | | | | 245 | | | | | |
| tac | gtg | aag | att | cta | acc | cca | gaa | gga | gaa | ctg | ttc | aag | gag | cct | tac | 2022 |
| Tyr | Val | Lys | Ile | Leu | Thr | Pro | Glu | Gly | Glu | Leu | Phe | Lys | Glu | Pro | Tyr | |
| 250 | | | | | 255 | | | | | 260 | | | | | 265 | |
| ttg | gac | att | cac | aaa | ctt | gtt | caa | agt | gga | ata | aag | gga | gga | gac | gaa | 2070 |
| Leu | Asp | Ile | His | Lys | Leu | Val | Gln | Ser | Gly | Ile | Lys | Gly | Gly | Asp | Glu | |
| | | | | 270 | | | | | 275 | | | | | 280 | | |
| agg | ggc | ctg | cta | agc | ctg | gca | ttc | cat | ccc | aat | tac | aag | aaa | aat | gga | 2118 |
| Arg | Gly | Leu | Leu | Ser | Leu | Ala | Phe | His | Pro | Asn | Tyr | Lys | Lys | Asn | Gly | |
| | | | 285 | | | | | 290 | | | | | 295 | | | |
| aag | ctg | tat | gtg | tct | tat | acc | acc | aac | cag | gaa | cgg | tgg | gct | att | ggg | 2166 |
| Lys | Leu | Tyr | Val | Ser | Tyr | Thr | Thr | Asn | Gln | Glu | Arg | Trp | Ala | Ile | Gly | |
| | | 300 | | | | | 305 | | | | | 310 | | | | |
| cct | cac | gac | cac | att | ctt | cgg | gtt | gtg | gaa | tac | aca | gta | tcc | agg | aaa | 2214 |
| Pro | His | Asp | His | Ile | Leu | Arg | Val | Val | Glu | Tyr | Thr | Val | Ser | Arg | Lys | |
| | 315 | | | | | 320 | | | | | 325 | | | | | |
| aac | ccc | cat | caa | gtt | gat | gtg | aga | aca | gcc | agg | gtg | ttt | ctg | gaa | gtc | 2262 |
| Asn | Pro | His | Gln | Val | Asp | Val | Arg | Thr | Ala | Arg | Val | Phe | Leu | Glu | Val | |
| 330 | | | | | 335 | | | | | 340 | | | | | 345 | |
| gca | gag | ctc | cac | cga | aag | cat | ctt | ggg | gga | cag | ctg | ctc | ttt | ggt | cct | 2310 |
| Ala | Glu | Leu | His | Arg | Lys | His | Leu | Gly | Gly | Gln | Leu | Leu | Phe | Gly | Pro | |
| | | | | 350 | | | | | 355 | | | | | 360 | | |
| gat | ggc | ttt | ttg | tac | atc | atc | ctt | ggg | gat | ggt | atg | atc | aca | ttg | gat | 2358 |
| Asp | Gly | Phe | Leu | Tyr | Ile | Ile | Leu | Gly | Asp | Gly | Met | Ile | Thr | Leu | Asp | |
| | | | 365 | | | | | 370 | | | | | 375 | | | |
| gac | atg | gaa | gag | atg | gat | ggg | tta | agt | gac | ttc | aca | ggc | tct | gtg | ctg | 2406 |
| Asp | Met | Glu | Glu | Met | Asp | Gly | Leu | Ser | Asp | Phe | Thr | Gly | Ser | Val | Leu | |
| | | 380 | | | | | 385 | | | | | 390 | | | | |
| agg | ctg | gac | gtg | gac | acc | gac | atg | tgc | aat | gtg | cct | tat | tcc | ata | cct | 2454 |
| Arg | Leu | Asp | Val | Asp | Thr | Asp | Met | Cys | Asn | Val | Pro | Tyr | Ser | Ile | Pro | |
| | 395 | | | | | 400 | | | | | 405 | | | | | |
| cgg | agt | aac | cct | cac | ttc | aac | agc | acc | aac | cag | ccc | cca | gaa | gta | ttt | 2502 |
| Arg | Ser | Asn | Pro | His | Phe | Asn | Ser | Thr | Asn | Gln | Pro | Pro | Glu | Val | Phe | |
| 410 | | | | | 415 | | | | | 420 | | | | | 425 | |
| gcc | cac | ggc | ctc | cat | gat | cca | ggc | aga | tgt | gcc | gtg | gat | cga | cat | cct | 2550 |
| Ala | His | Gly | Leu | His | Asp | Pro | Gly | Arg | Cys | Ala | Val | Asp | Arg | His | Pro | |
| | | | | 430 | | | | | 435 | | | | | 440 | | |
| act | gat | ata | aac | atc | aat | tta | aca | ata | ctt | tgc | tca | gat | tcc | aac | ggg | 2598 |
| Thr | Asp | Ile | Asn | Ile | Asn | Leu | Thr | Ile | Leu | Cys | Ser | Asp | Ser | Asn | Gly | |
| | | | 445 | | | | | 450 | | | | | 455 | | | |
| aaa | aac | agg | tca | tca | gcc | aga | atc | cta | cag | ata | ata | aag | gga | aga | ggt | 2646 |
| Lys | Asn | Arg | Ser | Ser | Ala | Arg | Ile | Leu | Gln | Ile | Ile | Lys | Gly | Arg | Gly | |

-continued

```
          460                 465                 470
tat gaa agt gag cca tct ctt ctt gaa ttc aag cca ttc agt aac ggc      2694
Tyr Glu Ser Glu Pro Ser Leu Leu Glu Phe Lys Pro Phe Ser Asn Gly
    475                 480                 485 cct ttg gtt ggt gga ttt gtt tac aga ggc tgt cag tct gaa aga ttg      2742
Pro Leu Val Gly Gly Phe Val Tyr Arg Gly Cys Gln Ser Glu Arg Leu
490                 495                 500                 505 tac gga agc tat gtg ttc gga gat cgc aat ggg aat ttc tta acc ctc      2790
Tyr Gly Ser Tyr Val Phe Gly Asp Arg Asn Gly Asn Phe Leu Thr Leu
                510                 515                 520 cag caa agc cca gtg acc aag caa tgg caa gaa aag ccg ctc tgc ctg      2838
Gln Gln Ser Pro Val Thr Lys Gln Trp Gln Glu Lys Pro Leu Cys Leu
            525                 530                 535 ggt gcc agc agc tcc tgt cga ggc tac ttt tcg ggt cac atc ttg gga      2886
Gly Ala Ser Ser Ser Cys Arg Gly Tyr Phe Ser Gly His Ile Leu Gly
        540                 545                 550 ttt gga gaa gat gaa tta gga gag gtt tac att cta tca agc agt aag      2934
Phe Gly Glu Asp Glu Leu Gly Glu Val Tyr Ile Leu Ser Ser Ser Lys
    555                 560                 565 agt atg acc cag act cac aat gga aaa ctc tac aag atc gta gac ccc      2982
Ser Met Thr Gln Thr His Asn Gly Lys Leu Tyr Lys Ile Val Asp Pro
570                 575                 580                 585 aaa aga cct tta atg cct gag gaa tgc aga gtc aca gtt caa cct gcc      3030
Lys Arg Pro Leu Met Pro Glu Glu Cys Arg Val Thr Val Gln Pro Ala
                590                 595                 600 cag cca ctg acc tcc gat tgc tcc cgg ctc tgt cga aac ggc tac tac      3078
Gln Pro Leu Thr Ser Asp Cys Ser Arg Leu Cys Arg Asn Gly Tyr Tyr
            605                 610                 615 acc ccc act ggc aag tgc tgc agt ccc ggc tgg gag gga gac ttc          3126
Thr Pro Thr Gly Lys Cys Cys Ser Pro Gly Trp Glu Gly Asp Phe
        620                 625                 630 tgc aga att gcc aag tgt gag cca gcg tgc cgt cat gga ggt gtc tgt      3174
Cys Arg Ile Ala Lys Cys Glu Pro Ala Cys Arg His Gly Gly Val Cys
    635                 640                 645 gtc aga ccg aac aag tgc ctc tgt aaa aag ggc tat ctt ggt cct caa      3222
Val Arg Pro Asn Lys Cys Leu Cys Lys Lys Gly Tyr Leu Gly Pro Gln
650                 655                 660                 665 tgt gaa caa gtg gac agg aac gtc cgc aga gtg acc agg tga              3264
Cys Glu Gln Val Asp Arg Asn Val Arg Arg Val Thr Arg
                670                 675 ggatccaatc aacctctgga ttacaaaatt tgtgaaagat tgactggtat tcttaactat   3324
gttgctcctt ttacgctatg tggatacgct gctttaatgc ctttgtatca tgctattgct   3384
tcccgtatgg ctttcatttt ctcctccttg tataaatcct ggttgctgtc tctttatgag   3444
gagttgtggc ccgttgtcag gcaacgtggc gtggtgtgca ctgtgtttgc tgacgcaacc   3504
cccactggtt gggcattgc caccacctgt cagctccttt ccgggacttt cgctttcccc    3564
ctccctattg ccacggcgga actcatcgcc gcctgccttg cccgctgctg dacagggggct   3624 cggctgttgg gcactgacaa ttccgtggtg ttgtcgggga agctgacgtc ctttccatgg   3684
ctgctcgcct gtgttccac ctggattctg cgcgggacgt ccttctgcta cgtcccttcg    3744
gccctcaatc cagcggacct tccttcccgc ggcctgctgc cggctctgcg gcctcttccg   3804
cgtcttcgag atctgcctcg actgtgcctt ctagttgcca gccatctgtt gtttgccccc   3864
cccccgtgcc ttccttgacc ctggaaggtg ccactcccac tgtcctttcc taataaaatg   3924
aggaaattgc atcgcattgt ctgagtaggt gtcattctat tctgggggt ggggtgggggc  3984 aggacagcaa gggggaggat tgggaagaca atagcaggca tgctggggac tcgagttaag   4044
```

```
ggcgaattcc cgattaggat cttcctagag catggctacg tagataagta gcatggcggg      4104
ttaatcatta actacaagga accccctagtg atggagttgg ccactccctc tctgcgcgct      4164
cgctcgctca ctgaggccgg gcgaccaaag gtcgcccgac gcccgggctt tgcccgggcg      4224
gcctcagtga gcgagcgagc gcgcagcctt aattaaccta attcactggc cgtcgtttta      4284
caacgtcgtg actgggaaaa ccctggcgtt acccaactta atcgccttgc agcacatccc      4344
cctttcgcca gctggcgtaa tagcgaagag gcccgcaccg atcgcccttc ccaacagttg      4404
cgcagcctga atggcgaatg ggacgcgccc tgtagcggcg cattaagcgc ggcgggtgtg      4464
gtggttacgc gcagcgtgac cgctacactt gccagcgccc tagcgcccgc tcctttcgct      4524
ttcttccctt cctttctcgc cacgttcgcc ggctttcccc gtcaagctct aaatcggggg      4584
ctccctttag ggttccgatt tagtgcttta cggcacctcg accccaaaaa acttgattag      4644
ggtgatggtt cacgtagtgg gccatcgccc tgatagacgg ttttcgccc tttgacgctg       4704 gagttcacgt tcctcaatag tggactcttg ttccaaactg gaacaacact caaccctatc      4764
tcggtctatt cttttgattt ataagggatt tttccgattt cggcctattg gttaaaaaat      4824
gagctgattt aacaaaaatt taacgcgaat tttaacaaaa tattaacgtt tataatttca      4884
ggtggcatct ttcggggaaa tgtgcgcgga accctattt gtttattttt ctaaatacat       4944
tcaaatatgt atccgctcat gagacaataa ccctgataaa tgcttcaata atattgaaaa      5004
aggaagagta tgagtattca acatttccgt gtcgccctta ttccctttt tgcggcattt       5064 tgccttcctg ttttgctca cccagaaacg ctggtgaaag taaaagatgc tgaagatcag       5124
ttgggtgcac gagtgggtta catcgaactg gatctcaata gtggtaagat ccttgagagt      5184
tttcgccccg aagaacgttt tccaatgatg agcacttta aagttctgct atgtggcgcg      5244
gtattatccc gtattgacgc cgggcaagag caactcggtc gccgcataca ctattctcag      5304
aatgacttgg ttgagtactc accagtcaca gaaaagcatc ttacggatgg catgacagta      5364
agagaattat gcagtgctgc cataaccatg agtgataaca ctgcggccaa cttacttctg      5424
acaacgatcg gaggaccgaa ggagctaacc gcttttttgc acaacatggg gatcatgta       5484 actcgccttg atcgttggga accggagctg aatgaagcca taccaaacga cgagcgtgac      5544
accacgatgc ctgtagtaat ggtaacaacg ttgcgcaaac tattaactgg cgaactactt      5604
actctagctt cccggcaaca attaatagac tggatggagg cggataaagt tgcaggacca      5664
cttctgcgct cggcccttcc ggctggctgg tttattgctg ataaatctgg agccggtgag      5724
cgtgggtctc gcggtatcat tgcagcactg gggccagatg gtaagccctc ccgtatcgta      5784
gttatctaca cgacggggag tcaggcaact atggatgaac gaaatagaca gatcgctgag      5844
ataggtgcct cactgattaa gcattggtaa ctgtcagacc aagtttactc atatatactt      5904
tagattgatt taaaacttca ttttaatt aaaaggatct aggtgaagat cctttttgat        5964
aatctcatga ccaaaatccc ttaacgtgag ttttcgttcc actgagcgtc agaccccgta      6024
gaaaagatca aaggatcttc ttgagatcct ttttttctgc gcgtaatctg ctgcttgcaa      6084
acaaaaaaac caccgctacc agcggtggtt tgtttgccgg atcaagagct accaactctt      6144
tttccgaagg taactggctt cagcagagcg cagataccaa atactgtcct tctagtgtag      6204
ccgtagttag gccaccactt caagaactct gtagcaccgc ctacatacct cgctctgcta      6264
atcctgttac cagtggctgc tgccagtggc gataagtcgt gtcttaccgg gttggactca      6324
agacgatagt taccggataa ggcgcagcgg tcgggctgaa cggggggttc gtgcacacag      6384
```

-continued

```
cccagcttgg agcgaacgac ctacaccgaa ctgagatacc tacagcgtga gctatgagaa      6444
agcgccacgc ttcccgaagg gagaaaggcg gacaggtatc cggtaagcgg cagggtcgga      6504
acaggagagc gcacgaggga gcttccaggg ggaaacgcct ggtatcttta tagtcctgtc      6564
gggtttcgcc acctctgact tgagcgtcga tttttgtgat gctcgtcagg ggggcggagc      6624
ctatggaaaa acgccagcaa cgcggccttt ttacggttcc tggccttttg ctgcggtttt      6684
gctcacatgt tctttcctgc gttatcccct gattctgtgg ataaccgtat taccgccttt      6744
gagtgagctg ataccgctcg ccgcagccga acgaccgagc gcagcgagtc agtgagcgag      6804
gaagcggaag                                                             6814
```

<210> SEQ ID NO 8
<211> LENGTH: 678
<212> TYPE: PRT
<213> ORGANISM: Artificial
<220> FEATURE:
<223> OTHER INFORMATION: recombinant AAV vector (plasmid)

<400> SEQUENCE: 8

```
Met Leu Lys Met Leu Ser Phe Lys Leu Leu Leu Ala Val Ala Leu
1               5                   10                  15

Gly Phe Phe Glu Gly Asp Ala Lys Phe Gly Glu Arg Asn Glu Gly Ser
                20                  25                  30

Gly Ala Arg Arg Arg Cys Leu Asn Gly Asn Pro Pro Lys Arg Leu
            35                  40                  45

Lys Arg Arg Asp Arg Arg Val Met Ser Gln Leu Glu Leu Leu Ser Gly
50                  55                  60

Gly Glu Ile Leu Cys Gly Gly Phe Tyr Pro Arg Val Ser Cys Cys Leu
65                  70                  75                  80

Gln Ser Asp Ser Pro Gly Leu Gly Arg Leu Glu Asn Lys Ile Phe Ser
                85                  90                  95

Ala Thr Asn Asn Ser Glu Cys Ser Arg Leu Leu Glu Glu Ile Gln Cys
                100                 105                 110

Ala Pro Cys Ser Pro His Ser Gln Ser Leu Phe Tyr Thr Pro Glu Arg
            115                 120                 125

Asp Val Leu Asp Gly Asp Leu Ala Leu Pro Leu Leu Cys Lys Asp Tyr
130                 135                 140

Cys Lys Glu Phe Phe Tyr Thr Cys Arg Gly His Ile Pro Gly Leu Leu
145                 150                 155                 160

Gln Thr Thr Ala Asp Glu Phe Cys Phe Tyr Tyr Ala Arg Lys Asp Ala
                165                 170                 175

Gly Leu Cys Phe Pro Asp Phe Pro Arg Lys Gln Val Arg Gly Pro Ala
            180                 185                 190

Ser Asn Tyr Leu Gly Gln Met Glu Asp Tyr Glu Lys Val Gly Gly Ile
        195                 200                 205

Ser Arg Lys His Lys His Asn Cys Leu Cys Val Gln Glu Val Met Ser
    210                 215                 220

Gly Leu Arg Gln Pro Val Ser Ala Val His Ser Gly Asp Gly Ser His
225                 230                 235                 240

Arg Leu Phe Ile Leu Glu Lys Glu Gly Tyr Val Lys Ile Leu Thr Pro
                245                 250                 255

Glu Gly Glu Leu Phe Lys Glu Pro Tyr Leu Asp Ile His Lys Leu Val
            260                 265                 270

Gln Ser Gly Ile Lys Gly Gly Asp Glu Arg Gly Leu Leu Ser Leu Ala
        275                 280                 285
```

-continued

```
Phe His Pro Asn Tyr Lys Lys Asn Gly Lys Leu Tyr Val Ser Tyr Thr
        290                 295                 300

Thr Asn Gln Glu Arg Trp Ala Ile Gly Pro His Asp His Ile Leu Arg
305                 310                 315                 320

Val Val Glu Tyr Thr Val Ser Arg Lys Asn Pro His Gln Val Asp Val
                325                 330                 335

Arg Thr Ala Arg Val Phe Leu Glu Val Ala Glu Leu His Arg Lys His
            340                 345                 350

Leu Gly Gly Gln Leu Leu Phe Gly Pro Asp Gly Phe Leu Tyr Ile Ile
        355                 360                 365

Leu Gly Asp Gly Met Ile Thr Leu Asp Asp Met Glu Glu Met Asp Gly
370                 375                 380

Leu Ser Asp Phe Thr Gly Ser Val Leu Arg Leu Asp Val Asp Thr Asp
385                 390                 395                 400

Met Cys Asn Val Pro Tyr Ser Ile Pro Arg Ser Asn Pro His Phe Asn
                405                 410                 415

Ser Thr Asn Gln Pro Pro Glu Val Phe Ala His Gly Leu His Asp Pro
            420                 425                 430

Gly Arg Cys Ala Val Asp Arg His Pro Thr Asp Ile Asn Ile Asn Leu
        435                 440                 445

Thr Ile Leu Cys Ser Asp Ser Asn Gly Lys Asn Arg Ser Ser Ala Arg
450                 455                 460

Ile Leu Gln Ile Ile Lys Gly Arg Gly Tyr Glu Ser Glu Pro Ser Leu
465                 470                 475                 480

Leu Glu Phe Lys Pro Phe Ser Asn Gly Pro Leu Val Gly Gly Phe Val
                485                 490                 495

Tyr Arg Gly Cys Gln Ser Glu Arg Leu Tyr Gly Ser Tyr Val Phe Gly
            500                 505                 510

Asp Arg Asn Gly Asn Phe Leu Thr Leu Gln Gln Ser Pro Val Thr Lys
        515                 520                 525

Gln Trp Gln Glu Lys Pro Leu Cys Leu Gly Ala Ser Ser Ser Cys Arg
530                 535                 540

Gly Tyr Phe Ser Gly His Ile Leu Gly Phe Gly Glu Asp Glu Leu Gly
545                 550                 555                 560

Glu Val Tyr Ile Leu Ser Ser Ser Lys Ser Met Thr Gln Thr His Asn
                565                 570                 575

Gly Lys Leu Tyr Lys Ile Val Asp Pro Lys Arg Pro Leu Met Pro Glu
            580                 585                 590

Glu Cys Arg Val Thr Val Gln Pro Ala Gln Pro Leu Thr Ser Asp Cys
        595                 600                 605

Ser Arg Leu Cys Arg Asn Gly Tyr Tyr Thr Pro Thr Gly Lys Cys Cys
610                 615                 620

Cys Ser Pro Gly Trp Glu Gly Asp Phe Cys Arg Ile Ala Lys Cys Glu
625                 630                 635                 640

Pro Ala Cys Arg His Gly Gly Val Cys Val Arg Pro Asn Lys Cys Leu
                645                 650                 655

Cys Lys Lys Gly Tyr Leu Gly Pro Gln Cys Glu Gln Val Asp Arg Asn
            660                 665                 670

Val Arg Arg Val Thr Arg
        675

<210> SEQ ID NO 9
<211> LENGTH: 19
```

```
<212> TYPE: DNA
<213> ORGANISM: Artificial
<220> FEATURE:
<223> OTHER INFORMATION: oligonucleotide for PCR

<400> SEQUENCE: 9
gtgaggctgc gagtgaccg                                                   19

<210> SEQ ID NO 10
<211> LENGTH: 24
<212> TYPE: DNA
<213> ORGANISM: Artificial
<220> FEATURE:
<223> OTHER INFORMATION: PCR oligonucleotide

<400> SEQUENCE: 10
cctggtcgtc agccgccagc acgc                                             24

<210> SEQ ID NO 11
<211> LENGTH: 20
<212> TYPE: DNA
<213> ORGANISM: Artificial
<220> FEATURE:
<223> OTHER INFORMATION: PCR oligonucleotide

<400> SEQUENCE: 11
ctgctgctat ccatcagcgt                                                  20

<210> SEQ ID NO 12
<211> LENGTH: 20
<212> TYPE: DNA
<213> ORGANISM: Artificial
<220> FEATURE:
<223> OTHER INFORMATION: PCR oligonucleotide

<400> SEQUENCE: 12
aagaaggata agaggacagg                                                  20

<210> SEQ ID NO 13
<211> LENGTH: 40
<212> TYPE: DNA
<213> ORGANISM: Artificial
<220> FEATURE:
<223> OTHER INFORMATION: PCR oligonucleotide primer

<400> SEQUENCE: 13
aagcggccgc atgctgaaga tgctctcgtt taagctgcta                            40

<210> SEQ ID NO 14
<211> LENGTH: 32
<212> TYPE: DNA
<213> ORGANISM: Artificial
<220> FEATURE:
<223> OTHER INFORMATION: PCR oligonucleotide primer

<400> SEQUENCE: 14
aaggatccct acctggtcac tctgcggacg tt                                    32

<210> SEQ ID NO 15
<211> LENGTH: 23
<212> TYPE: RNA
<213> ORGANISM: artificial
<220> FEATURE:
<223> OTHER INFORMATION: Shh-siRNA-antisense

<400> SEQUENCE: 15
```

```
uaugaugucg ggguuguaau uuu                                           23

<210> SEQ ID NO 16
<211> LENGTH: 23
<212> TYPE: RNA
<213> ORGANISM: artificial
<220> FEATURE:
<223> OTHER INFORMATION: Shh-siRNA-sense

<400> SEQUENCE: 16
aauuacaacc ccgacaucau auu                                           23

<210> SEQ ID NO 17
<211> LENGTH: 22
<212> TYPE: RNA
<213> ORGANISM: artificial
<220> FEATURE:
<223> OTHER INFORMATION: Smo-siRNA-sense

<400> SEQUENCE: 17
aaggccuucu cuaagcggca uu                                            22

<210> SEQ ID NO 18
<211> LENGTH: 22
<212> TYPE: RNA
<213> ORGANISM: artificial
<220> FEATURE:
<223> OTHER INFORMATION: Smo-siRNA-antisense

<400> SEQUENCE: 18
ugccgcuuag agaaggccuu uu                                            22

<210> SEQ ID NO 19
<211> LENGTH: 21
<212> TYPE: RNA
<213> ORGANISM: artificial
<220> FEATURE:
<223> OTHER INFORMATION: Gli1-siRNA-sense

<400> SEQUENCE: 19
acgccgcagc agcagcuccu u                                             21

<210> SEQ ID NO 20
<211> LENGTH: 21
<212> TYPE: RNA
<213> ORGANISM: artificial
<220> FEATURE:
<223> OTHER INFORMATION: Gli1-siRNA-antisense

<400> SEQUENCE: 20
ggagcugcug cugcggcguu u                                             21
```